(12) United States Patent
Salgia et al.

(10) Patent No.: US 11,390,922 B2
(45) Date of Patent: Jul. 19, 2022

(54) C-CBL MUTATIONS AND USES THEREOF

(71) Applicant: University of Chicago, Chicago, IL (US)

(72) Inventors: Ravi Salgia, Park Ridge, IL (US); Soundarajan Krishnaswamy, Riyadh (SA); Yi-Hung Carol Tan, Chicago, IL (US); Suvobroto Nandi, Arlington, VA (US)

(73) Assignee: University of Chicago, Chicago, IL (US)

( * ) Notice: Subject to any disclaimer, the term of this patent is extended or adjusted under 35 U.S.C. 154(b) by 208 days.

(21) Appl. No.: 15/990,301

(22) Filed: May 25, 2018

(65) Prior Publication Data

US 2018/0327864 A1     Nov. 15, 2018

Related U.S. Application Data

(63) Continuation of application No. 15/077,409, filed on Mar. 22, 2016, now abandoned, which is a continuation of application No. 13/701,569, filed as application No. PCT/US2011/039125 on Jun. 3, 2011, now abandoned.

(60) Provisional application No. 61/351,501, filed on Jun. 4, 2010.

(51) Int. Cl.
  *C12Q 1/68* (2018.01)
  *C12Q 1/6886* (2018.01)
  *G01N 33/68* (2006.01)

(52) U.S. Cl.
  CPC ....... *C12Q 1/6886* (2013.01); *G01N 33/6893* (2013.01); *C12Q 2600/106* (2013.01); *C12Q 2600/156* (2013.01)

(58) Field of Classification Search
  None
  See application file for complete search history.

(56) References Cited

U.S. PATENT DOCUMENTS

2010/0062441 A1    3/2010 Salgia

FOREIGN PATENT DOCUMENTS

WO    2011/153472 A2    12/2011

OTHER PUBLICATIONS

Gazdaretal; Lung Cancer, vol. 68, pp. 309-318, 2010.*
Yu et al; Nature Communications, 2019; 10:3574, pp. 1-11.*
Liu et al; Nature Communications, 2019, 10:2138 pp. 1-12.*
U.S. Appl. No. 15/077,409, filed Mar. 22, 2016.
U.S. Appl. No. 13/701,569, filed Apr. 29, 2013.
PCT/US2011/039125, Jun. 3, 2011.
Abidoye O, et al. (2007) Lung carcinoma in African Americans. Nat Clin Pract Oncol. 4(2):118-129.
Caligiuri Ma, et al. (2007) Novel c-CBL and CBL-b ubiquitin ligase mutations in human acute myeloid leukemia. Blood. 110(3): 1022-1024.
Cappuzzo F, et al. (2009) Increased MET gene copy number negatively affects survival of surgically resected non-small-cell lung cancer patients. J Clin Oncol. 27(10): 1667-1674.
Chiarle R, et al. (2008) The anaplastic lymphoma kinase in the pathogenesis of cancer. Nat Rev Cancer. 8(1):11-23.
Christensen JG, et al. (2005) c-Met as a target for human cancer and characterization of inhibitors for therapeutic intervention. Cancer Lett. 225(1):1-26.
Date K, et al. (1997) HGF/NK4 is a specific antagonist for pleiotrophic actions of hepatocyte growth factor. FEBS Lett. 420(1):1-6.
Dunbar AJ, et al. (2008) 250K single nucleotide polymorphism array karyotyping identifies acquired uniparental disomy and homozygous mutations, including novel missense substitutions of c-Cbl, in myeloid malignancies. Cancer Res. 68(24): 10349-10357.
Engelman JA, et al. (2007) MET amplification leads to gefitinib resistance in lung cancer by activating ERBB3 signaling. Science. 316(5827):1039-1043.
Grand FH, et al. (2009) Frequent CBL mutations associated with 1 lq acquired uniparental disomy in myeloproliferative neoplasms. Blood. 113(24):6182-6192.
Hanahan D, et al. (2000) The hallmarks of cancer. Cell. 100(1):57-70.
Herrmann J, et al. (2007) Ubiquitin and ubiquitin-like proteins in protein regulation. Circ Res. 100(9):1276-1291.
Hou J, et al. (2010) Gene expression-based classification of non-small cell lung carcinomas and survival prediction. PLoS One. 5(4):e10312.
Inamura K, et al. (2008) EML4-ALK fusion is linked to histological characteristics in a subset oflung cancers. J Thorne Oncol. 3(1):13-17.
Jagadeeswaran R, et al. (2008) Paxillin is a target for somatic mutations in lung cancer: implications for cell growth and invasion. Cancer Res. 68(1):132-142.
Jemal A, et al. (2009) Cancer statistics, 2009. CA Cancer J Clin. 59(4):225-249.
Koivunen JP, et al. (2008) EML4-ALK fusion gene and efficacy of an ALK kinase inhibitor in lung cancer. Clin Cancer Res. 14(13):4275-4283.
Kozlov G, et al. (2007) Structural basis for UBA-mediated dimerization of c-Cbl ubiquitin ligase. J Biol Chem. 282(37):27547-27555.
Krishnaswamy S, et al. (2009) Ethnic differences and functional analysis of MET mutations in lung cancer. Clin Cancer Res. 15(18):5714-5723.
Lill NL, et al. (2000) The evolutionarily conserved N-terminal region of Cbl is sufficient to enhance down-regulation of the epidermal growth factor receptor. J Biol Chem. 275(1):367-377.
Ma PC, et al. (2008) Expression and mutational analysis of MET in human solid cancers. Genes Chromosomes Cancer. 47(12):1025-1037.

(Continued)

*Primary Examiner* — Jehanne S Sitton
(74) *Attorney, Agent, or Firm* — Kilpatrick Townsend & Stoctkon LLP

(57) ABSTRACT

The present invention relates generally to the fields of molecular biology and growth factor regulation. The invention concerns methods and compositions useful for diagnosing and treating human lung cancer associated with mutated c-CBL.

5 Claims, 37 Drawing Sheets

Specification includes a Sequence Listing.

(56) References Cited

OTHER PUBLICATIONS

Ma PC, et al. (2005) Functional expression and mutations of c-Met and its therapeutic inhibition with SUI 1274 and small interfering RNA in non-small cell lung cancer. Cancer Res. 65(4):1479-1488.
Mark MR, et al. (1992) Expression and characterization of hepatocyte growth factor receptor-IgG fusion proteins. Effects of mutations in the potential proteolytic cleavage site on processing and ligand binding. J Biol Chem. 267(36):26166-26171.
Michieli P, et al. (1999) Mutant Met-mediated transformation is ligand-dependent and can be inhibited by HGF antagonists. Oncogene. 18(37):5221-5231.
Miyake S, et al. (1999) Cbl-mediated negative regulation of platelet-derived growth factor receptor-dependent cell proliferation. A critical role for Cbl tyrosine kinase-binding domain. J Biol Chem. 274(23):16619-16628.
Mosse YP, et al. (2009) Inhibition of ALK signaling for cancer therapy. Clin Cancer Res. 15(18):5609-5614.
Ng C, et al. (2008) Structural basis for a novel intrapeptidyl H-bond and reverse binding of c-Cbl-TKB domain substrates. Embo J. 27(5):804-816.
Oved S, et al. (2002) Signal transduction: molecular ticket to enter cells. Nature. 416(6877): 133-136.
Parr C, et al. (2000) Nk4, a new HGF/SF variant, is an antagonist to the influence of HGF/SF on the motility and invasion of colon cancer cells. Int J Cancer. 85(4):563-570.
Pasqualetti G, et al. (2011) Synergistic cytotoxicity, inhibition of signal transduction pathways and pharmacogenetics of sorafenib and gemcitabine in human NSCLC cell lines. Lung Cancer. 74(2):197-205.
Pennock S, et al. (2008) A tale of two Cbls: interplay of c-Cbl and Cbl-b in epidermal growth factor receptor downregulation. Mol Cell Biol. 28(9):3020-3037.
Peschard P, et al. (2001) Mutation of the c-Cbl TKB domain binding site on the Met receptor tyrosine kinase converts it into a transforming protein. Mol Cell. 8(5):995-1004.
Potti A, et al. (2006) A genomic strategy to refine prognosis in early-stage nonsmall-cell lung cancer. N Engl J Med. 355(6):570-580.
Reindl C, et al. (2009) CBL exon 8/9 mutants activate the FL T3 pathway and cluster in core binding factor/11q deletion acute myeloid leukemia/myelodysplastic syndrome subtypes. Clin Cancer Res. 15(7):2238-2247.
Sanada M, et al. (2009) Gain-of-function of mutated C-CBL tumour suppressor in myeloid neoplasms. Nature. 460(7257):904-908.
Sargin B, et al. (2007) Flt3-dependent transformation by inactivating c-Cbl mutations in AML. Blood. 110(3):1004-1012.
Sattler M, et al. (2003) A novel small molecule met inhibitor induces apoptosis in cells transformed by the oncogenic TPR-MET tyrosine kinase. Cancer Res. 63(17):5462-5469.
Sattler M, et al. (2009) The MET axis as a therapeutic target. Update Cancer Ther. 3(3):109-118.
Sharma SV, et al. (2010) Nat Rev Cancer. Cell line-based platforms to evaluate the therapeutic efficacy of candidate anticancer agents. 10(4):241-253.
Shaw AT, et al. (2009) Clinical features and outcome of patients with non-small-cell Tung cancer who harbor EML4-ALK. J Clin Oncol. 27(26):4247-4253.
Shi Y, et al. (2011) C100RF97 is a novel tumor-suppressor gene of non-small-cell 42. lung cancer and a functional variant of this gene increases the risk of non-small-cell lung cancer. Oncogene. 30(39):4107-4117.
Soda M, et al. (2008) A mouse model for EML4-ALK-positive lung cancer. Proc Natl Acad Sci US A. 105(50):19893-19897.
Ss2227988 (rs2227988, dbSNP NLM, NCBI, 2007).
Swaminathan G, et al. (2006) The Cbl family proteins: ring leaders in regulation of cell signaling. J Cell Physiol. 209(1):21-43.
Tan YH, et al. (2010) CBL is frequently altered in lung cancers: its relationship to mutations in MET and EGFR tyrosine kinases. PLoS One. 5(1):e8972.
Tan YH, et al., (2009) Novel Mutation in c-Cbl Ubiquitin Ligase Gene in Taiwanese Lung Cancer. BioFormosa. 44(1):1-10.
Thien CB, et al. (2001) Cbl: many adaptations to regulate protein tyrosine kinases. Nat Rev Mol Cell Biol. 2(4):294-307.
Thien CB, et al. (2001) RING finger mutations that abolish c-Cbl-directed polyubiquitination and downregulation of the EGF receptor are insufficient for cell transformation. Mol Cell. 7(2):355-365.
Tomioka D, M et al. (2001) Inhibition of growth, invasion, and metastasis of human pancreatic carcinoma cells by NK4 in an orthotopic mouse model. Cancer Res. 61(20):7518-7524.
International Search Report and Written Opinion dated Dec. 14, 2011 for 50. PCT/US2011/039125 filed on Jun. 3, 2011 which published as Dec. 8, 2011 on WO 2011/1534 72 (Inventors—Ravi et al. //Applicant University of Chicago) (13 pages).
International Preliminary Report on Patentability dated Dec. 4, 2012 for PCT/US2011/039125 filed on Jun. 3, 2011 which published as Dec. 8, 2011 on WO 2011/1534 72 (Inventors—Ravi et al. //Applicant University of Chicago) (8 pages).
Tan, et al., "Differential responsiveness of MET inhibition in non-small-cell lung cancer with altered CBL," Scientific Reports, Aug. 23, 2017, pp. 1-13.

* cited by examiner

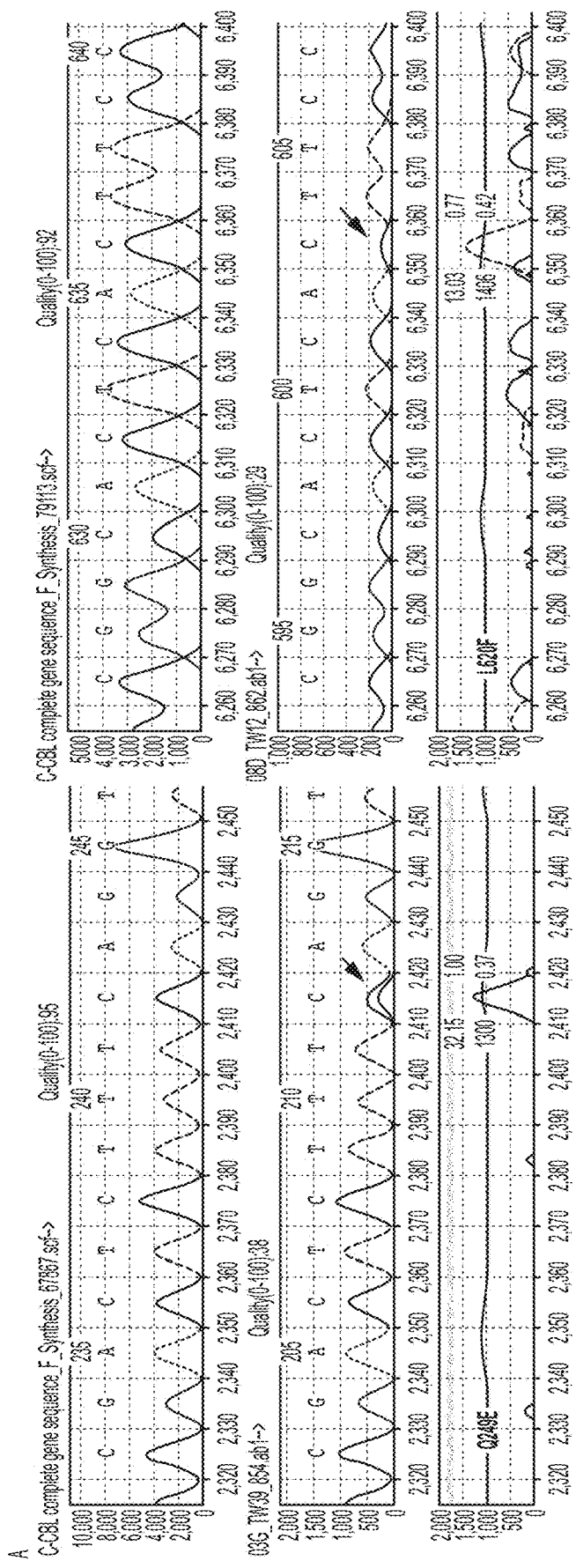
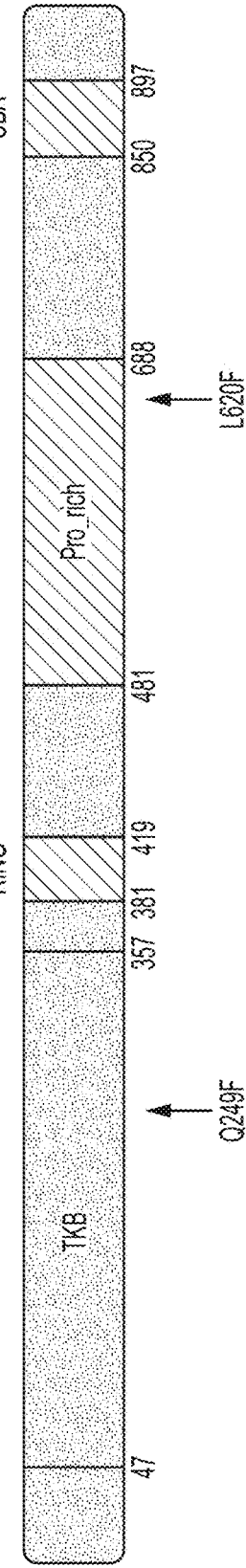
FIG. 1A
FIG. 1B

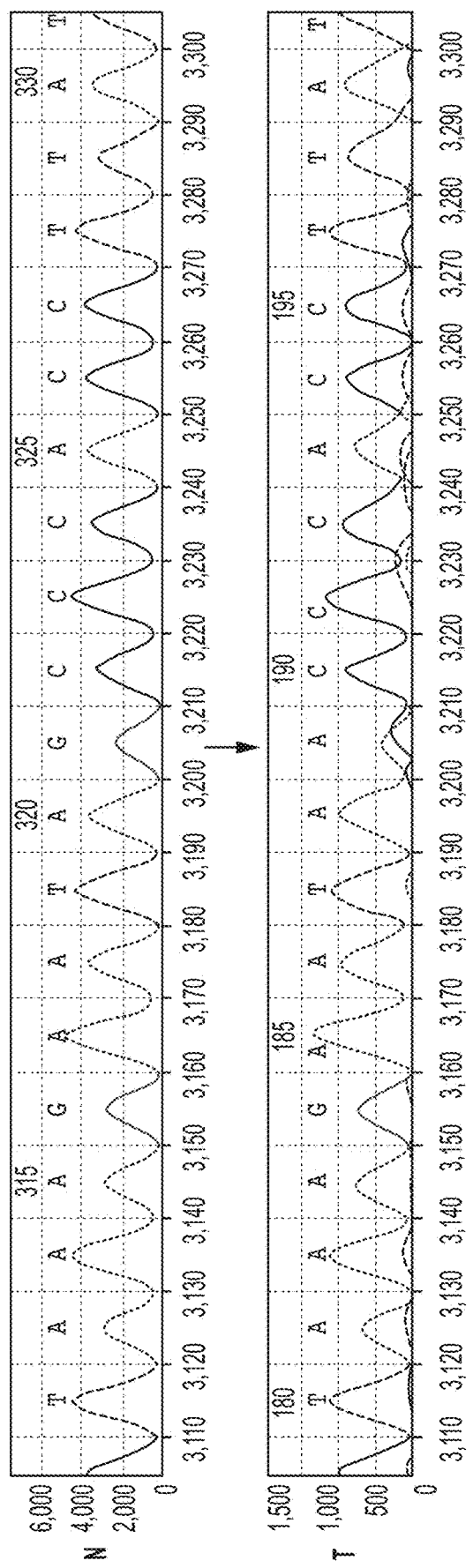
FIG. 5B (top)

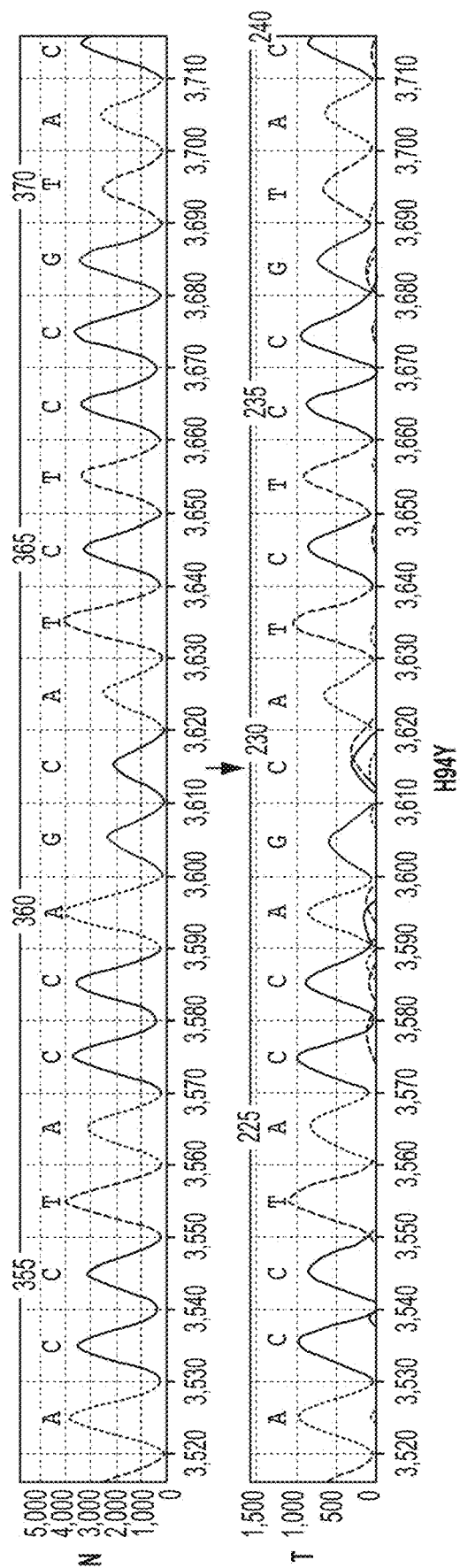
FIG. 5B (upper middle)

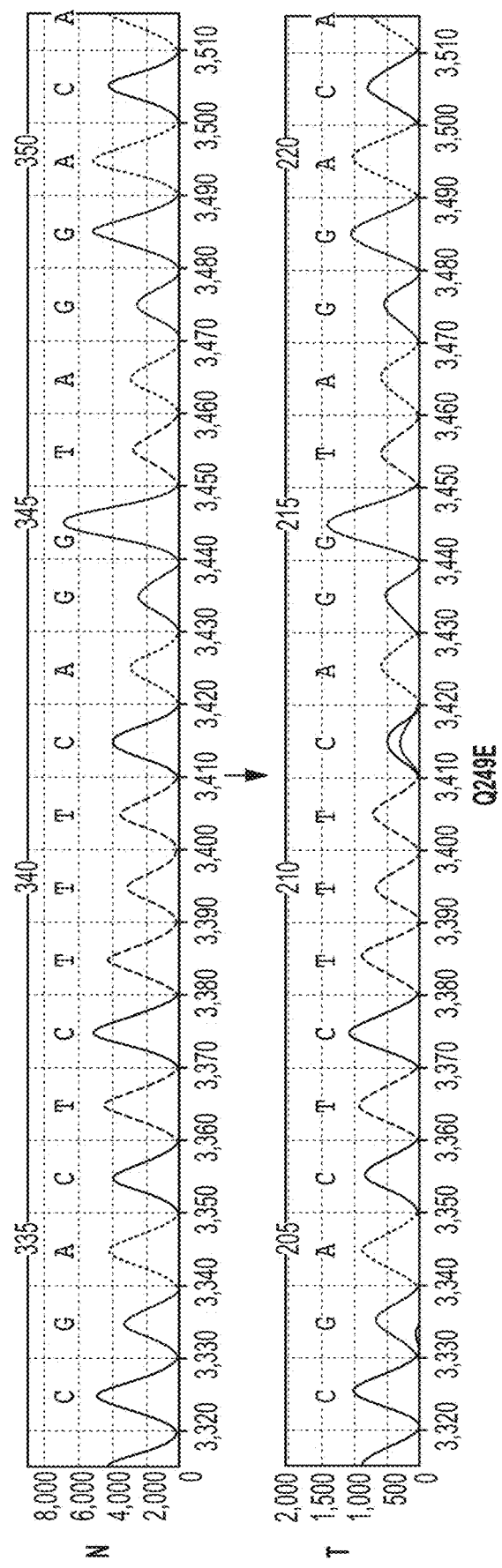
FIG. 5B (lower middle)

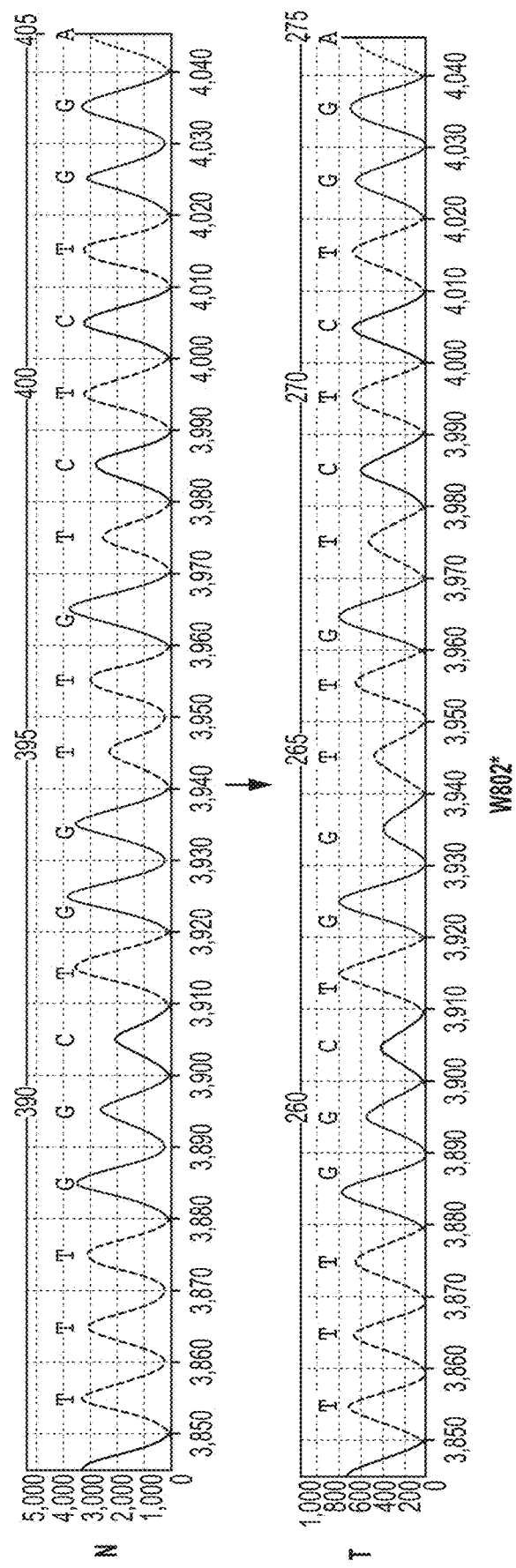
FIG. 5B (lower)

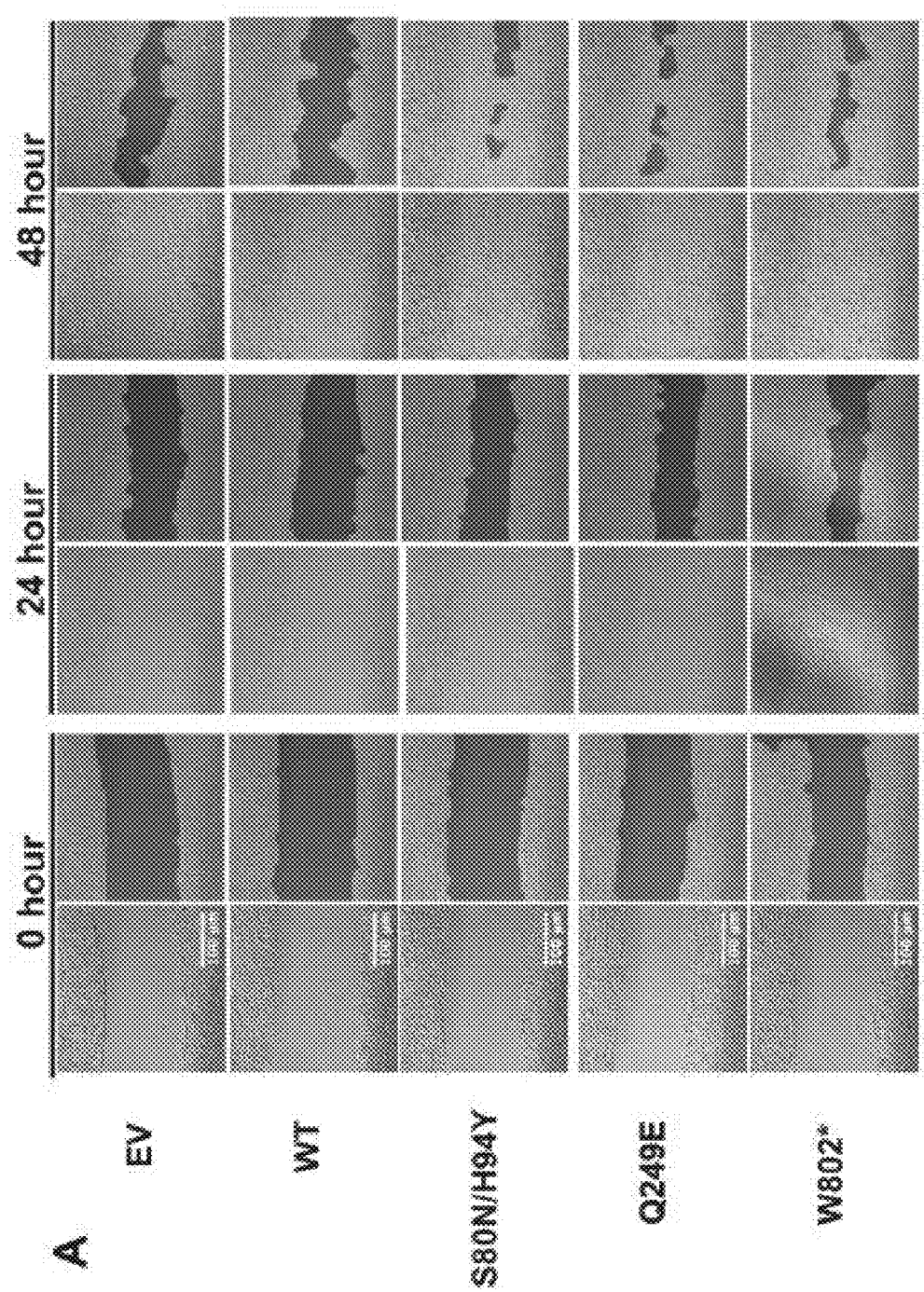

SEQUENCE LISTING

<160> NUMBER OF SEQ ID NOS: 31

<210> SEQ ID NO 1
<211> LENGTH: 2720
<212> TYPE: DNA
<213> ORGANISM: Artificial Sequence
<220> FEATURE:
<223> OTHER INFORMATION: Description of Artificial Sequence: note = synthetic construct

<400> SEQUENCE: 1

| | | | | | | |
|---|---|---|---|---|---|---|
| atggccggca | acgtgaagaa | gagctctggg | gccgggggcg | gcagcggctc | cgggggctcg | 60 |
| ggttcgggtg | gcctgattgg | gctcatgaag | gacgccttcc | agccgcacca | ccaccaccac | 120 |
| caccacctca | gccccaccc | gccggggacg | gtggacaaga | gatggtgga | gaagtgctgg | 180 |
| aagctcatgg | acaaggtggt | gcggttgtgt | cagaacccaa | agctggcgct | aaagaatagc | 240 |
| ccaccttata | tcttagacct | gctaccagat | acctaccagc | atctccgtac | tatcttgtca | 300 |
| agatatgagg | ggaagatgga | gacacttgga | gaaaatgagt | attttagggt | gtttatggag | 360 |
| aatttgatga | agaaaactaa | gcaaaccata | agcctcttca | aggagggaaa | agaaagaatg | 420 |
| tatgaggaga | attctcagcc | taggcgaaac | ctaaccaaac | tgtccctcat | cttcagccac | 480 |
| atgctggcag | aactaaaagg | aatctttcca | agtggactct | tcagggaga | cacatttcgg | 540 |
| attactaaag | cagatgctgc | ggaattttgg | agaaaagctt | ttggggaaaa | gacaatagtc | 600 |
| ccttggaaga | gctttcgaca | ggctctacat | gaagtgcatc | ccatcagttc | tgggctggag | 660 |
| gccatggctc | tgaaatccac | tattgatctg | acctgcaatg | attatatttc | ggttttgaa | 720 |
| tttgacatct | ttacccgact | cttcagccc | tggtcctctt | tgctcaggaa | ttggaacagc | 780 |
| cttgctgtaa | ctcatcctgg | ctacatggct | tttttgacgt | atgacgaagt | gaaagctcgg | 840 |
| ctccagaaat | tcattcacaa | acctggcagt | tatatcttcc | ggctgagctg | tactcgtctg | 900 |
| ggtcagtggg | ctattgggta | tgttactgct | gatgggaaca | ttctccagac | aatccctcac | 960 |
| aataaacctc | tcttccaagc | actgattgat | ggcttcaggg | aaggcttcta | tttgtttcct | 1020 |
| gatggacgaa | atcagaatcc | tgatctgact | ggcttatgtg | aaccaactcc | ccaagaccat | 1080 |
| atcaaagtga | cccaggaaca | atatgaatta | tactgtgaga | tgggctccac | attccaacta | 1140 |
| tgtaaaatat | gtgctgaaaa | tgataaggat | gtaaagattg | agccctgtgg | acacctcatg | 1200 |
| tgcacatcct | gtcttacatc | ctggcaggaa | tcagaaggtc | agggctgtcc | tttctgccga | 1260 |
| tgtgaaatta | aggtactga | acccatcgtg | gtagatccgt | ttgatcctag | agggagtggc | 1320 |
| agcctgttga | ggcaaggagc | agagggagct | ccctccccaa | attatgatga | tgatgatgat | 1380 |
| gaacgagctg | atgatactct | cttcatgatg | aaggaattgg | ctggtgccaa | ggtgaacgg | 1440 |
| ccgccttctc | cattctccat | ggccccacaa | gcttcccttc | ccccggtgcc | accacgactt | 1500 |
| gaccttctgc | cgcagcgagt | atgtgttccc | tcaagtgctt | ctgctcttgg | aactgcttct | 1560 |
| aaggctgctt | ctggctccct | tcataaagac | aaaccattgc | cagtacctcc | cacacttcga | 1620 |
| gatcttccac | caccaccgcc | tccagaccgg | ccatattctg | ttggagcaga | atcccgacct | 1680 |
| caaagacgcc | ccttgccttg | tacaccaggc | gactgtccct | ccagagacaa | actgccccct | 1740 |
| gtcccctcta | gccgcttgg | agactcatgg | ctgccccggc | caatcccaa | agtaccagta | 1800 |
| tctgccccaa | gttccagtga | tccctggaca | ggaagagaat | taaccaaccg | gcactcactt | 1860 |
| ccattttcat | tgccctcaca | aatggagccc | agaccagatg | tgcctaggct | cggaagcacg | 1920 |
| ttcagtctgg | atacctccat | gagtatgaat | agcagcccat | tagtaggtcc | agagtgtgac | 1980 |

```
caccccaaaa tcaaaccttc ctcatctgcc aatgccattt attctctggc tgccagacct    2040
cttcctgtgc caaaactgcc acctggggag caatgtgagg gtgaagagga cacaagtaca    2100
tgactccctc ttccaggcct ctacggcctt tggatacatc ccagagttca cgagcatgtg    2160
attgcgacca gcagattgat agctgtacgt atgaagcaat gtataatatt cagtcccagg    2220
cgccatctat caccgagagc agcacctttg gtgaagggaa tttggccgca gcccatgcca    2280
acactggtcc cgaggagtca gaaaatgagg atgatgggta tgatgtccca aagccacctg    2340
tgccggccgt gctggcccgc cgaactctct cagatatctc taatgccagc tcctcctttg    2400
gctggttgtc tctggatggt gatcctacaa caaatgtcac tgaaggttcc caagttcccg    2460
agaggcctcc aaaaccattc ccgcggagaa tcaactctga acggaaagct ggcagctgtc    2520
agcaaggtag tggtcctgcc gcctctgctg ccaccgcctc acctcagctc tccagtgaga    2580
tcgagaacct catgagtcag gggtactcct accaggacat ccagaaagct ttggtcattg    2640
cccagaacaa catcgagatg gccaaaaaca tcctccggga atttgtttcc atttcttctc    2700
ctgcccatgt agctacctag                                                2720

<210> SEQ ID NO 2
<211> LENGTH: 906
<212> TYPE: PRT
<213> ORGANISM: Artificial Sequence
<220> FEATURE:
<223> OTHER INFORMATION: Description of Artificial Sequence: note =
      synthetic construct

<400> SEQUENCE: 2

Met Ala Gly Asn Val Lys Lys Ser Ser Gly Ala Gly Gly Gly Ser Gly
1               5                   10                  15

Ser Gly Gly Ser Gly Ser Gly Gly Leu Ile Gly Leu Met Lys Asp Ala
            20                  25                  30

Phe Gln Pro His His His His His His Leu Ser Pro His Pro Pro
        35                  40                  45

Gly Thr Val Asp Lys Lys Met Val Glu Lys Cys Trp Lys Leu Met Asp
    50                  55                  60

Lys Val Val Arg Leu Cys Gln Asn Pro Lys Leu Ala Leu Lys Asn Ser
65                  70                  75                  80

Pro Pro Tyr Ile Leu Asp Leu Leu Pro Asp Thr Tyr Gln His Leu Arg
                85                  90                  95

Thr Ile Leu Ser Arg Tyr Glu Gly Lys Met Glu Thr Leu Gly Glu Asn
            100                 105                 110

Glu Tyr Phe Arg Val Phe Met Glu Asn Leu Met Lys Lys Thr Lys Gln
        115                 120                 125

Thr Ile Ser Leu Phe Lys Glu Gly Lys Glu Arg Met Tyr Glu Glu Asn
    130                 135                 140

Ser Gln Pro Arg Arg Asn Leu Thr Lys Leu Ser Leu Ile Phe Ser His
145                 150                 155                 160

Met Leu Ala Glu Leu Lys Gly Ile Phe Pro Ser Gly Leu Phe Gln Gly
                165                 170                 175

Asp Thr Phe Arg Ile Thr Lys Ala Asp Ala Ala Glu Phe Trp Arg Lys
            180                 185                 190

Ala Phe Gly Glu Lys Thr Ile Val Pro Trp Lys Ser Phe Arg Gln Ala
        195                 200                 205

Leu His Glu Val His Pro Ile Ser Ser Gly Leu Glu Ala Met Ala Leu
    210                 215                 220
```

```
Lys Ser Thr Ile Asp Leu Thr Cys Asn Asp Tyr Ile Ser Val Phe Glu
225                 230                 235                 240

Phe Asp Ile Phe Thr Arg Leu Phe Gln Pro Trp Ser Ser Leu Leu Arg
            245                 250                 255

Asn Trp Asn Ser Leu Ala Val Thr His Pro Gly Tyr Met Ala Phe Leu
        260                 265                 270

Thr Tyr Asp Glu Val Lys Ala Arg Leu Gln Lys Phe Ile His Lys Pro
    275                 280                 285

Gly Ser Tyr Ile Phe Arg Leu Ser Cys Thr Arg Leu Gly Gln Trp Ala
290                 295                 300

Ile Gly Tyr Val Thr Ala Asp Gly Asn Ile Leu Gln Thr Ile Pro His
305                 310                 315                 320

Asn Lys Pro Leu Phe Gln Ala Leu Ile Asp Gly Phe Arg Glu Gly Phe
            325                 330                 335

Tyr Leu Phe Pro Asp Gly Arg Asn Gln Asn Pro Asp Leu Thr Gly Leu
        340                 345                 350

Cys Glu Pro Thr Pro Gln Asp His Ile Lys Val Thr Gln Glu Gln Tyr
    355                 360                 365

Glu Leu Tyr Cys Glu Met Gly Ser Thr Phe Gln Leu Cys Lys Ile Cys
370                 375                 380

Ala Glu Asn Asp Lys Asp Val Lys Ile Glu Pro Cys Gly His Leu Met
385                 390                 395                 400

Cys Thr Ser Cys Leu Thr Ser Trp Gln Glu Ser Glu Gly Gln Gly Cys
            405                 410                 415

Pro Phe Cys Arg Cys Glu Ile Lys Gly Thr Glu Pro Ile Val Val Asp
        420                 425                 430

Pro Phe Asp Pro Arg Gly Ser Gly Ser Leu Leu Arg Gln Gly Ala Glu
    435                 440                 445

Gly Ala Pro Ser Pro Asn Tyr Asp Asp Asp Asp Glu Arg Ala Asp
450                 455                 460

Asp Thr Leu Phe Met Met Lys Glu Leu Ala Gly Ala Lys Val Glu Arg
465                 470                 475                 480

Pro Pro Ser Pro Phe Ser Met Ala Pro Gln Ala Ser Leu Pro Pro Val
            485                 490                 495

Pro Pro Arg Leu Asp Leu Leu Pro Gln Arg Val Cys Val Pro Ser Ser
        500                 505                 510

Ala Ser Ala Leu Gly Thr Ala Ser Lys Ala Ala Ser Gly Ser Leu His
    515                 520                 525

Lys Asp Lys Pro Leu Pro Val Pro Pro Thr Leu Arg Asp Leu Pro Pro
530                 535                 540

Pro Pro Pro Pro Asp Arg Pro Tyr Ser Val Gly Ala Glu Ser Arg Pro
545                 550                 555                 560

Gln Arg Arg Pro Leu Pro Cys Thr Pro Gly Asp Cys Pro Ser Arg Asp
            565                 570                 575

Lys Leu Pro Pro Val Pro Ser Ser Arg Leu Gly Asp Ser Trp Leu Pro
        580                 585                 590

Arg Pro Ile Pro Lys Val Pro Val Ser Ala Pro Ser Ser Ser Asp Pro
    595                 600                 605

Trp Thr Gly Arg Glu Leu Thr Asn Arg His Ser Leu Pro Phe Ser Leu
610                 615                 620

Pro Ser Gln Met Glu Pro Arg Pro Asp Val Pro Arg Leu Gly Ser Thr
625                 630                 635                 640

Phe Ser Leu Asp Thr Ser Met Ser Met Asn Ser Ser Pro Leu Val Gly
```

```
            645                 650                 655
Pro Glu Cys Asp His Pro Lys Ile Lys Pro Ser Ser Ser Ala Asn Ala
            660                 665                 670

Ile Tyr Ser Leu Ala Ala Arg Pro Leu Pro Val Pro Lys Leu Pro Pro
            675                 680                 685

Gly Glu Gln Cys Glu Gly Glu Asp Thr Glu Tyr Met Thr Pro Ser
    690                 695                 700

Ser Arg Pro Leu Arg Pro Leu Asp Thr Ser Gln Ser Ser Arg Ala Cys
705                 710                 715                 720

Asp Cys Asp Gln Gln Ile Asp Ser Cys Thr Tyr Glu Ala Met Tyr Asn
                725                 730                 735

Ile Gln Ser Gln Ala Pro Ser Ile Thr Glu Ser Ser Thr Phe Gly Glu
            740                 745                 750

Gly Asn Leu Ala Ala Ala His Ala Asn Thr Gly Pro Glu Glu Ser Glu
            755                 760                 765

Asn Glu Asp Asp Gly Tyr Asp Val Pro Lys Pro Pro Val Pro Ala Val
    770                 775                 780

Leu Ala Arg Arg Thr Leu Ser Asp Ile Ser Asn Ala Ser Ser Ser Phe
785                 790                 795                 800

Gly Trp Leu Ser Leu Asp Gly Asp Pro Thr Thr Asn Val Thr Glu Gly
                805                 810                 815

Ser Gln Val Pro Glu Arg Pro Pro Lys Pro Phe Pro Arg Arg Ile Asn
            820                 825                 830

Ser Glu Arg Lys Ala Gly Ser Cys Gln Gln Gly Ser Gly Pro Ala Ala
            835                 840                 845

Ser Ala Ala Thr Ala Ser Pro Gln Leu Ser Ser Glu Ile Glu Asn Leu
    850                 855                 860

Met Ser Gln Gly Tyr Ser Tyr Gln Asp Ile Gln Lys Ala Leu Val Ile
865                 870                 875                 880

Ala Gln Asn Asn Ile Glu Met Ala Lys Asn Ile Leu Arg Glu Phe Val
                885                 890                 895

Ser Ile Ser Ser Pro Ala His Val Ala Thr
            900                 905

<210> SEQ ID NO 3
<211> LENGTH: 24
<212> TYPE: DNA
<213> ORGANISM: Artificial Sequence
<220> FEATURE:
<223> OTHER INFORMATION: Description of Artificial Sequence: note =
      synthetic construct

<400> SEQUENCE: 3
taaaatggtt gcctgtgggc aatg                                          24

<210> SEQ ID NO 4
<211> LENGTH: 24
<212> TYPE: DNA
<213> ORGANISM: Artificial Sequence
<220> FEATURE:
<223> OTHER INFORMATION: Description of Artificial Sequence: note =
      synthetic construct

<400> SEQUENCE: 4
catcttgtat ggtgaatttg gtgc                                          24

<210> SEQ ID NO 5
<211> LENGTH: 21
```

```
<212> TYPE: DNA
<213> ORGANISM: Artificial Sequence
<220> FEATURE:
<223> OTHER INFORMATION: Description of Artificial Sequence: note =
      synthetic construct

<400> SEQUENCE: 5
gcttaatgtg gctctccttc c                                                  21

<210> SEQ ID NO 6
<211> LENGTH: 24
<212> TYPE: DNA
<213> ORGANISM: Artificial Sequence
<220> FEATURE:
<223> OTHER INFORMATION: Description of Artificial Sequence: note =
      synthetic construct

<400> SEQUENCE: 6
ctctgagttg gttgtacatc tgac                                               24

<210> SEQ ID NO 7
<211> LENGTH: 22
<212> TYPE: DNA
<213> ORGANISM: Artificial Sequence
<220> FEATURE:
<223> OTHER INFORMATION: Description of Artificial Sequence: note =
      synthetic construct

<400> SEQUENCE: 7
gtctgtatct tgccttgcct tc                                                 22

<210> SEQ ID NO 8
<211> LENGTH: 23
<212> TYPE: DNA
<213> ORGANISM: Artificial Sequence
<220> FEATURE:
<223> OTHER INFORMATION: Description of Artificial Sequence: note =
      synthetic construct

<400> SEQUENCE: 8
ggacccagac tagatgcttt ctg                                                23

<210> SEQ ID NO 9
<211> LENGTH: 30
<212> TYPE: DNA
<213> ORGANISM: Artificial Sequence
<220> FEATURE:
<223> OTHER INFORMATION: Description of Artificial Sequence: note =
      synthetic construct

<400> SEQUENCE: 9
cggtattata tagcctttac tgatacaagg                                         30

<210> SEQ ID NO 10
<211> LENGTH: 22
<212> TYPE: DNA
<213> ORGANISM: Artificial Sequence
<220> FEATURE:
<223> OTHER INFORMATION: Description of Artificial Sequence: note =
      synthetic construct

<400> SEQUENCE: 10
cctaggtctg gcccatttgt ag                                                 22

<210> SEQ ID NO 11
<211> LENGTH: 21
<212> TYPE: DNA
```

```
<213> ORGANISM: Artificial Sequence
<220> FEATURE:
<223> OTHER INFORMATION: Description of Artificial Sequence: note =
      synthetic construct

<400> SEQUENCE: 11
cagaggctca gctgtggtaa g                                              21

<210> SEQ ID NO 12
<211> LENGTH: 26
<212> TYPE: DNA
<213> ORGANISM: Artificial Sequence
<220> FEATURE:
<223> OTHER INFORMATION: Description of Artificial Sequence: note =
      synthetic construct

<400> SEQUENCE: 12
gctctgttca atttgagtta tgtctg                                         26

<210> SEQ ID NO 13
<211> LENGTH: 21
<212> TYPE: DNA
<213> ORGANISM: Artificial Sequence
<220> FEATURE:
<223> OTHER INFORMATION: Description of Artificial Sequence: note =
      synthetic construct

<400> SEQUENCE: 13
gttggcccac agtagacaat c                                              21

<210> SEQ ID NO 14
<211> LENGTH: 24
<212> TYPE: DNA
<213> ORGANISM: Artificial Sequence
<220> FEATURE:
<223> OTHER INFORMATION: Description of Artificial Sequence: note =
      synthetic construct

<400> SEQUENCE: 14
cttgtgactg aagagcacat gtac                                           24

<210> SEQ ID NO 15
<211> LENGTH: 22
<212> TYPE: DNA
<213> ORGANISM: Artificial Sequence
<220> FEATURE:
<223> OTHER INFORMATION: Description of Artificial Sequence: note =
      synthetic construct

<400> SEQUENCE: 15
tgtgttaccc attcaggcac tc                                             22

<210> SEQ ID NO 16
<211> LENGTH: 24
<212> TYPE: DNA
<213> ORGANISM: Artificial Sequence
<220> FEATURE:
<223> OTHER INFORMATION: Description of Artificial Sequence: note =
      synthetic construct

<400> SEQUENCE: 16
gactccgtct caaaaagaaa ccac                                           24

<210> SEQ ID NO 17
<211> LENGTH: 22
<212> TYPE: DNA
<213> ORGANISM: Artificial Sequence
```

```
<220> FEATURE:
<223> OTHER INFORMATION: Description of Artificial Sequence: note =
      synthetic construct

<400> SEQUENCE: 17
gtgaggagaa gaaagcagtt gg                                               22

<210> SEQ ID NO 18
<211> LENGTH: 23
<212> TYPE: DNA
<213> ORGANISM: Artificial Sequence
<220> FEATURE:
<223> OTHER INFORMATION: Description of Artificial Sequence: note =
      synthetic construct

<400> SEQUENCE: 18
cagaaccttg gctattgcga aac                                              23

<210> SEQ ID NO 19
<211> LENGTH: 26
<212> TYPE: DNA
<213> ORGANISM: Artificial Sequence
<220> FEATURE:
<223> OTHER INFORMATION: Description of Artificial Sequence: note =
      synthetic construct

<400> SEQUENCE: 19
cctaagttcc cagactctaa cagatg                                           26

<210> SEQ ID NO 20
<211> LENGTH: 29
<212> TYPE: DNA
<213> ORGANISM: Artificial Sequence
<220> FEATURE:
<223> OTHER INFORMATION: Description of Artificial Sequence: note =
      synthetic construct

<400> SEQUENCE: 20
ccttgtatca gtaaaggcta tataatacc                                        29

<210> SEQ ID NO 21
<211> LENGTH: 25
<212> TYPE: DNA
<213> ORGANISM: Artificial Sequence
<220> FEATURE:
<223> OTHER INFORMATION: Description of Artificial Sequence: note =
      synthetic construct

<400> SEQUENCE: 21
ccagtctcct aaactgccat cttac                                            25

<210> SEQ ID NO 22
<211> LENGTH: 25
<212> TYPE: DNA
<213> ORGANISM: Artificial Sequence
<220> FEATURE:
<223> OTHER INFORMATION: Description of Artificial Sequence: note =
      synthetic construct

<400> SEQUENCE: 22
ctggcccaca catatttctt aacag                                            25

<210> SEQ ID NO 23
<211> LENGTH: 23
<212> TYPE: DNA
<213> ORGANISM: Artificial Sequence
<220> FEATURE:
```

<223> OTHER INFORMATION: Description of Artificial Sequence: note = 
      synthetic construct

<400> SEQUENCE: 23
cagagcaatg aaacagatgg cag                                          23

<210> SEQ ID NO 24
<211> LENGTH: 26
<212> TYPE: DNA
<213> ORGANISM: Artificial Sequence
<220> FEATURE:
<223> OTHER INFORMATION: Description of Artificial Sequence: note = 
      synthetic construct

<400> SEQUENCE: 24
gcttagatca agctatctca attgcc                                       26

<210> SEQ ID NO 25
<211> LENGTH: 25
<212> TYPE: DNA
<213> ORGANISM: Artificial Sequence
<220> FEATURE:
<223> OTHER INFORMATION: Description of Artificial Sequence: note = 
      synthetic construct

<400> SEQUENCE: 25
cttgggactt tcctcccatt tagac                                        25

<210> SEQ ID NO 26
<211> LENGTH: 25
<212> TYPE: DNA
<213> ORGANISM: Artificial Sequence
<220> FEATURE:
<223> OTHER INFORMATION: Description of Artificial Sequence: note = 
      synthetic construct

<400> SEQUENCE: 26
ctaggtgcca cttgagtaat aactc                                        25

<210> SEQ ID NO 27
<211> LENGTH: 37
<212> TYPE: DNA
<213> ORGANISM: Artificial Sequence
<220> FEATURE:
<223> OTHER INFORMATION: Description of Artificial Sequence: note = 
      synthetic construct

<400> SEQUENCE: 27
gctggcgcta aagaataacc caccttatat cttagac                           37

<210> SEQ ID NO 28
<211> LENGTH: 38
<212> TYPE: DNA
<213> ORGANISM: Artificial Sequence
<220> FEATURE:
<223> OTHER INFORMATION: Description of Artificial Sequence: note = 
      synthetic construct

<400> SEQUENCE: 28
ctaccagata cctaccagta tctccgtact atcttgtc                          38

<210> SEQ ID NO 29
<211> LENGTH: 35
<212> TYPE: DNA
<213> ORGANISM: Artificial Sequence
<220> FEATURE:
<223> OTHER INFORMATION: Description of Artificial Sequence: note =

```
                          synthetic construct

<400> SEQUENCE: 29
ctttacccga ctctttgagc cctggtcctc tttgc                              35

<210> SEQ ID NO 30
<211> LENGTH: 37
<212> TYPE: DNA
<213> ORGANISM: Artificial Sequence
<220> FEATURE:
<223> OTHER INFORMATION: Description of Artificial Sequence: note =
      synthetic construct

<400> SEQUENCE: 30
agctcctcct ttggctgatt gtctctggat ggtgatc                            37

<210> SEQ ID NO 31
<211> LENGTH: 35
<212> TYPE: DNA
<213> ORGANISM: Artificial Sequence
<220> FEATURE:
<223> OTHER INFORMATION: Description of Artificial Sequence: note =
      synthetic construct

<400> SEQUENCE: 31
ctttacccga ctctttgagc cctggtcctc tttgc                              35
```

C-CBL MUTATIONS AND USES THEREOF

CROSS-REFERENCE TO RELATED APPLICATIONS

This application claims priority to and is a Continuation of U.S. application Ser. No. 15/077,409, filed Mar. 22, 2016, which is a Continuation of U.S. application Ser. No. 13/701, 569, filed Apr. 29, 2013, which claims priority to International Application PCT/US2011/39125, filed Jun. 3, 2011, which claims benefit of U.S. Provisional Application No. 61/351,501, filed Jun. 4, 2010, all of which are hereby incorporated herein by reference in their entireties.

REFERENCE TO SEQUENCE LISTING

This application includes a Sequence Listing as a text file named "Sequence Listing for 096487-1089928-000430US.txt" created May 21, 2018, and containing 18,889 bytes. The material contained in this text file is incorporated by reference in its entirety for all purposes.

BACKGROUND

Lung cancer is the second most common cancer in both men and women (after prostate and breast cancer, respectively), accounting for approximately 15% of all new cancers. About 80% of all lung cancers are non-small cell lung cancers (NSCLC's), which can be further divided into distinct groups: adenocarcinoma (bronchioalveolar carcinoma as a subset), squamous cell carcinoma, and large cell carcinoma (Jemal, A. et al., Cancer statistics, 2009 July-August; 59(4):225-49). It is estimated that in 2009, there will be about 219,440 new cases of lung cancer. The prognosis for NSCLC is relatively poor and a disproportionately greater percentage of people die due to lung cancer than prostate, breast, and colon cancers combined. Only 15% of NSCLC patients are expected to survive 5 years or more, whereas the prognosis for small cell lung cancer (SCLC) is much worse. African American males have a 40% higher chance of developing lung cancer than their Caucasian counterparts (Abidoye, O. et al. Nat Clin Pract Oncol. 2007 February; 4(2): 118-29). Additionally, they also suffer from much higher morbidity and mortality from this disease. Given the incidence of NSCLC and its ethnic disparity and poor prognosis, there is clearly an urgent need to identify and develop novel targeted therapies that are especially directed at the African American patient population. Gender differences are also striking, with women having significantly better prognosis as compared to men. There are a number of genetic alterations that can occur in lung cancer. As an example, in NSCLC, mutations in KRAS, p53, EGFR and MET have been identified. Many of the pathways that involve these genes and their corresponding proteins, especially Receptor Tyrosine Kinases (RTKs), are controlled by c-CBL.

CBL (Casitas B-lineage lymphoma) is a mammalian gene located on human chromosome 11q23.3.), and its protein product is involved in cell signaling and protein ubiquitination (Swaminathan, G. et al., 2006). CBL proteins belong to the RING finger class of ubiquitin ligases (E3) and there are three homologues: c-CBL, CBL-b, CBL-3. The c-CBL and CBL-b genes are ubiquitously expressed with the highest levels in hematopoietic tissues (Kozlov G, et al. 2007). c-CBL consists of four regions encoding for functionally distinct protein domains: the N-terminal tyrosine kinase binding (TKB) domain, the linker region, the catalytic RING finger domain, the proline-rich region and the c-terminal ubiquitin-associated (UBA) domain that also overlaps with a leucine-zipper (LZ) domain (Swaminathan G, and Tsygankov A Y. (2006) J Cell Physiol 209:21-43). Both TKB and RING finger domains are essential for ligand-induced ubiquitination of RTKs (Lill N L, et al. 2000). The evolutionarily conserved N-terminal region of CBL is sufficient to enhance down-regulation of the epidermal growth factor receptor (Miyake S, et al., J Biol Chem 275:367-377 (1999)). It is the RING finger of c-CBL that mediates desensitization of the epidermal growth factor receptor. RING finger mutations can abolish c-CBL-directed polyubiquitination and downregulation of the EGF receptor, but these are insufficient for cell transformation (Waterman H, et al., Mol Cell 7:355-365; (1999)). The TKB domain includes four-helix bundle (4H), a calcium-biding EF hand, and a modified SH2 domain, which binds to phosphotyrosine residues.

The CBL family, especially c-CBL, has been recognized as a key player in the negative regulation of antigen receptor and other signaling pathways. (Swaminathan and Tsygankov, 2006). In addition, c-CBL has been pointed out as a regulator of RTKs (Thien C B, and Langdon W Y. 2001. Nat Rev Mol Cell Biol 2:294-307), with many studies indicating that c-CBL plays an important role in downregulation of RTKs such as c-Met and epidermal growth factor receptor (EGFR) through its E3 ubiquitin ligase activity. (Pennock S. and Wang Z. 2008. Mol Cell Biol. 28(9):3020-37).

c-Met is a RTK, which stimulates the invasive growth of carcinoma cells, and is tumorigenetically mutated and overexpressed in many solid tumors. Overexpression of c-Met has been shown in small cell lung cancer (SCLC) and non-small cell lung cancer (NSCLC) cells. In addition, studies have identified C-Met mutations located in specific domain, e.g. the juxtamembrane domain, which results in the loss of c-CBL E3-ligase binding.

EGFR, a member of the ErbB family, is important in the regulation of cell growth, differentiation and survival. EGFR overexpression is detected in various types of malignant tumors; thus, EGFR is a promising therapeutic target. Mutations in the EGFR kinase domain are associated with clinical response to EGFR inhibitors and are observed frequently in NSCLC patients in East Asian populations.

As is the case with other cancers, lung cancers are also addicted to a variety of oncogenes and growth factors. EGFR is one of the best-studied RTKs in the context of NSCLC. EGFR frequently becomes overexpressed in NSCLC and can acquire gain-of-function mutations, and importantly both of these events can occur concurrently. The above modifications confer growth and invasive advantages to lung tumors. Another RTK that is overexpressed and frequently acquires gain-of-function mutations is c-MET. More than EGFR, c-MET promotes cell motility and migration, thereby contributing significantly to metastasis. In addition to the c-MET receptor, its natural ligand hepatocyte growth factor (HGF) is also frequently overexpressed (10 to 100 fold higher) in lung cancers compared to adjacent normal tissue. Higher levels of HGF are associated with more aggressive tumor biology and a poorer prognosis in NSCLC. The HGF/c-MET autocrine loop plays a vital role in the epithelial mesenchymal transition (EMT) that underlies the metastasis process.

In a normal cell, the steady state level of any RTK is the net balance between synthesis and degradation. The synthesis of EGFR and c-MET in NSCLC is generally boosted by aberrant gene amplification. Although the frequent mutations seen in the kinase domains of EGFR and c-MET are known to contribute to increased tyrosine kinase activity, mutations in the juxtamembrane region, especially in c-MET, result in loss of negative regulation. The functionality of RTKs is known to be downregulated in normal cells through ubiquitination-mediated proteasomal degradation. Most of the RTKs such as EGFR, c-MET, KIT and IGFR are negatively regulated by a specific E3 ubiquitin ligase: c-CBL.

c-CBL also binds to EGFR and acts as the E3 that targets EGFR for ubiquitination and degradation, thereby desensitizing EGF signaling and opposing induced by EGF-induced cellular proliferation. EGF activation also appears to activate the tyrosine kinase SRC, which phosphorylates c-CBL and in turn activates the ubiquitination and degradation of EGFR. Specifically, initial binding of c-CBL to EGFR is either by direct association between the tyrosine phosphorylated receptor and c-CBL TK domain, or it is facilitated by the adaptor Grb2. The SH2 domain of Grb2 binds to the phosphorylated receptor and the SH3 region interacts with proline-rich region of c-CBL. EGFR mediated tyrosine phosphorylation of c-CBL results in activation of the ligase and mediates multi-monoubiquitylation of the K48 residues. This triggers the 'destruction sequence' starting with endocytosis of EGFR through clathrin-coated pits. CIN85 provides the link between the c-CBL/EGFR complex and the endocytic protein endophilin. The trafficking of the receptor to the lysosome culminates in its degradation. In contrast, non-ubiquitinated receptors are effectively internalized, and recycled back to the plasma membrane. A similar 'destruction sequence' and recycling process have been reported for MET. In short, activation of EGFR or MET by ligand binding under physiological conditions results in recruitment of the c-CBL ubiquitin ligase in conjunction with an E2 ubiquitin-conjugating enzyme. More detailed studies have demonstrated that c-CBL mediates monoubiquitinaton or polyubiquitination of receptors and initiates receptor endocytosis. Receptor bound c-CBL also recruits CIN-85/endophilin-A1 complexes to the plasma membrane which is necessary for invagination and formation of endocytic vesicles.

A recent study shows that defective endocytosis of EGFR is characterized by a deletion mutant and the point mutation L858R, whereby its association with c-CBL and subsequent ubiquitination are impaired. Recently, the first human c-CBL mutations were reported in acute myeloid leukemia (AML) patients.

Not only can E3 activity be important in oncogenesis, c-CBL has a dual but separate function as a signal transduction molecule. c-CBL has previously been shown to be important in binding CRKL and BCR/ABL in hematopoietic cells. Also, it can bind and modulate functions of cytoskeleton by binding to proteins like talin and paxillin. The TKB domain is important in binding to a number of molecules that function in signal transduction.

As described above, c-Met also plays a role in the development and progression of cancer and represents a therapeutic target. Unlike imatinib for CML (targeting Bcr/Abl) and gastrointestinal stromal tumors (GIST; targeting c-Kit), targeted small molecule inhibitors against c-Met have yet to be approved for use in humans. Several c-Met inhibitors are currently in clinical development. Also an antagonist of HGF, NK4, was previously reported to be generated by proteolytic digestion of HGF (Date, et al., FEBS Lett, 420, (1), 1-6 (1997)). NK4 is a truncated HGF composed of the NH2-terminal hairpin domain and four kringle domains in the alpha-chain of HGF. It retains c-Met receptor binding properties without mediating biological responses. NK4 antagonizes HGF-induced tyrosine phosphorylation of c-Met, resulting in inhibition of HGF-induced motility, angiogenesis and invasion of HT115 human colorectal cancer cells (Parr, et al., Int J Cancer, 85, (4), 563-70 (2000)). Also, when administered to pancreatic tumor-bearing mice, NK4 inhibited growth, invasion, and disseminating metastasis of pancreatic cancer cells, and prolonged the lifespan of these mice (Tomioka, et al., Cancer Res, 61, (20), 7518-24 (2001)). Finally, a soluble chimeric form of c-Met was shown to retain full capacity to bind HGF and therefore neutralize HGF activity Mark, et al., J Biol Chem, 267, (36), 26166-71 (1992)). NK4, pro-HGF (uncleavable HGF) and the decoy c-Met receptor have been shown to inhibit mutant c-Met-induced transformation of NIH3T3 cells (Michieli, et al., Oncogene, 18, (37), 5221-31 (1999)).

Small molecule inhibitors directed specifically against c-Met represent an attractive therapeutic approach. The effectiveness of a novel specific small molecule inhibitor of c-Met, SU11274 was first reported by Sattler, et at. (Pfizer; previously Sugen), in cells transformed by the oncogenic Tpr-Met as a model, as well as in SCLC (Sattler, et al., Cancer Res, 63, (17), 5462-9 (2003)). Inhibition of the Met kinase activity by the drug SU11274 led to time- and dose-dependent reduced cell growth and induced G1 cell cycle arrest and apoptosis (Ma, et al., Cancer Res, 65, (4), 1479-88 (2005)). Met kinase autophosphorylation was reduced on sites that have been previously shown to be important for activation of pathways involved in cell growth and survival, especially the phosphatidylinositol-3'-kinase (PI3K) and the Ras pathway. The characterization of SU11274 as an effective inhibitor of Met tyrosine kinase activity illustrates the therapeutic potential of targeting Met in cancers associated with activated forms of this kinase.

To impact on this disease, newer and novel targeted therapies need to be employed. However, it still remains to be seen how and if patients respond to such inhibitors.

Even with the best therapies and recent advent of novel molecularly targeted therapies, overall survival for all Non-Small Cell Lung Cancer (NSCLC) patients is only 15% over a five year period. Receptor tyrosine kinases (RTKs) have shown to be important in a variety of malignancies, such as c-Kit in GISTs and epidermal growth factor receptor (EGFR) in NSCLC. However, the response to EGFR blockade by small molecule inhibitors, such as erlotinib, is at best 5-15% in refractory advanced NSCLC. The compositions and methods disclosed herein will provide a means to address such issues.

Head and neck squamous cell carcinoma (HNSCC) is a heterogenous group of disorders in which RTKs such as EGFR and MET are overexpressed. c-CBL is involved in the degradation of receptor tyrosine kinases via targeting for lysosomal-mediated degradation in HNSCC. c-CBL protein expression is largely reduced or absent in HNSCC patient tumor specimens, and this was correlated with increased expression of MET. This pattern of c-CBL and MET protein expression is largely recapitulated in HNSCC cell lines. In HNSCC tumor specimens, c-CBL was found to be mutated, and LOH was detected at the c-CBL locus. Additionally, MET is activated in HNSCC, and pMET expression is concomitant with MET expression. These data support the notion that diminished c-CBL expression in HNSCC is related to the increased expression of MET. In certain hematologic malignancies c-CBL has Uniparental Disomy with activating c-CBL mutations. The relative low expression level of c-CBL implicates this molecule as a tumor suppressor in HNSCC; whereas in other tumors it likely functions as an adaptor molecule, in which case it has been shown previously that BCR/ABL utilizes c-CBL for a plethora of signal transduction. In cell culture models of HNSCC in which c-CBL was knocked down using targeted siRNA, MET expression was increased and cell viability was decreased. MET is largely overexpressed in HNSCC, and it can be effectively targeted using small molecule chemical inhibitors.

All references cited herein, including patent applications and publications, are incorporated by reference in their entirety.

Additional advantages of the invention will be set forth in part in the description which follows, and in part will be obvious from the description, or may be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this specification, illustrate several embodiments of the invention and together with the description, serve to explain the principles of the invention. These are non-limiting examples.

FIGS. 1A and 1B show c-CBL mutations. FIG. 1A shows chromatograms indicating the location of two exon mutations that were analyzed as described in Example 1. The chromatograms showed the patient with somatic mutation Q249E had nucleotide C>CA changes and the patient with SNP L620F had nucleotide C>CT changes. The arrows indicate the changed nucleotide sites. FIG. 1B shows the c-CBL domain structure that was analyzed during the experimental example of FIG. 1A. As depicted in FIG. 1B, c-CBL has N-terminal tyrosine kinase binding (TKB) domain, RING finger domain, proline rich (Pro_rich) region, and C-terminal ubiquitin-associated (UBA) domain. The mutations Q249E and L620F are located on TKB domain and Pro_rich region, respectively.

FIG. 5A is a schematic illustration of various c-CBL mutants with respect to the different functional domains that were analyzed as described in Example 2. Three mutations: S80N, H94Y, Q249E were located on the TKB domain; V391I was located on the RING finger domain; 72515_72517 del ATG (a non-frameshift deletion) and L620F (a known SNP, rs2227988) were located on Pro-rich region, and W802*, R830K, and A848T were found in the C-terminal region of c-CBL. The numbers shown represent amino acid positions. Association of c-CBL mutations among different ethnic populations is shown in the table in FIG. 5A. FIG. 5B depicts representative examples of sequencing chromatograms of the mutation region in normal (N) and tumor (T) samples that were analyzed in the experimental example of FIG. 5A. Arrows indicate the heterozygous mutation in the tumor sample. FIG. 5C graphically summarizes a Loss of Heterozygosity (LOH) analysis of 37 tumor and paired normal samples from Taiwanese patients that were analyzed in the experimental example of FIGS. 5A and 5B. A value of <0.5 indicates a LOH at the c-CBL locus. FIG. 5D is a schematic depiction of Chromosome 11 markers chosen for LOH analysis in the experimental example of FIGS. 5A-5C, as well as representative examples of LOH chromatogram analysis. After amplification using chromosome 11-specific microsatellite primers, the PCR product was separated by capillary electrophoresis, and bands were quantified according to the intensity.

FIG. 7A shows western blots of whole cell extracts from A549 cells that had been transfected with one of four c-CBL genes (wild-type (WT), Q249E, W802Stop, or S80N/H94Y) in the context of the pAlterMax vector, as described in Example 2 below. FIG. 7A, top, shows that c-CBL mutants did not alter ubiquitination of EGFR. Cells were co-transfected with EGFR, and different c-CBL mutants were stimulated with EGF, immunoprecipitated with anti-EGFR antibody, and blotted with anti-ubiquitin antibody. Immunoblot with anti-EGFR antibody served as the IP control, while the anti-HA blot was used as the input control. FIG. 7B shows the cell viability measurements for these clones. Cell viability was measured by Trypan blue exclusion and compared to empty vector control. c-CBL wild-type (WT) and mutants S80N/H94Y, Q249E, and W802* showed 66.7%, 132.3%, 120.8%, and 147.9% cell viability, respectively, in A549 cells 48 h after transfection. Experiments were performed in triplicate, and the mean data is shown. Error bars indicate the Standard Deviation. FIG. 7C displays c-CBL and beta-actin protein expression levels of the various mutants that were analyzed by Western blots using the appropriate antibodies. FIG. 7D graphically displays cell cycle analysis of the different c-CBL mutants 48 h after transfection in A549 cells.

FIGS. 8A and 8B provide wound healing data. FIG. 8A shows the results of a wound healing assay that was performed in A549 cells that had been transfected with one of four c-CBL genes (wild-type (WT), Q249E, W802*, or S80N/H94Y) in the context of the pAlterMax vector, as described in Example 2 below. Empty vector (EV) was used as a control. Representative pictures (Brightfield and phase contrast) from each time point are shown. FIG. 8B displays a graph of the open wound percentage at each time point. The open wound at each time point was quantified and normalized to 0 h. Experiments were done in triplicate, and the mean data is shown. Error bars indicate Standard Deviation.

FIG. 9A shows images of Western blots of several H358 cell line clones showed that the c-CBL lentiviral shRNA knockdown efficiency varied among the various clones (FIG. 9A), as described in Example 2 below. Scrambled shRNA (Scr) was used as a control. Of all the clones tested, Clone 27, which presented the highest knockdown efficiency, was chosen for further experiments, presented in FIG. 9B. FIG. 9B is a graph showing the cell proliferation percentage for H358 clone 27 cells transfected with shRNA directed toward c-CBL. Lung cancer cell line H358 clone 27 stably transfected with shRNA showed an increase in cell counts compared to the scrambled shRNA control. Experiments were done in triplicates, and the mean data is shown. Error bars indicate Standard Deviation.

FIG. 10A shows images of MET and c-CBL staining in an adenocarcinoma sample and in a NSCLC sample analyzed as described in Example 3 below. Adenocarcinoma and undifferentiated NSCLC were stained with c-CBL and MET antibodies on whole tissue sections. c-CBL staining was diffuse but weak, whereas MET staining in the tumor was strong (T, tumor). The darker areas of c-CBL staining were localized to the lymphocytes (L), whereas no MET staining was detected in lymphocytes. FIG. 10B is a bar graph showing relative staining intensity of MET and c-CBL in tumor sections of samples (n=29, 3=intense, 2=moderate, 1=weak). MET staining was more intense in squamous cell carcinoma (SQ, n=1) and adenocarcinoma (AD, n=1) compared to c-CBL.

FIG. 15A shows representative IHC images of c-CBL, MET, and p-MET expression in HNSCC tumor specimens. FIGS. 15B and C shows pooled tissue microarray (TMA) information related to the expression of c-CBL, c-Met and phosph c-Met. This Figure shows the staining intensity score as described in Example 4 versus the percentage of samples for CBL, c-met and p-met.

FIG. 18A shows a schematic of the functional domains of the c-CBL protein and the location of the mutations identified in 2/20 HNSCC tumor specimens. FIG. 18B shows representative sequencing chromatograms of the mutation region in normal (N) and tumor (T) samples.

FIG. 19A shows a schematic of chromosome 11 with location of primers and representative examples of LOH chromatogram analysis. FIG. 19B shows a summary bar graph of LOH results. A ratio of Tumor:Normal <0.5 indicates LOH at the c-CBL locus.

DETAILED DESCRIPTION OF THE INVENTION

Figure 2:
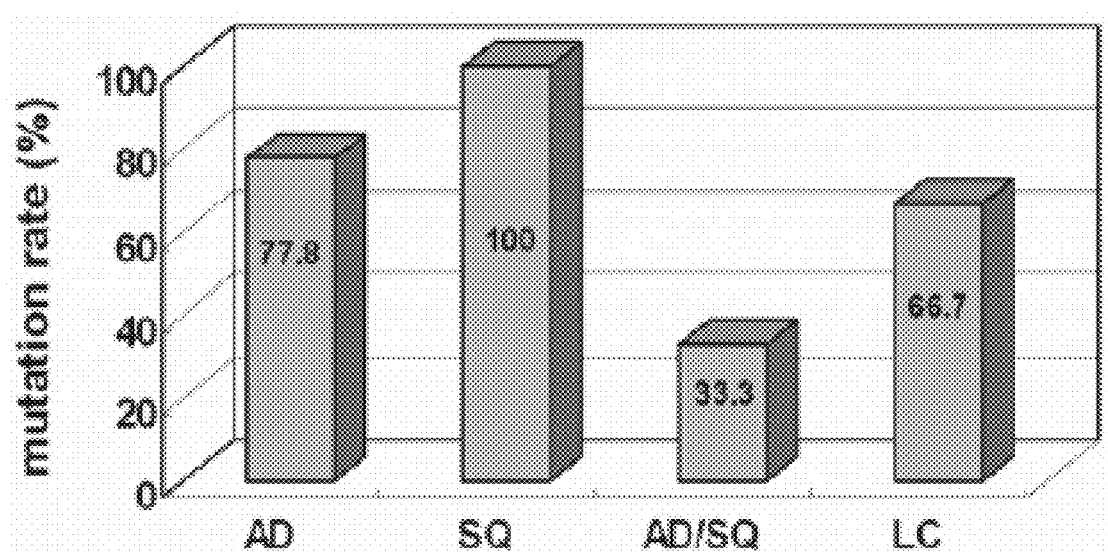
FIG. 2 shows the c-CBL mutation rates for the different tumor types that were studied in as described in Example 1. The mutation rates for adenocarcinoma (AD), squamous cell carcinoma (SQ), adenosquamous carcinoma (AD/SQ), and large cell carcinoma (LC) patients were 77.8%, 100%, 33.3%, and 66.7%, respectively. The statistical analysis showed that the mutation rates between AD and SQ ($P=0.133$), between AD and AD/SQ ($P=0.058$), and between AD and LC ($P=0.599$) were not significant.

The present disclosure describes, at least in part, the discovery of multiple mutational events in the E3 ubiquitin ligase, c-CBL. It was previously thought that aberrant c-Met activity was associated with various cancers, and c-Met became a potential therapeutic target for treating or preventing cancer; however, it was unknown what, if any, treatments would be effective for any given subject.

Disclosed herein are methods of identifying a subject that is susceptible to treatment with a c-Met inhibitor. For example, disclosed herein are methods of identifying a subject that is susceptible to treatment with a c-Met inhibitor comprising determining whether a sample from the subject comprises a mutation in a nucleic acid sequence encoding human c-CBL, wherein the mutation results in an amino acid change at position S80N, H94Y, Q249E, V391I, 72515_72517delATG, W802*, R830K, A848T, L620F, P170L, S171S, L281F, L254S, or P782L.

Also disclosed herein are methods of identifying a subject that is susceptible to treatment with a c-Met inhibitor comprising determining whether a sample from the subject comprises a mutation in a nucleic acid sequence encoding human c-CBL, wherein the mutation is located in the TKB domain, RING finger domain, proline-rich region, C-terminal region, or other domain linkage regions of c-CBL.

Also disclosed herein are methods of identifying a cancer that is susceptible to treatment with a c-Met inhibitor, comprising determining whether a sample from the cancer comprises a mutation in a nucleic acid sequence encoding human c-CBL.

Also disclosed herein are methods of determining responsiveness of a cancer in a subject to treatment with a c-Met inhibitor, said method comprising determining whether a cancer sample from a subject comprises a mutation in a nucleic acid sequence encoding human c-CBL, wherein the mutation results in an amino acid change at position S80N, H94Y, Q249E, V391I, 72515_72517delATG, W802*, R830K, A848T, L620F, P170L, S171S, L281F, L254S, or P782L, wherein the presence of the mutated nucleic acid sequence is indicative that the cancer is responsive to treatment with the c-Met inhibitor.

Also disclosed herein are methods of determining responsiveness of a cancer in a subject to treatment with a c-Met inhibitor, said method comprising determining whether a cancer sample from a subject comprises a mutation in a nucleic acid sequence encoding human c-CBL, wherein the mutation is located in the TKB domain, RING finger domain, proline-rich region, C-terminal region, or other domain linkage regionsv of c-CBL, wherein the presence of the mutated nucleic acid sequence is indicative that the cancer is responsive to treatment with the c-Met inhibitor.

Also disclosed herein are methods of detecting cancer in a sample comprising determining whether the sample comprises a mutation in a nucleic acid sequence encoding human c-CBL, wherein the mutation results in an amino acid change at position S80N, H94Y, Q249E, V391I, 72515_72517delATG, W802*, R830K, A848T, L620F, P170L, S171S, L281F, L254S, or P782L.

Also disclosed herein are methods of detecting cancer in a sample comprising determining whether the sample comprises a mutation in a nucleic acid sequence encoding human c-CBL, wherein the mutation is located in the TKB domain, RING finger domain, proline-rich region, C-terminal region, or other domain linkage regions of the nucleic acid sequence encoding human c-CBL.

All patents, patent applications and publications cited herein, whether supra or infra, are hereby incorporated by reference in their entireties into this application in order to more fully describe the state of the art as known to those skilled therein as of the date of the invention described and claimed herein.

It is to be understood that this invention is not limited to specific synthetic methods, or to specific recombinant biotechnology methods unless otherwise specified, or to particular reagents unless otherwise specified, to specific pharmaceutical carriers, or to particular pharmaceutical formulations or administration regimens, as such may, of course, vary. It is also to be understood that the terminology used herein is for the purpose of describing particular embodiments only and is not intended to be limiting.

Definitions and Nomenclature

The terminology used herein is for the purpose of describing particular embodiments only and is not intended to be limiting.

The invention relates to the discovery that mutations in c-CBL play a role in cancer and have an effect on the effect of c-Met inhibitors. c-CBL refers to the polypeptide encoded by a c-CBL gene. Both of these terms are used herein as general identifiers. Thus, for example, a c-CBL gene or nucleic acid refers to any gene or nucleic acid identified with or derived from a wild-type or mutated c-CBL gene. For example, a mutant c-CBL gene is a form of c-CBL gene.

As used in the specification and the appended claims, the singular forms "a," "an" and "the" can include plural references unless the context clearly dictates otherwise. Thus, for example, reference to "a compound" includes mixtures of compounds; reference to "a pharmaceutical carrier" includes mixtures of two or more such carriers, and the like.

Ranges may be expressed herein as from "about" one particular value, and/or to "about" another particular value. The term "about" is used herein to mean approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 20%. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

The amino acid abbreviations used herein are conventional one letter codes for the amino acids and are expressed as follows: A, alanine; B, asparagine or aspartic acid; C, cysteine; D aspartic acid; E, glutamate, glutamic acid; F, phenylalanine; G, glycine; H histidine; I isoleucine; K, lysine; L, leucine; M, methionine; N, asparagine; P, proline; Q, glutamine; R, arginine; S, serine; T, threonine; V, valine; W, tryptophan; Y, tyrosine; Z, glutamine or glutamic acid.

"Polypeptide" as used herein refers to any peptide, oligopeptide, polypeptide, gene product, expression product, or protein. A polypeptide is comprised of consecutive amino acids. The term "polypeptide" encompasses naturally occurring or synthetic molecules.

In addition, as used herein, the term "polypeptide" refers to amino acids joined to each other by peptide bonds or modified peptide bonds, e.g., peptide isosteres, etc. and may contain modified amino acids other than the 20 gene-encoded amino acids. The polypeptides can be modified by either natural processes, such as post-translational processing, or by chemical modification techniques which are well known in the art. Modifications can occur anywhere in the polypeptide, including the peptide backbone, the amino acid side-chains and the amino or carboxyl termini. The same type of modification can be present in the same or varying degrees at several sites in a given polypeptide. Also, a given polypeptide can have many types of modifications. Modifications include, without limitation, acetylation, acylation, ADP-ribosylation, amidation, covalent cross-linking or cyclization, covalent attachment of flavin, covalent attachment of a heme moiety, covalent attachment of a nucleotide or nucleotide derivative, covalent attachment of a lipid or lipid derivative, covalent attachment of a phosphytidylinositol, disulfide bond formation, demethylation, formation of cysteine or pyroglutamate, formylation, gamma-carboxylation, glycosylation, GPI anchor formation, hydroxylation, iodination, methylation, myristolyation, oxidation, pergylation, proteolytic processing, phosphorylation, prenylation, racemization, selenoylation, sulfation, and transfer-RNA mediated addition of amino acids to protein such as arginylation. (See Proteins—Structure and Molecular Properties 2nd Ed., T. E. Creighton, W.H. Freeman and Company, New York (1993); Posttranslational Covalent Modification of Proteins, B. C. Johnson, Ed., Academic Press, New York, pp. 1-12 (1983)).

As used herein, the term "amino acid sequence" refers to a list of abbreviations, letters, characters or words representing amino acid residues.

As used herein, "peptidomimetic" means a mimetic of a peptide which includes some alteration of the normal peptide chemistry. Peptidomimetics typically enhance some property of the original peptide, such as increase stability, increased efficacy, enhanced delivery, increased half life, etc. Methods of making peptidomimetics based upon a known polypeptide sequence are described, for example, in U.S. Pat. Nos. 5,631,280; 5,612,895; and 5,579,250. Use of peptidomimetics can involve the incorporation of a non-amino acid residue with non-amide linkages at a given position. One embodiment of the present invention is a peptidomimetic wherein the compound has a bond, a peptide backbone or an amino acid component replaced with a suitable mimic. Some non-limiting examples of unnatural amino acids which may be suitable amino acid mimics include β-alanine, L-α-amino butyric acid, L-γ-amino butyric acid, L-α-amino isobutyric acid, L-ε-amino caproic acid, 7-amino heptanoic acid, L-aspartic acid, L-glutamic acid, N-ε-Boc-N-α-CBZ-L-lysine, N-ε-Boc-N-α-Fmoc-L-lysine, L-methionine sulfone, L-norleucine, L-norvaline, N-α-Boc-N-δCBZ-L-ornithine, N-δ-Boc-N-α-CBZ-L-ornithine, Boc-p-nitro-L-phenylalanine, Boc-hydroxyproline, and Boc-L-thioproline.

The word "or" as used herein means any one member of a particular list and also includes any combination of members of that list.

The phrase "nucleic acid" as used herein refers to a naturally occurring or synthetic oligonucleotide or polynucleotide, whether DNA or RNA or DNA-RNA hybrid, single-stranded or double-stranded, sense or antisense, which is capable of hybridization to a complementary nucleic acid by Watson-Crick base-pairing. Nucleic acids of the invention can also include nucleotide analogs (e.g., BrdU), and non-phosphodiester internucleoside linkages (e.g., peptide nucleic acid (PNA) or thiodiester linkages). In particular, nucleic acids can include, without limitation, DNA, RNA, cDNA, gDNA, ssDNA, dsDNA or any combination thereof.

As used herein, "reverse analog" or "reverse sequence" refers to a peptide having the reverse amino acid sequence as another, reference, peptide. For example, if one peptide has the amino acid sequence ABCDE, its reverse analog or a peptide having its reverse sequence is as follows: EDCBA.

By "sample" is meant an animal; a tissue or organ from an animal; a cell (either within a subject, taken directly from a subject, or a cell maintained in culture or from a cultured cell line); a cell lysate (or lysate fraction) or cell extract; or a solution containing one or more molecules derived from a cell or cellular material (e.g. a polypeptide or nucleic acid), which is assayed as described herein. A sample may also be any body fluid or excretion (for example, but not limited to, blood, urine, stool, saliva, tears, bile) that contains cells or cell components.

By "modulate" is meant to alter, by increase or decrease.

By "normal subject" is meant an individual who does not have cancer as well as an individual who has increased susceptibility for developing a cancer.

By an "effective amount" of a compound as provided herein is meant a sufficient amount of the compound to provide the desired effect. The exact amount required will vary from subject to subject, depending on the species, age, and general condition of the subject, the severity of disease (or underlying genetic defect) that is being treated, the particular compound used, its mode of administration, and the like. Thus, it is not possible to specify an exact "effective amount." However, an appropriate "effective amount" may be determined by one of ordinary skill in the art using only routine experimentation.

By "isolated polypeptide" or "purified polypeptide" is meant a polypeptide (or a fragment thereof) that is substantially free from the materials with which the polypeptide is normally associated in nature. The polypeptides of the invention, or fragments thereof, can be obtained, for example, by extraction from a natural source (for example, a mammalian cell), by expression of a recombinant nucleic acid encoding the polypeptide (for example, in a cell or in a cell-free translation system), or by chemically synthesizing the polypeptide. In addition, polypeptide fragments may be obtained by any of these methods, or by cleaving full length polypeptides.

By "isolated nucleic acid" or "purified nucleic acid" is meant DNA that is free of the genes that, in the naturally-occurring genome of the organism from which the DNA of the invention is derived, flank the gene. The term therefore includes, for example, a recombinant DNA which is incorporated into a vector, such as an autonomously replicating plasmid or virus; or incorporated into the genomic DNA of a prokaryote or eukaryote (e.g., a transgene); or which exists as a separate molecule (for example, a cDNA or a genomic or cDNA fragment produced by PCR, restriction endonuclease digestion, or chemical or in vitro synthesis). It also includes a recombinant DNA which is part of a hybrid gene encoding additional polypeptide sequence. The term "isolated nucleic acid" also refers to RNA, e.g., an mRNA molecule that is encoded by an isolated DNA molecule, or that is chemically synthesized, or that is separated or substantially free from at least some cellular components, for example, other types of RNA molecules or polypeptide molecules.

By a "transgene" is meant a nucleic acid sequence that is inserted by artifice into a cell and becomes a part of the genome of that cell and its progeny. Such a transgene may be (but is not necessarily) partly or entirely heterologous (for example, derived from a different species) to the cell.

By "transgenic animal" an animal comprising a transgene as described above. Transgenic animals are made by techniques that are well known in the art.

By "knockout mutation" is meant an alteration in the nucleic acid sequence that reduces the biological activity of the polypeptide normally encoded therefrom by at least 80% relative to the unmutated gene. The mutation may, without limitation, be an insertion, deletion, frameshift, or missense mutation. A "knockout animal," for example, a knockout mouse, is an animal containing a knockout mutation. The knockout animal may be heterozygous or homozygous for the knockout mutation. Such knockout animals are generated by techniques that are well known in the art. A preferred form of knockout mutation is one where the biological activity of the c-CBL polypeptide is not completely eliminated.

By "treat" is meant to administer a compound or molecule to a subject, such as a human or other mammal (for example, an animal model), that has an increased susceptibility for developing a cancer, or that has a cancer, in order to prevent or delay a worsening of the effects of the disease or condition, or to partially or fully reverse the effects of the disease.

By "prevent" is meant to minimize the chance that a subject who has an increased susceptibility for developing a cancer will develop a cancer.

By "specifically binds" is meant that an antibody recognizes and physically interacts with its cognate antigen (for example, a c-CBL polypeptide) and does not significantly recognize and interact with other antigens; such an antibody may be a polyclonal antibody or a monoclonal antibody, which are generated by techniques that are well known in the art.

By "probe," "primer," or oligonucleotide is meant a single-stranded DNA or RNA molecule of defined sequence that can base-pair to a second DNA or RNA molecule that contains a complementary sequence (the "target"). The stability of the resulting hybrid depends upon the extent of the base-pairing that occurs. The extent of base-pairing is affected by parameters such as the degree of complementarity between the probe and target molecules and the degree of stringency of the hybridization conditions. The degree of hybridization stringency is affected by parameters such as temperature, salt concentration, and the concentration of organic molecules such as formamide, and is determined by methods known to one skilled in the art. Probes or primers specific for c-CBL nucleic acids (for example, genes and/or mRNAs) have at least 80%-90% sequence complementarity, preferably at least 91%-95% sequence complementarity, more preferably at least 96%-99% sequence complementarity, and most preferably 100% sequence complementarity to the region of the c-CBL nucleic acid to which they hybridize. Probes, primers, and oligonucleotides may be detectably-labeled, either radioactively, or non-radioactively, by methods well-known to those skilled in the art. Probes, primers, and oligonucleotides are used for methods involving nucleic acid hybridization, such as: nucleic acid sequencing, reverse transcription and/or nucleic acid amplification by the polymerase chain reaction, single stranded conformational polymorphism (SSCP) analysis, restriction fragment polymorphism (RFLP) analysis, Southern hybridization, Northern hybridization, in situ hybridization, electrophoretic mobility shift assay (EMSA).

By "specifically hybridizes" is meant that a probe, primer, or oligonucleotide recognizes and physically interacts (that is, base-pairs) with a substantially complementary nucleic acid (for example, a c-CBL nucleic acid) under high stringency conditions, and does not substantially base pair with other nucleic acids.

By "high stringency conditions" is meant conditions that allow hybridization comparable with that resulting from the use of a DNA probe of at least 40 nucleotides in length, in a buffer containing 0.5 M NaHPO$_4$, pH 7.2, 7% SDS, 1 mM EDTA, and 1% BSA (Fraction V), at a temperature of 65° C., or a buffer containing 48% formamide, 4.8×SSC, 0.2 M Tris-Cl, pH 7.6, 1×Denhardt's solution, 10% dextran sulfate, and 0.1% SDS, at a temperature of 42° C. Other conditions for high stringency hybridization, such as for PCR, Northern, Southern, or in situ hybridization, DNA sequencing, etc., are well-known by those skilled in the art of molecular biology. (See, for example, F. Ausubel et al., Current Protocols in Molecular Biology, John Wiley & Sons, New York, N.Y., 1998).

By "familial mutation" or "inherited mutation" is meant a mutation in an individual that was inherited from a parent and that was present in somatic cells of the parent. By "sporadic mutation" or "spontaneous mutation" is meant a mutation in an individual that arose in the individual and was not present in a parent of the individual.

As set forth herein, nucleotides are numbered according to the consensus coding DNA sequence (CCDS) cDNA sequence for c-CBL (SEQ ID1 or CCDS8418), starting at nucleotide 1. The sequence is also set forth in Table 1.

The amino acid sequence of c-CBL are shown in SEQ ID2 or in UniProtKB/Swiss-Prot P22681, starting at amino acid 1, respectively. The sequence is also set forth in Table 2.

TABLE 1

Consensus coding DNA sequence (CCDS) cDNA sequence
for c-CBL (SEQ ID NO: 1)
(2721 nt)

ATGGCCGGCAACGTGAAGAAGAGCTCTGGGGCCGGGGGCGGCAGCGGCTC
CGGGGGCTCGGGTTCGGGTGGCCTGATTGGGCTCATGAAGGACGCCTTCC
AGCCGCACCACCACCACCACCACCACCTCAGCCCCCACCCGCCGGGGACG
GTGGACAAGAAGATGGTGGAGAAGTGCTGGAAGCTCATGGACAAGGTGGT
GCGGTTGTGTCAGAACCCAAAGCTGGCGCTAAAGAATAGCCCACCTTATA
TCTTAGACCTGCTACCAGATACCTACCAGCATCTCCGTACTATCTTGTCA
AGATATGAGGGGAAGATGGAGACACTTGGAGAAAATGAGTATTTTAGGGT
GTTTATGGAGAATTTGATGAAGAAAACTAAGCAAACCATAAGCCTCTTCA
AGGAGGGAAAAGAAAGAATGTATGAGGAGAATTCTCAGCCTAGGCGAAAC
CTAACCAAACTGTCCCTCATCTTCAGCCACATGCTGGCAGAACTAAAAGG
AATCTTTCCAAGTGGACTCTTTCAGGGAGACACATTTCGGATTACTAAAG
CAGATGCTGCGGAATTTTGGAGAAAAGCTTTTGGGGAAAAGACAATAGTC
CCTTGGAAGAGCTTTCGACAGGCTCTACATGAAGTGCATCCCATCAGTTC
TGGGCTGGAGGCCATGGCTCTGAAATCCACTATTGATCTGACCTGCAATG
ATTATATTTCGGTTTTTGAATTTGACATCTTTACCCGACTCTTTCAGCCC
TGGTCCTCTTTGCTCAGGAATTGGAACAGCCTTGCTGTAACTCATCCTGG
CTACATGGCTTTTTTGACGTATGACGAAGTGAAAGCTCGGCTCCAGAAAT
TCATTCACAAACCTGGCAGTTATATCTTCCGGCTGAGCTGTACTCGTCTG
GGTCAGTGGGCTATTGGGTATGTTACTGCTGATGGGAACATTCTCCAGAC
AATCCCTCACAATAAACCTCTCTTCCAAGCACTGATTGATGGCTTCAGGG
AAGGCTTCTATTTGTTTCCTGATGGACGAAATCAGAATCCTGATCTGACT
GGCTTATGTGAACCAACTCCCCAAGACCATATCAAAGTGACCCAGGAACA
ATATGAATTATACTGTGAGATGGGCTCCACATTCCAACTATGTAAAATAT
GTGCTGAAAATGATAAGGATGTAAAGATTGAGCCCTGTGGACACCTCATG
TGCACATCCTGTCTTACATCCTGGCAGGAATCAGAAGGTCAGGGCTGTCC
TTTCTGCCGATGTGAAATTAAAGGTACTGAACCCATCGTGGTAGATCCGT
TTGATCCTAGAGGGAGTGGCAGCCTGTTGAGGCAAGGAGCAGAGGGAGCT
CCCTCCCCAAATTATGATGATGATGATGAACGAGCTGATGATACTCT
CTTCATGATGAAGGAATTGGCTGGTGCCAAGGTGGAACGGCCGCCTTCTC
CATTCTCCATGGCCCCACAAGCTTCCCTTCCCCGGTGCCACCACGACTT
GACCTTCTGCCGCAGCGAGTATGTGTTCCCTCAAGTCTTCTGCTCTTGGA
ACTGCTTCTAAGGCTGCTTCTGGCTCCCTTCATAAAGACAAACCATTGCC
AGTACCTCCCACACTTCGAGATCTTCCACCACCACCGCCTCCAGACCGGC
CATATTCTGTTGGAGCAGAATCCCGACCTCAAAGACGCCCCTTGCCTTGT
ACACCAGGCGACTGTCCCTCCAGAGACAAACTGCCCCCTGTCCCCTCTAG
CCGCCTTGGAGACTCATGGCTGCCCCGGCCAATCCCCAAAGTACCAGTAT
CTGCCCCAAGTTCCAGTGATCCCTGGACAGGAAGAGAATTAACCAACCGG

TABLE 1-continued

Consensus coding DNA sequence (CCDS) cDNA sequence
for c-CBL (SEQ ID NO: 1)
(2721 nt)

```
CACTCACTTCCATTTTCATTGCCCTCACAAATGGAGCCCAGACCAGATGT
GCCTAGGCTCGGAAGCACGTTCAGTCTGGATACCTCCATGAGTATGAATA
GCAGCCCATTAGTAGGTCCAGAGTGTGACCACCCCAAAATCAAACCTTCC
TCATCTGCCAATGCCATTTATTCTCTGGCTGCCAGACCTCTTCCTGTGCC
AAAACTGCCACCTGGGGAGCAATGTGAGGGTGAAGAGGACACAAGTACAT
GACTCCCTCTTCCAGGCCTCTACGGCCTTTGGATACATCCCAGAGTTCAC
GAGCATGTGATTGCGACCAGCAGATTGATAGCTGTACGTATGAAGCAATG
TATAATATTCAGTCCCAGGCGCCATCTATCACCGAGAGCAGCACCTTTGG
TGAAGGGAATTTGGCCGCAGCCCATGCCAACACTGGTCCCGAGGAGTCAG
AAAATGAGGATGATGGGTATGATGTCCCAAAGCCACCTGTGCCGGCCGTG
CTGGCCCGCCGAACTCTCTCAGATATCTCTAATGCCAGCTCCTCCTTTGG
CTGGTTGTCTCTGGATGGTGATCCTACAACAAATGTCACTGAAGGTTCCC
AAGTTCCCGAGAGGCCTCCAAAACCATTCCCGCGGAGAATCAACTCTGAA
CGGAAAGCTGGCAGCTGTCAGCAAGGTAGTGGTCCTGCCGCCTCTGCTGC
CACCGCCTCACCTCAGCTCTCCAGTGAGATCGAGAACCTCATGAGTCAGG
GGTACTCCTACCAGGACATCCAGAAAGCTTTGGTCATTGCCCAGAACAAC
ATCGAGATGGCCAAAAACATCCTCCGGGAATTTGTTTCCATTTCTTCTCC
TGCCCATGTAGCTACCTAG
```

TABLE 2

SEQ ID NO :2 Amino Acid Sequence
(Amino Acids 1-906)

```
MAGNVKKSSGAGGGSGSGSGSGGLIGLMKDAFQPHHHHHHHLSPHPPGT
VDKKMVEKCWKLMDKVVRLCQNPKLALKNSPPYILDLLPDTYQHLRTILS
RYEGKMETLGENEYFRVFMENLMKKTKQTISLFKEGKERMYEENSQPRRN
LTKLSLIFSHMLAELKGIFPSGLFQGDTFRITKADAAEFWRKAFGEKTIV
PWKSFRQALHEVHPISSGLEAMALKSTIDLTCNDYISVFEFDIFTRLFQP
WSSLLRNWNSLAVTHPGYMAFLTYDEVKARLQKFIHKPGSYIFRLSCTRL
GQWAIGYVTADGNILQTIPHNKPLFQALIDGFREGFYLFPDGRNQNPDLT
GLCEPTPQDHIKVTQEQYELYCEMGSTFQLCKICAENDKDVKIEPCGHLM
CTSCLTSWQESEGQGCPFCRCEIKGTEPIVVDPFDPRGSGSLLRQGAEGA
PSPNYDDDDDERADDTLFMMKELAGAKVERPPSPFSMAPQASLPPVPPRL
DLLPQRVCVPSSASALGTASKAASGSLHKDKPLPVPPTLRDLPPPPPPDR
PYSVGAESRPQRRPLPCTPGDCPSRDKLPPVPSSRLGDSWLPRPIPKVPV
SAPSSSDPWTGRELTNRHSLPFSLPSQMEPRPDVPRLGSTFSLDTSMSMN
SSPLVGPECDHPKIKPSSSANAIYSLAARPLPVPKLPPGEQCEGEEDTEY
MTPSSRPLRPLDTSQSSRACDCDQQIDSCTYEAMYNIQSQAPSITESSTF
GEGNLAAAHANTGPEESENEDDGYDVPKPPVPAVLARRTLSDISNASSSF
GWLSLDGDPTTNVTEGSQVPERPPKPFPRRINSERKAGSCQQGSGPAASA
ATASPQLSSEIENLMSQGYSYQDIQKALVIAQNNIEMAKNILREFVSISS
PAHVAT
```

As used herein, a specific notation will be used to denote certain types of mutations. All notations referencing a nucleotide or amino acid residue will be understood to correspond to the residue number of the wild-type c-CBL nucleic acid sequence set forth at SEQ ID NO: 1, or of the wild-type c-CBL polypeptide sequence set forth at SEQ ID NO:2. Thus, for example, the notation "S80N" when used in the context of a polypeptide sequence will be used to indicate that the amino acid Serine at position 80 has been replaced with Asparagine.

In the method of the invention, the mutant c-CBL polypeptide or mutated c-CBL nucleic acid identified can be associated with cancers.

Compositions

The disclosed compositions are related to c-CBL. Disclosed herein are compositions, such as polynucleotides capable of specifically hybridizing to c-CBL encoding human c-CBL, wherein the mutation results in an amino acid change at position S80N, H94Y, Q249E, V391I, 72515_72517delATG, R830K, A848T, L620F, P170L, S171S, L281F, L254S, or P782L, or a stop codon at position W802*, or a complement thereof.

lso disclosed are isolated polynucleotides that comprise mutations in a nucleotide sequence capable of encoding a c-CBL protein, that do not result in a change in the amino acid sequence. Such mutations can sometimes be referred to as "silent mutations". "Silent mutations" described above, can be used in the same methods and within the same compositions as the other mutations described herein.

The disclosed nucleic acids are made up of for example, nucleotides, nucleotide analogs, or nucleotide substitutes. Non-limiting examples of these and other molecules are discussed herein. It is understood that for example, when a vector is expressed in a cell that the expressed mRNA will typically be made up of A, C, G, and U. Likewise, it is understood that if, for example, an antisense molecule is introduced into a cell or cell environment through for example exogenous delivery, it is advantageous that the antisense molecule be made up of nucleotide analogs that reduce the degradation of the antisense molecule in the cellular environment.

The nucleotides of the invention can comprise one or more nucleotide analogs or substitutions. A nucleotide analog is a nucleotide which contains some type of modification to either the base, sugar, or phosphate moieties. Modifications to the base moiety would include natural and synthetic modifications of A, C, G, and T/U as well as different purine or pyrimidine bases, such as uracil-5-yl (ψ), hypoxanthin-9-yl (I), and 2-aminoadenin-9-yl. A modified base includes but is not limited to 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 8-azaguanine and 8-azaadenine, 7-deazaguanine and 7-deazaadenine and 3-deazaguanine and 3-deazaadenine. Additional base modifications can be found for example in U.S. Pat. No. 3,687,808, Englisch et al., Angewandte Chemie, International Edition, 1991, 30, 613, and Sanghvi, Y. S., Chapter 15, Antisense Research and Applications, pages 289-302, Crooke, S. T. and Lebleu, B. ed., CRC Press, 1993. Certain nucleotide analogs, such as 5-substituted pyrimidines, 6-azapyrimidines and N-2, N-6 and O-6 substituted purines, including 2-aminopropyladenine, 5-propynyluracil and 5-propynylcytosine. 5-methylcytosine can increase the stability of duplex formation. Often time base modifications can be combined with for example a sugar modification, such as 2'-O-methoxyethyl, to achieve unique properties such as increased duplex stability. There are numerous United States patents such as U.S. Pat. Nos. 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121; 5,596,091; 5,614,617; and 5,681,941, which detail and describe a range of base modifications. Each of these patents is herein incorporated by reference.

Nucleotide analogs can also include modifications of the sugar moiety. Modifications to the sugar moiety would include natural modifications of the ribose and deoxy ribose as well as synthetic modifications. Sugar modifications include but are not limited to the following modifications at the 2' position: OH; F; O-, S-, or N-alkyl; O-, S-, or N-alkenyl; O-, S- or N-alkynyl; or O-alkyl-O-alkyl, wherein the alkyl, alkenyl and alkynyl may be substituted or unsubstituted $C_1$ to $C_{10}$, alkyl or $C_2$ to $C_{10}$ alkenyl and alkynyl. 2' sugar modifications also include but are not limited to —O[(CH$_2$)$_n$O]$_m$CH$_3$, —O(CH$_2$)$_n$OCH$_3$, —O(CH$_2$)$_n$NH$_2$, —O(CH$_2$)$_n$CH$_3$, —O(CH$_2$)$_n$—ONH$_2$, and —O(CH$_2$)$_n$ON [(CH$_2$)$_n$CH$_3$)]$_2$, where n and m are from 1 to about 10.

Other modifications at the 2' position include but are not limited to: $C_1$ to $C_{10}$ lower alkyl, substituted lower alkyl, alkaryl, aralkyl, O-alkaryl or O-aralkyl, SH, SCH$_3$, OCN, Cl, Br, CN, CF$_3$, OCF$_3$, SOCH$_3$, SO$_2$ CH$_3$, ONO$_2$, NO$_2$, N$_3$, NH$_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. Similar modifications may also be made at other positions on the sugar, particularly the 3' position of the sugar on the 3' terminal nucleotide or in 2'-5' linked oligonucleotides and the 5' position of 5' terminal nucleotide. Modified sugars would also include those that contain modifications at the bridging ring oxygen, such as CH$_2$ and S. Nucleotide sugar analogs may also have sugar mimetics such as cyclobutyl moieties in place of the pentofuranosyl sugar. There are numerous United States patents that teach the preparation of such modified sugar structures such as U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; and 5,700,920, each of which is herein incorporated by reference in its entirety for their teaching of modifications and methods related to the same.

Nucleotide analogs can also be modified at the phosphate moiety. Modified phosphate moieties include but are not limited to those that can be modified so that the linkage between two nucleotides contains a phosphorothioate, chiral phosphorothioate, phosphorodithioate, phosphotriester, aminoalkylphosphotriester, methyl and other alkyl phosphonates including 3'-alkylene phosphonate and chiral phosphonates, phosphinates, phosphoramidates including 3'-amino phosphoramidate and aminoalkylphosphoramidates, thionophosphoramidates, thionoalkylphosphonates, thionoalkylphosphotriesters, and boranophosphates. It is understood that these phosphate or modified phosphate linkage between two nucleotides can be through a 3'-5' linkage or a 2'-5' linkage, and the linkage can contain inverted polarity such as 3'-5' to 5'-3' or 2'-5' to 5'-2'. Various salts, mixed salts and free acid forms are also included. Numerous United States patents teach how to make and use nucleotides containing modified phosphates and include but are not limited to, U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; and 5,625,050, each of which is herein incorporated by reference in its entirety for their teaching of modifications and methods related to the same.

Nucleotide substitutes are molecules having similar functional properties to nucleotides, but which do not contain a phosphate moiety, such as peptide nucleic acid (PNA). Nucleotide substitutes are molecules that will recognize nucleic acids in a Watson-Crick or Hoogsteen manner, but which are linked together through a moiety other than a phosphate moiety. Nucleotide substitutes are able to conform to a double helix type structure when interacting with the appropriate target nucleic acid.

Nucleotide substitutes are nucleotides or nucleotide analogs that have had the phosphate moiety or sugar moieties replaced. Nucleotide substitutes do not contain a standard phosphorus atom. Substitutes for the phosphate can be, for example, short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and CH$_2$ component parts. Numerous United States patents disclose how to make and use these types of phosphate replacements and include but are not limited to U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; and 5,677,439, each of which is herein incorporated by reference in its entirety for their teaching of modifications and methods related to the same.

It is also understood in a nucleotide substitute that both the sugar and the phosphate moieties of the nucleotide can be replaced, by for example an amide type linkage (aminoethylglycine) (PNA). U.S. Pat. Nos. 5,539,082; 5,714,331; and 5,719,262 teach how to make and use PNA molecules, each of which is herein incorporated by reference in its entirety for their teaching of modifications and methods related to the same. (See also Nielsen et al., Science, 254, 1497-1500 (1991)).

It is also possible to link other types of molecules (conjugates) to nucleotides or nucleotide analogs to enhance for example, cellular uptake. Conjugates can be chemically linked to the nucleotide or nucleotide analogs. Such conjugates include but are not limited to lipid moieties such as a cholesterol moiety (Letsinger et al., Proc. Natl. Acad. Sci. USA, 1989, 86, 6553-6556), cholic acid (Manoharan et al., Bioorg. Med. Chem. Let., 1994, 4, 1053-1060), a thioether, e.g., hexyl-S-tritylthiol (Manoharan et al., Ann. N.Y. Acad. Sci., 1992, 660, 306-309; Manoharan et al., Bioorg. Med. Chem. Let., 1993, 3, 2765-2770), a thiocholesterol (Oberhauser et al., Nucl. Acids Res., 1992, 20, 533-538), an aliphatic chain, e.g., dodecandiol or undecyl residues (Saison-Behmoaras et al., EMBO J., 1991, 10, 1111-1118; Kabanov et al., FEBS Lett., 1990, 259, 327-330; Svinarchuk et al., Biochimie, 1993, 75, 49-54), a phospholipid, e.g., di-hexadecyl-rac-glycerol or triethylammonium 1,2-di-O-hexadecyl-rac-glycero-3-H-phosphonate (Manoharan et al., Tetrahedron Lett., 1995, 36, 3651-3654; Shea et al., Nucl. Acids Res., 1990, 18, 3777-3783), a polyamine or a polyethylene glycol chain (Manoharan et al., Nucleosides & Nucleotides, 1995, 14, 969-973), or adamantane acetic acid (Manoharan et al., Tetrahedron Lett., 1995, 36, 3651-3654), a palmityl moiety (Mishra et al., Biochim. Biophys. Acta, 1995, 1264, 229-237), or an octadecylamine or hexylaminocarbonyl-oxycholesterol moiety (Crooke et al., J. Pharmacol. Exp. Ther., 1996, 277, 923-937).

Numerous United States patents teach the preparation of such conjugates and include, but are not limited to U.S. Pat.

Nos. 4,828,979; 4,948,882; 5,218,105; 5,525,465; 5,541,313; 5,545,730; 5,552,538; 5,578,717; 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241; 5,391,723; 5,416,203; 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941, each of which is herein incorporated by reference in its entirety for their teaching of modifications and methods related to the same.

The same methods of calculating homology as described elsewhere herein concerning polypeptides can be obtained for nucleic acids by for example the algorithms disclosed in Zuker, M. Science 244:48-52, 1989, Jaeger et al. Proc. Natl. Acad. Sci. USA 86:7706-7710, 1989, and Jaeger et al. Methods Enzymol. 183:281-306, 1989 which are herein incorporated by reference for at least material related to nucleic acid alignment.

Also, disclosed are compositions including primers and probes, which are capable of interacting with the polynucleotide sequences disclosed herein. For example, disclosed are primers/probes capable of amplifying a nucleic acid encoding human c-CBL, wherein the mutation results in an amino acid change at position S80N, H94Y, Q249E, V391I, 72515_72517delATG, W802*, R830K, A848T, L620F, P170L, S171S, L281F, L254S, or P782L. Examples of such primers/probes are disclosed elsewhere herein. For example, examples of primers and probes can be found in the Examples section below.

The disclosed primers can used to support DNA amplification reactions. Typically the primers will be capable of being extended in a sequence specific manner. Extension of a primer in a sequence specific manner includes any methods wherein the sequence or composition of the nucleic acid molecule to which the primer is hybridized or otherwise associated directs or influences the composition or sequence of the product produced by the extension of the primer. Extension of the primer in a sequence specific manner therefore includes, but is not limited to, PCR, DNA sequencing, DNA extension, DNA polymerization, RNA transcription, or reverse transcription. Techniques and conditions that amplify the primer in a sequence specific manner are preferred. In certain embodiments the primers are used for the DNA amplification reactions, such as PCR or direct sequencing. It is understood that in certain embodiments the primers can also be extended using non-enzymatic techniques, where for example, the nucleotides or oligonucleotides used to extend the primer are modified such that they will chemically react to extend the primer in a sequence specific manner. Typically the disclosed primers hybridize with the polynucleotide sequences disclosed herein or region of the polynucleotide sequences disclosed herein or they hybridize with the complement of the polynucleotide sequences disclosed herein or complement of a region of the polynucleotide sequences disclosed herein.

The size of the primers or probes for interaction with the polynucleotide sequences disclosed herein in certain embodiments can be any size that supports the desired enzymatic manipulation of the primer, such as DNA amplification or the simple hybridization of the probe or primer. A typical primer or probe would be at least 6, 7, 8, 9, 10, 20, 30, 40, 50, 60, 70, 80, 90, 100, 125, 150, 175, 200, 225, 250, 275, 300, 325, 350, 375, 400, 425, 450, 475, 500, 550, 600, 650, 700, 750, 800, 850, 900, 950, 1000, 1250, 1500, 1750, 2000, 2250, 2500, 2750, 3000, 3500, or 4000 nucleotides long or any length in-between.

Also disclosed is an isolated polynucleotide capable of distinguishing between isolated polynucleotides capable of encoding polypeptides comprising a mutation at a nucleic acid position corresponding to an amino acid change at position S80N, H94Y, Q249E, V391I, 72515_72517delATG, W802*, R830K, A848T, L620F, P170L, S171S, L281F, L254S, or P782L, or a complement thereof, and a nucleic acid encoding a wild type c-CBL.

Optionally, isolated polypeptides or isolated nucleotides can also be purified, e.g., are at least about 90% pure, more preferably at least about 95% pure and most preferably at least about 99% pure.

Also disclosed are the components to be used to prepare the disclosed compositions as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein. For example, if a particular polypeptide is disclosed and discussed and a number of modifications that can be made to a number of molecules including the polypeptide are discussed, specifically contemplated are each and every combination and permutation of polypeptide and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the disclosed compositions. Thus, if there are a variety of additional steps that can be performed it is understood that each of these additional steps can be performed with any specific embodiment or combination of embodiments of the disclosed methods.

It is understood that one way to define any known variants and derivatives or those that might arise, of the disclosed genes and proteins herein is through defining the variants and derivatives in terms of homology to specific known sequences. For example SEQ ID NO: 1 sets forth a particular sequence of the wild-type c-CBL gene and SEQ ID NO: 2 sets forth a particular sequence of the protein encoded by SEQ ID NO: 1. Specifically disclosed are variants of these and other genes and proteins herein disclosed which have at least, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99 percent homology to the stated sequence. Those of skill in the art readily understand how to determine the homology of two proteins or nucleic acids, such as genes. For example, the homology can be calculated after aligning the two sequences so that the homology is at its highest level.

Another way of calculating homology can be performed by published algorithms. Optimal alignment of sequences for comparison may be conducted by the local homology algorithm of Smith and Waterman Adv. Appl. Math. 2: 482

(1981), by the homology alignment algorithm of Needleman and Wunsch, J. MoL Biol. 48: 443 (1970), by the search for similarity method of Pearson and Lipman, Proc. Natl. Acad. Sci. U.S.A. 85: 2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by inspection.

The same types of homology can be obtained for nucleic acids by for example the algorithms disclosed in Zuker, M. Science 244:48-52, 1989, Jaeger et al. Proc. Natl. Acad. Sci. USA 86:7706-7710, 1989, Jaeger et al. Methods Enzymol. 183:281-306, 1989 which are herein incorporated by reference for at least material related to nucleic acid alignment.

For example, as used herein, a sequence recited as having a particular percent homology to another sequence refers to sequences that have the recited homology as calculated by any one or more of the calculation methods described above. For example, a first sequence has 80 percent homology, as defined herein, to a second sequence if the first sequence is calculated to have 80 percent homology to the second sequence using the Zuker calculation method even if the first sequence does not have 80 percent homology to the second sequence as calculated by any of the other calculation methods. As another example, a first sequence has 80 percent homology, as defined herein, to a second sequence if the first sequence is calculated to have 80 percent homology to the second sequence using both the Zuker calculation method and the Pearson and Lipman calculation method even if the first sequence does not have 80 percent homology to the second sequence as calculated by the Smith and Waterman calculation method, the Needleman and Wunsch calculation method, the Jaeger calculation methods, or any of the other calculation methods. As yet another example, a first sequence has 80 percent homology, as defined herein, to a second sequence if the first sequence is calculated to have 80 percent homology to the second sequence using each of calculation methods (although, in practice, the different calculation methods will often result in different calculated homology percentages).

The term hybridization typically means a sequence driven interaction between at least two nucleic acid molecules, such as a primer or a probe and a gene. Sequence driven interaction means an interaction that occurs between two nucleotides or nucleotide analogs or nucleotide derivatives in a nucleotide specific manner. For example, G interacting with C or A interacting with T are sequence driven interactions. Typically sequence driven interactions occur on the Watson-Crick face or Hoogsteen face of the nucleotide. The hybridization of two nucleic acids is affected by a number of conditions and parameters known to those of skill in the art. For example, the salt concentrations, pH, and temperature of the reaction all affect whether two nucleic acid molecules will hybridize.

Parameters for selective hybridization between two nucleic acid molecules are well known to those of skill in the art. For example, in some embodiments selective hybridization conditions can be defined as stringent hybridization conditions. For example, stringency of hybridization is controlled by both temperature and salt concentration of either or both of the hybridization and washing steps. For example, the conditions of hybridization to achieve selective hybridization may involve hybridization in high ionic strength solution (6×SSC or 6×SSPE) at a temperature that is about 12-25° C. below the Tm (the melting temperature at which half of the molecules dissociate from their hybridization partners) followed by washing at a combination of temperature and salt concentration chosen so that the washing temperature is about 5° C. to 20° C. below the Tm. The temperature and salt conditions are readily determined empirically in preliminary experiments in which samples of reference DNA immobilized on filters are hybridized to a labeled nucleic acid of interest and then washed under conditions of different stringencies. Hybridization temperatures are typically higher for DNA-RNA and RNA-RNA hybridizations. The conditions can be used as described above to achieve stringency, or as is known in the art. (Sambrook et al., Molecular Cloning: A Laboratory Manual, 2nd Ed., Cold Spring Harbor Laboratory, Cold Spring Harbor, N.Y., 1989; Kunkel et al. Methods Enzymol. 1987:154: 367, 1987 which is herein incorporated by reference in its entirety and at least for material related to hybridization of nucleic acids). As used herein "stringent hybridization" for a DNA:DNA hybridization is about 68° C. (in aqueous solution) in 6×SSC or 6×SSPE followed by washing at 68° C. Stringency of hybridization and washing, if desired, can be reduced accordingly as the degree of complementarity desired is decreased, and further, depending upon the G-C or A-T richness of any area wherein variability is searched for. Likewise, stringency of hybridization and washing, if desired, can be increased accordingly as homology desired is increased, and further, depending upon the G-C or A-T richness of any area wherein high homology is desired, all as known in the art.

Another way to define selective hybridization is by looking at the amount (percentage) of one of the nucleic acids bound to the other nucleic acid. For example, in some embodiments selective hybridization conditions would be when at least about, 60, 65, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 percent of the limiting nucleic acid is bound to the non-limiting nucleic acid. Typically, the non-limiting primer is in for example, 10 or 100 or 1000 fold excess. This type of assay can be performed at under conditions where both the limiting and non-limiting primer are for example, 10 fold or 100 fold or 1000 fold below their $k_d$, or where only one of the nucleic acid molecules is 10 fold or 100 fold or 1000 fold or where one or both nucleic acid molecules are above their $k_d$.

Another way to define selective hybridization is by looking at the percentage of primer that gets enzymatically manipulated under conditions where hybridization is required to promote the desired enzymatic manipulation. For example, in some embodiments selective hybridization conditions would be when at least about, 60, 65, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 percent of the primer is enzymatically manipulated under conditions which promote the enzymatic manipulation, for example if the enzymatic manipulation is DNA extension, then selective hybridization conditions would be when at least about 60, 65, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 percent of the primer molecules are extended. Preferred conditions also include those suggested by the manufacturer or indicated in the art as being appropriate for the enzyme performing the manipulation.

Just as with homology, it is understood that there are a variety of methods herein disclosed for determining the level of hybridization between two nucleic acid molecules. It is understood that these methods and conditions may provide different percentages of hybridization between two nucleic acid molecules, but unless otherwise indicated meeting the parameters of any of the methods would be sufficient. For example if 80% hybridization was required and as long as hybridization occurs within the required parameters in any one of these methods it is considered disclosed herein.

It is understood that those of skill in the art understand that if a composition or method meets any one of these criteria for determining hybridization either collectively or singly it is a composition or method that is disclosed herein. Optionally, one or more of the isolated polynucleotides of the invention are attached to a solid support. Solid supports are disclosed herein.

Also disclosed herein are arrays comprising polynucleotides capable of specifically hybridizing to c-CBL encoding nucleic acid comprising a mutation at a nucleic acid position corresponding to a change in amino acid at position S80N, H94Y, Q249E, V391I, 72515_72517delATG, W802*, R830K, A848T, L620F, P170L, S171S, L281F, L254S, or P782L. Also disclosed are arrays comprising polynucleotides capable of specifically hybridizing to c-CBL encoding nucleic acids that comprise a mutation in a nucleic acid sequence encoding human c-CBL, wherein the mutation is located in the TKB domain, RING finger domain, proline-rich region, C-terminal region, or other domain linkage regions of c-CBL. Also disclosed herein are solid supports comprising one or more of the disclosed polynucleotides or polypeptides capable of hybridizing to a mutant form of c-CBL.

Solid supports are solid-state substrates or supports with which molecules, such as analytes and analyte binding molecules, can be associated. Analytes, such as calcifying nano-particles and proteins, can be associated with solid supports directly or indirectly. For example, analytes can be directly immobilized on solid supports. Analyte capture agents, such a capture compounds, can also be immobilized on solid supports. For example, disclosed herein are antigen binding agents capable of specifically binding to a c-CBL polypeptides comprising a mutation at position S80N, H94Y, Q249E, V391I, 72515_72517delATG, W802*, R830K, A848T, L620F, P170L, S171S, L281F, L254S, or P782L. Also disclosed is an antigen binding agent capable of specifically binding to a c-CBL polypeptide comprising a mutation, wherein the mutation is located in the TKB domain, RING finger domain, proline-rich region, C-terminal region, or other domain linkage regions of c-CBL.

A preferred form of solid support is an array. Another form of solid support is an array detector. An array detector is a solid support to which multiple different capture compounds or detection compounds have been coupled in an array, grid, or other organized pattern.

Solid-state substrates for use in solid supports can include any solid material to which molecules can be coupled. This includes materials such as acrylamide, agarose, cellulose, nitrocellulose, glass, polystyrene, polyethylene vinyl acetate, polypropylene, polymethacrylate, polyethylene, polyethylene oxide, polysilicates, polycarbonates, teflon, fluorocarbons, nylon, silicon rubber, polyanhydrides, polyglycolic acid, polylactic acid, polyorthoesters, polypropylfumerate, collagen, glycosaminoglycans, and polyamino acids. Solid-state substrates can have any useful form including thin film, membrane, bottles, dishes, fibers, woven fibers, shaped polymers, particles, beads, microparticles, or a combination. Solid-state substrates and solid supports can be porous or non-porous. A preferred form for a solid-state substrate is a microtiter dish, such as a standard 96-well type. In preferred embodiments, a multiwell glass slide can be employed that normally contain one array per well. This feature allows for greater control of assay reproducibility, increased throughput and sample handling, and ease of automation.

Different compounds can be used together as a set. The set can be used as a mixture of all or subsets of the compounds used separately in separate reactions, or immobilized in an array. Compounds used separately or as mixtures can be physically separable through, for example, association with or immobilization on a solid support. An array can include a plurality of compounds immobilized at identified or predefined locations on the array. Each predefined location on the array generally can have one type of component (that is, all the components at that location are the same). Each location will have multiple copies of the component. The spatial separation of different components in the array allows separate detection and identification of the polynucleotides or polypeptides disclosed herein.

Although preferred, it is not required that a given array be a single unit or structure. The set of compounds may be distributed over any number of solid supports. For example, at one extreme, each compound may be immobilized in a separate reaction tube or container, or on separate beads or microparticles. Different modes of the disclosed method can be performed with different components (for example, different compounds specific for different proteins) immobilized on a solid support.

Some solid supports can have capture compounds, such as antibodies, attached to a solid-state substrate. Such capture compounds can be specific for calcifying nano-particles or a protein on calcifying nano-particles. Captured calcifying nano-particles or proteins can then be detected by binding of a second, detection compound, such as an antibody. The detection compound can be specific for the same or a different protein on the calcifying nano-particle.

Methods for immobilizing antibodies (and other proteins) to solid-state substrates are well established. Immobilization can be accomplished by attachment, for example, to aminated surfaces, carboxylated surfaces or hydroxylated surfaces using standard immobilization chemistries. Examples of attachment agents are cyanogen bromide, succinimide, aldehydes, tosyl chloride, avidin-biotin, photocrosslinkable agents, epoxides and maleimides. A preferred attachment agent is the heterobifunctional cross-linker N-[γ-Maleimidobutyryloxy] succinimide ester (GMBS). These and other attachment agents, as well as methods for their use in attachment, are described in Protein immobilization: fundamentals and applications, Richard F. Taylor, ed. (M. Dekker, New York, 1991); Johnstone and Thorpe, Immunochemistry In Practice (Blackwell Scientific Publications, Oxford, England, 1987) pages 209-216 and 241-242, and Immobilized Affinity Ligands; Craig T. Hermanson et al., eds. (Academic Press, New York, 1992) which are incorporated by reference in their entirety for methods of attaching antibodies to a solid-state substrate. Antibodies can be attached to a substrate by chemically cross-linking a free amino group on the antibody to reactive side groups present within the solid-state substrate. For example, antibodies may be chemically cross-linked to a substrate that contains free amino, carboxyl, or sulfur groups using glutaraldehyde, carbodiimides, or GMBS, respectively, as cross-linker agents. In this method, aqueous solutions containing free antibodies are incubated with the solid-state substrate in the presence of glutaraldehyde or carbodiimide.

A preferred method for attaching antibodies or other proteins to a solid-state substrate is to functionalize the substrate with an amino- or thiol-silane, and then to activate the functionalized substrate with a homobifunctional cross-linker agent such as (Bis-sulfo-succinimidyl suberate (BS$^3$) or a heterobifunctional cross-linker agent such as GMBS. For cross-linking with GMBS, glass substrates are chemically functionalized by immersing in a solution of mercaptopropyltrimethoxysilane (1% vol/vol in 95% ethanol pH 5.5) for 1 hour, rinsing in 95% ethanol and heating at 120° C. for 4 hrs. Thiol-derivatized slides are activated by immersing in a 0.5 mg/ml solution of GMBS in 1% dimethylformamide, 99% ethanol for 1 hour at room temperature. Antibodies or proteins are added directly to the activated substrate, which are then blocked with solutions containing agents such as 2% bovine serum albumin, and air-dried. Other standard immobilization chemistries are known by those of skill in the art.

Each of the components (compounds, for example) immobilized on the solid support preferably is located in a different predefined region of the solid support. Each of the different predefined regions can be physically separated from each other of the different regions. The distance between the different predefined regions of the solid support can be either fixed or variable. For example, in an array, each of the components can be arranged at fixed distances from each other, while components associated with beads will not be in a fixed spatial relationship. In particular, the use of multiple solid support units (for example, multiple beads) will result in variable distances.

Components can be associated or immobilized on a solid support at any density. Components preferably are immobilized to the solid support at a density exceeding 400 different components per cubic centimeter. Arrays of components can have any number of components. For example, an array can have at least 1,000 different components immobilized on the solid support, at least 10,000 different components immobilized on the solid support, at least 100,000 different components immobilized on the solid support, or at least 1,000,000 different components immobilized on the solid support.

Optionally, at least one address on the solid support is the sequences or part of the sequences set forth in any of the nucleic acid sequences disclosed herein. Also disclosed are solid supports where at least one address is the sequences or portion of sequences set forth in any of the peptide sequences disclosed herein. Solid supports can also contain at least one address is a variant of the sequences or part of the sequences set forth in any of the nucleic acid sequences disclosed herein. Solid supports can also contain at least one address is a variant of the sequences or portion of sequences set forth in any of the peptide sequences disclosed herein.

Also disclosed are antigen microarrays for multiplex characterization of antibody responses. For example, disclosed are antigen arrays and miniaturized antigen arrays to perform large-scale multiplex characterization of antibody responses directed against the polypeptides, polynucleotides and antibodies described herein, using submicroliter quantities of biological samples as described in Robinson et al., Autoantigen microarrays for multiplex characterization of autoantibody responses, Nat Med., 8(3):295-301 (2002), which in herein incorporated by reference in its entirety for its teaching of contructing and using antigen arrays to perform large-scale multiplex characterization of antibody responses directed against structurally diverse antigens, using submicroliter quantities of biological samples.

Protein variants and derivatives are well understood to those of skill in the art and can involve amino acid sequence modifications. For example, amino acid sequence modifications typically fall into one or more of three classes: substitutional, insertional or deletional variants. Polypeptide variants generally encompassed by the present invention will typically exhibit at least about 70%, 75%, 80%, 85%, 90%, 91%, 92%, 93%, 94%, 95%, 96%, 97%, 98%, or 99% or more identity (determined as described below), along its length, to a polypeptide sequences set forth herein.

Also disclosed are expression vectors comprising the polynucleotides described elsewhere herein. For example, disclosed are expression vectors comprising the polynucleotides described elsewhere herein, operably linked to a control element. Also disclosed herein are host cells transformed or transfected with an expression vector comprising the polynucleotides described elsewhere herein. Also disclosed are host cells comprising the expression vectors described herein. For example, disclosed is a host cell comprising an expression vector comprising the polynucleotides described elsewhere herein, operably linked to a control element. Host cells can be eukayotic or prokaryotic cells.

Expression vectors can be any nucleotide construction used to deliver genes into cells (e.g., a plasmid), or as part of a general strategy to deliver genes, e.g., as part of recombinant retrovirus or adenovirus (Ram et al. Cancer Res. 53:83-88, (1993)). For example, disclosed herein are expression vectors comprising an isolated polynucleotide comprising a sequence of one or more of the c-CBL mutants described herein, operably linked to a control element.

As used herein, plasmid or viral vectors are agents that transport the disclosed nucleic acids, such as an isolated polynucleotide capable of encoding one or more polypeptides disclosed herein into the cell without degradation and include a promoter yielding expression of the gene in the cells into which it is delivered. In some embodiments the isolated polynucleotides disclosed herein are derived from either a virus or a retrovirus.

As described herein, the compositions can be administered in a pharmaceutically acceptable carrier and can be delivered to the subject's cells in vivo or ex vivo by a variety of mechanisms well known in the art (e.g., uptake of naked DNA, liposome fusion, intramuscular injection of DNA via a gene gun, endocytosis and the like).

If ex vivo methods are employed, cells or tissues can be removed and maintained outside the body according to standard protocols well known in the art. The compositions can be introduced into the cells via any gene transfer mechanism, such as, for example, calcium phosphate mediated gene delivery, electroporation, microinjection or proteoliposomes. The transduced cells can then be infused (e.g., in a pharmaceutically acceptable carrier) or homotopically transplanted back into the subject per standard methods for the cell or tissue type. Standard methods are known for transplantation or infusion of various cells into a subject.

The nucleic acids, such as, the polynucleotides described herein, can be made using standard chemical synthesis methods or can be produced using enzymatic methods or any other known method. Such methods can range from standard enzymatic digestion followed by nucleotide fragment isolation (see for example, Sambrook et al., Molecular Cloning: A Laboratory Manual, 3rd Edition (Cold Spring Harbor Laboratory Press, Cold Spring Harbor, N.Y., 2001) Chapters 5, 6) to purely synthetic methods, for example, by the cyanoethyl phosphoramidite method using a Milligen or Beckman System 1Plus DNA synthesizer. Synthetic methods useful for making oligonucleotides are also described by Ikuta et al., Ann. Rev. Biochem. 53:323-356 (1984), (phosphotriester and phosphite-triester methods), and Narang et al., Methods Enzymol., 65:610-620 (1980), (phosphotriester method). Protein nucleic acid molecules can be made using known methods such as those described by Nielsen et a., Bioconjug. Chem. 5:3-7 (1994).

The invention also provides polypeptides related to c-CBL. As used herein, the term "polypeptide" is used in its conventional meaning, i.e., as a sequence of amino acids. The polypeptides are not limited to a specific length of the product; thus, peptides, oligopeptides, and proteins are included within the definition of polypeptide, and such terms may be used interchangeably herein unless specifically indicated otherwise. This term also does not refer to or exclude post-expression modifications of the polypeptide, for example, glycosylations, acetylations, phosphorylations and the like, as well as other modifications known in the art, both naturally occurring and non-naturally occurring. A polypeptide may be an entire protein, or a subsequence thereof. Particular polypeptides of interest in the context of this invention are amino acid subsequences comprising epitopes, i.e., antigenic determinants substantially responsible for the immunogenic properties of a polypeptide and being capable of evoking an immune response.

Thus, a "c-CBL polypeptide" or "c-CBL protein," refers generally to a polypeptide sequence that is present in samples isolated from normal subjects as well as a substantial proportion of subjects with a cancer, for example preferably greater than about 20%, more preferably greater than about 30%, and most preferably greater than about 50% or more of subjects tested as determined using a representative assay provided herein. A polypeptide sequence of the invention, based upon its expression in a cancer sample isolated from individuals with a cancer, has particular utility both as a diagnostic, prognostic and/or theranostic marker as well as a therapeutic target, as further described below.

For example, disclosed herein are polypeptides comprising an amino acid sequence encoded by the polynucleotides described elsewhere herein. For example, disclosed are isolated polypeptides comprising amino acid sequences disclosed herein. Also disclosed are isolated polynucleotides capable of encoding one or more polypeptides selected from the group consisting of the polypeptides disclosed herein, or a complement thereof.

The polypeptides of the present invention are sometimes herein referred to as c-CBL proteins or c-CBL polypeptides, as an indication that their identification has been based at least in part upon their expression in cancer samples isolated from tissues of a subject with lung cancer or head and neck cancer. The peptides described herein are identified from tissues for a subject with either lung cancer and head and neck cancer. Accordingly, such a peptide may not be present in adjacent normal tissue. However, non-mutant forms of the polynucleotides and polypeptides can be found in normal tissue.

Additionally, polypeptides described herein may be identified by their different reactivity with sera from subjects with cancer as compared to sera from unaffected individuals. For example, polypeptides described herein may be identified by their reactivity with sera from subjects with a cancer as compared to their lack of reactivity to sera from unaffected individuals. Additionally, polypeptides described herein may be identified by their reactivity with sera from subjects with cancer as compared to their higher reactivity to sera from unaffected individuals. Additionally, polypeptides described herein may be identified by their reactivity with sera from subjects with a cancer as compared to their lower reactivity to sera from unaffected individuals.

Also disclosed herein are antigen binding agents capable of specifically binding to a c-CBL polypeptide comprising a mutation at position S80N, H94Y, Q249E, V391I, 72515_72517delATG, W802*, R830K, A848T, L620F, P170L, S171S, L281F, L254S, or P782L. Also disclosed is an antigen binding agent capable of specifically binding to a c-Met polypeptide comprising a mutation in a nucleic acid sequence encoding human c-CBL, wherein the mutation is located in the TKB domain, RING finger domain, proline-rich region, C-terminal region, or other domain linkage regions of c-CBL.

Also disclosed are isolated polypeptides comprising the sequence provided herein as well as the Figures, with substituted, inserted or deletional variations.

As this specification discusses various polypeptides and polypeptide sequences it is understood that the nucleic acids that can encode those polypeptide sequences are also disclosed. This would include all degenerate sequences related to a specific polypeptide sequence, i.e. all nucleic acids having a sequence that encodes one particular polypeptide sequence as well as all nucleic acids, including degenerate nucleic acids, encoding the disclosed variants and derivatives of the protein sequences. Thus, while each particular nucleic acid sequence may not be written out herein, it is understood that each and every sequence is in fact disclosed and described herein through the disclosed polypeptide sequences.

Also disclosed herein are isolated antibodies, antibody fragments and antigen-binding fragments thereof, that specifically bind to a polypeptide sequence described herein. Optionally, the isolated antibodies, antibody fragments, or antigen-binding fragment thereof can be neutralizing antibodies. The antibodies, antibody fragments and antigen-binding fragments thereof disclosed herein can be identified using the methods disclosed herein. For example, antibodies that bind to the polypeptides of the invention can be isolated using the antigen microarray described above.

The term "antibodies" is used herein in a broad sense and includes both polyclonal and monoclonal antibodies. In addition to intact immunoglobulin molecules, also disclosed are antibody fragments or polymers of those immunoglobulin molecules, and human or humanized versions of immunoglobulin molecules or fragments thereof, as long as they are chosen for their ability to interact with the polypeptides disclosed herein.

"Antibody fragments" are portions of a complete antibody. A complete antibody refers to an antibody having two complete light chains and two complete heavy chains. An antibody fragment lacks all or a portion of one or more of the chains. Examples of antibody fragments include, but are not limited to, half antibodies and fragments of half antibodies. A half antibody is composed of a single light chain and a single heavy chain. Half antibodies and half antibody fragments can be produced by reducing an antibody or antibody fragment having two light chains and two heavy chains. Such antibody fragments are referred to as reduced antibodies. Reduced antibodies have exposed and reactive sulfhydryl groups. These sulfhydryl groups can be used as reactive chemical groups or coupling of biomolecules to the antibody fragment. A preferred half antibody fragment is a F(ab). The hinge region of an antibody or antibody fragment is the region where the light chain ends and the heavy chain goes on.

Antibody fragments for use in antibody conjugates can bind antigens. Preferably, the antibody fragment is specific for an antigen. An antibody or antibody fragment is specific for an antigen if it binds with significantly greater affinity to one epitope than to other epitopes. The antigen can be any molecule, compound, composition, or portion thereof to which an antibody fragment can bind. An analyte can be any molecule, compound or composition of interest. For example, the antigen can be a polynucleotide of the invention.

The antibodies or antibody fragments can be tested for their desired activity using the in vitro assays described herein, or by analogous methods, after which their in vivo therapeutic or prophylactic activities are tested according to known clinical testing methods.

The term "monoclonal antibody" as used herein refers to an antibody obtained from a substantially homogeneous population of antibodies, i.e., the individual antibodies within the population are identical except for possible naturally occurring mutations that may be present in a small subset of the antibody molecules. Also disclosed are "chimeric" antibodies in which a portion of the heavy or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, as long as they exhibit the desired antagonistic activity (See, U.S. Pat. No. 4,816,567 and Morrison et al., Proc. Natl. Acad. Sci. USA, 81:6851-6855 (1984)).

The disclosed monoclonal antibodies can be made using any procedure which produces monoclonal antibodies. For example, disclosed monoclonal antibodies can be prepared using hybridoma methods, such as those described by Kohler and Milstein, Nature, 256:495 (1975). In a hybridoma method, a mouse or other appropriate host animal is typically immunized with an immunizing agent to elicit lymphocytes that produce or are capable of producing antibodies that will specifically bind to the immunizing agent. Alternatively, the lymphocytes may be immunized in vitro, e.g., using the HIV Env-CD4-co-receptor complexes described herein.

The monoclonal antibodies may also be made by recombinant DNA methods, such as those described in U.S. Pat. No. 4,816,567 (Cabilly et al.). DNA encoding the disclosed monoclonal antibodies can be readily isolated and sequenced using conventional procedures (e.g., by using oligonucleotide probes that are capable of binding specifically to genes encoding the heavy and light chains of murine antibodies). Libraries of antibodies or active antibody fragments can also be generated and screened using phage display techniques, e.g., as described in U.S. Pat. No. 5,804,440 to Burton et al. and U.S. Pat. No. 6,096,441 to Barbas et al.

In vitro methods are also suitable for preparing monovalent antibodies. Digestion of antibodies to produce fragments thereof, such as an Fv, Fab, Fab', or other antigen-binding portion of an antibody, can be accomplished using routine techniques known in the art. For instance, digestion can be performed using papain. Examples of papain digestion are described in WO 94/29348 published Dec. 22, 1994 and U.S. Pat. No. 4,342,566 which is hereby incorporated by reference in its entirety for its teaching of papain digestion of antibodies to prepare monovaltent antibodies. Papain digestion of antibodies typically produces two identical antigen binding fragments, called Fab fragments, each with a single antigen binding site, and a residual Fc fragment. Pepsin treatment yields a fragment that has two antigen combining sites and is still capable of cross-linking antigen.

The fragments, whether attached to other sequences, can also include insertions, deletions, substitutions, or other selected modifications of particular regions or specific amino acids residues, provided the activity of the antibody or antibody fragment is not significantly altered or impaired compared to the non-modified antibody or antibody fragment. These modifications can provide for some additional property, such as to remove/add amino acids capable of disulfide bonding, to increase its bio-longevity, to alter its secretory characteristics, etc. In any case, the antibody or antibody fragment must possess a bioactive property, such as specific binding to its cognate antigen. Functional or active regions of the antibody or antibody fragment may be identified by mutagenesis of a specific region of the protein, followed by expression and testing of the expressed polypeptide. Such methods are readily apparent to a skilled practitioner in the art and can include site-specific mutagenesis of the nucleic acid encoding the antibody or antibody fragment. (Zoller, M. J. Curr. Opin. Biotechnol. 3:348-354, 1992).

As used herein, the term "antibody" or "antibodies" can also refer to a human antibody or a humanized antibody. Many non-human antibodies (e.g., those derived from mice, rats, or rabbits) are naturally antigenic in humans, and thus can give rise to undesirable immune responses when administered to humans. Therefore, the use of human or humanized antibodies in the methods serves to lessen the chance that an antibody administered to a human will evoke an undesirable immune response.

The disclosed human antibodies can be prepared using any technique. Examples of techniques for human monoclonal antibody production include those described by Cole et al. (Monoclonal Antibodies and Cancer Therapy, Alan R. Liss, p. 77, 1985) and by Boerner et al. (J. Immunol., 147(1):86-95, 1991). Human antibodies (and fragments thereof) can also be produced using phage display libraries (Hoogenboom et al., J. Mol. Biol., 227:381, 1991; Marks et al., J. Mol. Biol., 222:581, 1991).

The disclosed human antibodies can also be obtained from transgenic animals. For example, transgenic, mutant mice that are capable of producing a full repertoire of human antibodies, in response to immunization, have been described (see, e.g., Jakobovits et al., Proc. Natl. Acad. Sci. USA, 90:2551-255 (1993); Jakobovits et al., Nature, 362: 255-258 (1993); Bruggermann et al., Year in Immunol., 7:33 (1993)). Specifically, the homozygous deletion of the antibody heavy chain joining region (J(H)) gene in these chimeric and germ-line mutant mice results in complete inhibition of endogenous antibody production, and the successful transfer of the human germ-line antibody gene array into such germ-line mutant mice results in the production of human antibodies upon antigen challenge. Antibodies having the desired activity are selected using Env-CD4-co-receptor complexes as described herein.

Optionally, the disclosed human antibodies can be made from memory B cells using a method for Epstein-Barr virus transformation of human B cells. (See, e.g., Triaggiai et al., An efficient method to make human monoclonal antibodies from memory B cells: potent neutralization of SARS coronavirus, Nat Med. 2004 August; 10(8):871-5. (2004)), which is herein incorporated by reference in its entirety for its teaching of a method to make human monoclonal antibodies from memory B cells). In short, memory B cells from a subject who has survived a natural infection are isolated and immortalized with EBV in the presence of irradiated mononuclear cells and a CpG oligonucleotide that acts as a polyclonal activator of memory B cells. The memory B cells are cultured and analyzed for the presence of specific antibodies. EBV-B cells from the culture producing the antibodies of the desired specificity are then cloned by limiting dilution in the presence of irradiated mononuclear cells, with the addition of CpG 2006 to increase cloning efficiency, and cultured. After culture of the EBV-B cells, monoclonal antibodies can be isolated. Such a method offers (1) antibodies that are produced by immortalization of memory B lymphocytes which are stable over a lifetime and can easily be isolated from peripheral blood and (2) the antibodies isolated from a primed natural host who has survived a natural infection, thus eliminating the need for immunization of experimental animals, which may show different susceptibility and, therefore, different immune responses.

Antibody humanization techniques generally involve the use of recombinant DNA technology to manipulate the DNA sequence encoding one or more polypeptide chains of an antibody molecule. Accordingly, a humanized form of a non-human antibody (or a fragment thereof) is a chimeric antibody or antibody chain (or a fragment thereof, such as an Fv, Fab, Fab', or other antigen-binding portion of an antibody) which contains a portion of an antigen binding site from a non-human (donor) antibody integrated into the framework of a human (recipient) antibody.

To generate a humanized antibody, residues from one or more complementarity determining regions (CDRs) of a recipient (human) antibody molecule are replaced by residues from one or more CDRs of a donor (non-human) antibody molecule that is known to have desired antigen binding characteristics (e.g., a certain level of specificity and affinity for the target antigen). In some instances, Fv framework (FR) residues of the human antibody are replaced by corresponding non-human residues. Humanized antibodies may also contain residues which are found neither in the recipient antibody nor in the imported CDR or framework sequences. Generally, a humanized antibody has one or more amino acid residues introduced into it from a source which is non-human. In practice, humanized antibodies are typically human antibodies in which some CDR residues and possibly some FR residues are substituted by residues from analogous sites in rodent antibodies. Humanized antibodies generally contain at least a portion of an antibody constant region (Fc), typically that of a human antibody (Jones et al., Nature, 321:522-525 (1986), Reichmann et al., Nature, 332:323-327 (1988), and Presta, Curr. Opin. Struct. Biol., 2:593-596 (1992)).

Methods for humanizing non-human antibodies are well known in the art. For example, humanized antibodies can be generated according to the methods of Winter and co-workers (Jones et al., Nature, 321:522-525 (1986), Riechmann et al., Nature, 332:323-327 (1988), Verhoeyen et al., Science, 239:1534-1536 (1988)), by substituting rodent CDRs or CDR sequences for the corresponding sequences of a human antibody. Methods that can be used to produce humanized antibodies are also described in U.S. Pat. No. 4,816,567 (Cabilly et al.), U.S. Pat. No. 5,565,332 (Hoogenboom et al.), U.S. Pat. No. 5,721,367 (Kay et al.), U.S. Pat. No. 5,837,243 (Deo et al.), U.S. Pat. No. 5,939,598 (Kucherlapati et al.), U.S. Pat. No. 6,130,364 (Jakobovits et al.), and U.S. Pat. No. 6,180,377 (Morgan et al.).

The antibodies disclosed herein can also be administered to a subject. Nucleic acid approaches for antibody delivery also exist. The broadly neutralizing antibodies to the polypeptides disclosed herein and antibody fragments can also be administered to subjects or subjects as a nucleic acid preparation (e.g., DNA or RNA) that encodes the antibody or antibody fragment, such that the subject's own cells take up the nucleic acid and produce and secrete the encoded antibody or antibody fragment.

The disclosed compositions and methods can also be used for example as tools to isolate and test new drug candidates for a variety of cancers, including, but not limited to lung cancer.

In addition, the compositions described herein may be used as markers for presence or progression of cancers. The methods and assays described elsewhere herein may be performed over time, and the change in the level of reactive polypeptide(s) or polynucleotide(s) evaluated. For example, the assays may be performed every 24-72 hours for a period of 6 months to 1 year, and thereafter performed as needed. For example, immunoreactivity to a given polypeptide in individuals with cancer can correlate with or predict the development of complications, more severe activity of disease.

As noted herein, to improve sensitivity, multiple mutations may be assayed within a given sample. Binding agents specific for different proteins, antibodies, nucleic acids thereto provided herein may be combined within a single assay. Further, multiple primers or probes may be used concurrently. The selection of c-CBL proteins or genes may be based on routine experiments to determine combinations that results in optimal sensitivity. In addition, or alternatively, assays for mutated c-CBL, antibodies, or nucleic acids specific thereto, provided herein may be combined with assays for other known cancer markers or other genetic markers in subjects with cancer. To assist with such assays, specific biomarkers can assist in the specificity of such tests. As such, disclosed herein is a cancer biomarker, wherein the biomarker comprises c-CBL comprising a mutation that results in an amino acid change at position S80N, H94Y, Q249E, V391I, 72515_72517delATG, W802*, R830K, A848T, L620F, P170L, S171S, L281F, L254S, or P782L. Also disclosed is a cancer biomarker, wherein the biomarker comprises c-CBL comprising a mutation in a nucleic acid sequence encoding human c-CBL, wherein the mutation is located in the TKB domain, RING finger domain, proline-rich region, C-terminal region, or other domain linkage regions of c-CBL.

The biomarkers described herein can be in any form that provides information regarding presence or absence of a mutation of the invention. For example, the disclosed biomarkers can be, but is not limited to a nucleic acid molecule, a polypeptide, or an antibody.

Also disclosed are cancer imaging agents, wherein the agent specifically binds c-CBL comprising a mutation, wherein the agent binds a c-CBL polypeptide comprising a mutation at position S80N, H94Y, Q249E, V391I, 72515_72517delATG, W802*, R830K, A848T, L620F, P170L, S171S, L281F, L254S, or P782L72515_72517delATG.

The disclosed compositions and methods can be used for targeted gene disruption and modification in any animal that can undergo these events. Gene modification and gene disruption refer to the methods, techniques, and compositions that surround the selective removal or alteration of a gene or stretch of chromosome in an animal, such as a mammal, in a way that propagates the modification through the germ line of the mammal. In general, a cell is transformed with a vector which is designed to homologously recombine with a region of a particular chromosome contained within the cell, as for example, described herein. This homologous recombination event can produce a chromosome which has exogenous DNA introduced, for example in frame, with the surrounding DNA. This type of protocol allows for very specific mutations, such as point mutations, to be introduced into the genome contained within the cell. Methods for performing this type of homologous recombination are disclosed herein.

One of the preferred characteristics of performing homologous recombination in mammalian cells is that the cells should be able to be cultured, because the desired recombination events occur at a low frequency.

Once a cell is produced through the methods described herein, an animal can be produced from this cell through either stem cell technology or cloning technology. For example, if the cell into which the nucleic acid was transfected was a stem cell for the organism, then this cell, after transfection and culturing, can be used to produce an organism which will contain the gene modification or disruption in germ line cells, which can then in turn be used to produce another animal that possesses the gene modification or disruption in all of its cells. In other methods for production of an animal containing the gene modification or disruption in all of its cells, cloning technologies can be used. These technologies generally take the nucleus of the transfected cell and either through fusion or replacement fuse the transfected nucleus with an oocyte which can then be manipulated to produce an animal. The advantage of procedures that use cloning instead of ES technology is that cells other than ES cells can be transfected. For example, a fibroblast cell, which is very easy to culture can be used as the cell which is transfected and has a gene modification or disruption event take place, and then cells derived from this cell can be used to clone a whole animal.

Disclosed herein are transgenic animals comprising mutations in a nucleotide sequence capable of encoding a c-CBL protein. Transgenic animals include, but are not limited to zebrafish and nematodes. It is also understood that the animal can comprise any mammal. For example, the animal can be a mouse, vole, rat, guinea pig, cat, dog, cow, sheep pig, monkey, or human. For example, disclosed are transgenic animal comprising one or more of the disclosed c-CBL mutations including, but not limited to c-CBL encoding nucleic acids comprising a mutation at a nucleic acid position corresponding to a change in amino acid at position S80N, H94Y, Q249E, V391I, 72515_72517delATG, W802*, R830K, A848T, L620F, P170L, S171S, L281F, L254S, or P782L. Also disclosed are transgenic animals comprising one or more of the disclosed c-CBL mutations including, but not limited to c-CBL encoding nucleic acids that comprises a mutation in a nucleic acid sequence encoding human c-CBL, wherein the mutation is located in the TKB domain, RING finger domain, proline-rich region, or the C-terminal region of c-CBL.

It is understood that the disclosed nucleic acids and proteins can be represented as a sequence consisting of the nucleotides of amino acids. There are a variety of ways to display these sequences, for example the nucleotide guanosine can be represented by G or g. Likewise the amino acid valine can be represented by Val or V. Those of skill in the art understand how to display and express any nucleic acid or protein sequence in any of the variety of ways that exist, each of which is considered herein disclosed. Specifically contemplated herein is the display of these sequences on computer readable mediums, such as, commercially available floppy disks, tapes, chips, hard drives, compact disks, and video disks, or other computer readable mediums. Also disclosed are the binary code representations of the disclosed sequences. Those of skill in the art understand what computer readable mediums. Thus, computer readable mediums on which the nucleic acids or protein sequences are recorded, stored, or saved.

Disclosed are computer readable mediums comprising the sequences and information regarding the sequences set forth herein. Also disclosed are computer readable mediums comprising the sequences and information regarding the sequences set forth herein.

Also disclosed herein is a computer-readable medium comprising human c-CBL amino acid polypeptide sequence comprising a mutation at position S80N, H94Y, Q249E, V391I, 72515_72517delATG, W802*, R830K, A848T, L620F, P170L, S171S, L281F, L254S, or P782L and/or nucleic acid sequence encoding a human c-CBL polypeptide comprising a mutation at a nucleic acid position corresponding to a change in amino acid at position S80N, H94Y, Q249E, V391I, 72515_72517delATG, W802*, R830K, A848T, L620F, P170L, S171S, L281F, L254S, or P782L. Further disclosed is a computer-readable medium comprising human c-CBL amino acid polypeptide sequence comprising a mutation in a nucleic acid sequence encoding human c-CBL, wherein the sequence comprises a mutation in a nucleic acid sequence encoding human c-CBL, wherein the mutation is located in the TKB domain, RING finger domain, proline-rich region, C-terminal region, or other domain linkage regions of c-CBL.

The computer-readable mediums disclosed herein can comprise a storage medium for sequence information for one or more subjects. For example, the information can be a personalized genomic profile for a subject known or suspected to have a cancer, wherein the genomic profile comprises sequence information for c-CBL comprising one or more of the mutations disclosed herein.

The present invention therefore also provides predictive, diagnostic, and prognostic kits comprising degenerate primers to amplify a target nucleic acid in the c-CBL gene and instructions comprising amplification protocol and analysis of the results. The kit may alternatively also comprise buffers, enzymes, and containers for performing the amplification and analysis of the amplification products. The kit may also be a component of a screening, diagnostic or prognostic kit comprising other tools such as DNA microarrays. Preferably, the kit also provides one or more control templates, such as nucleic acids isolated from normal tissue sample, and/or a series of samples representing different variances in the c-CBL gene.

In one embodiment, the kit provides two or more primer pairs, each pair capable of amplifying a different region of the c-CBL gene (each region a site of potential variance) thereby providing a kit for analysis of expression of several gene variances in a biological sample in one reaction or several parallel reactions. Primers in the kits may be labeled, for example fluorescently labeled, to facilitate detection of the amplification products and consequent analysis of the nucleic acid variances. For example, the primers can be one or more of the primers of Table 3.

In one embodiment, more than one variance can be detected in one analysis. A combination kit will therefore comprise of primers capable of amplifying different segments of the kinase domain of the c-CBL gene. For example, the primers can be one or more of the primers of Table 3. The primers may be differentially labeled, for example using different fluorescent labels, so as to differentiate between the variances. The primers contained within the kit may include primers selected from complementary sequences to the coding sequence of c-CBL. For example, the primers can be one or more of the primers of Table 1.

In further embodiments, the invention provides immunological kits for use in detecting the activation levels of downstream targets of c-CBL's E3 ubiquitination activity.

The kit generally comprises, a) a pharmaceutically acceptable carrier; b) an c-MET and Ubiquitin antibody directed against a downstream targets of c-CBL's E3 ubiquitination activity; and c) an immunodetection reagent. Antibodies (monoclonal or polyclonal) are commercially available and may also be prepared by methods known to those of skill in the art, for example, in Current Protocols in Immunology, John Wiley & Sons, Edited by: John E. Coligan, Ada M. Kruisbeek, David H. Margulies, Ethan M. Shevach, Warren Strober, 2001.

The immunodetection kits of the invention may additionally contain one or more of a variety of other cancer marker antibodies or antigens, if so desired. Such kits could thus provide a panel of cancer markers, as may be better used in testing a variety of patients. By way of example, such additional markers could include, other tumor markers such as PSA, SeLe (X), HCG, as well as p53, cyclin D1, p16, tyrosinase, MAGE, BAGE, PAGE, MUC 18, CEA, p27, [bgr]HCG or other markers known to those of skill in the art.

The container means of the kits will generally include at least one vial, test tube, flask, bottle, or even syringe or other container means, into which the antibody or antigen may be placed, and preferably, suitably aliquoted. Where a second or third binding ligand or additional component is provided, the kit will also generally contain a second, third or other additional container into which this ligand or component may be placed. The kits of the present invention will also typically include a means for containing the antibody, antigen, and any other reagent containers in close confinement for commercial sale. Such containers may include injection or blow-molded plastic containers into which the desired vials are retained.

Methods

The disclosed compositions, including the c-CBL mutations disclosed herein can be used in a variety of different methods, for example in prognostic, predictive, diagnostic, and therapeutic methods and as a variety of different compositions. For example, disclosed herein are methods of identifying a subject that is susceptible to treatment with a c-Met inhibitor comprising determining whether a sample from the subject comprises a mutation in a nucleic acid sequence encoding human c-CBL.

Due to the vast information supporting the role of c-Met and HGF in the pathogenesis of human cancers along with successes of other RTK inhibitors, a number of approaches have been attempted to inhibit HGF- or c-Met-dependent signaling. These approaches include: (1) c-Met biologic inhibitors (ribozymes, dominant-negative receptors, decoy receptors, peptides); (2) HGF kringle variant antagonists; (3) HGF antagonist antibodies; (4) c-Met antagonist antibodies; and (5) small-molecule c-Met inhibitors. To date, several possible c-Met inhibitors have been developed with the intent on either silencing, or decreasing c-Met expression or decreasing c-Met activity. For example, Compound X, PHA665752 (Pfizer, Inc.), SU11274 (Sugen, Inc.), SU11271 (Sugen, Inc.), SU11606 (Sugen, Inc.), ARQ197 (ArQuleArqule, Inc.), MP470 (Supergen, Inc.), Kirin, XL-880 (Exelixis, Inc.), XL184 (Exelixis, Inc.) Geldanamycins, SGX523 (SGX, Inc.), MGCD265 (MethylGene, Inc.), HPK-56 (Supergen, Inc.), AMG102 (Amgen, Inc.), MetMAb (Genentech, Inc.), ANG-797 (Angion Biomedica Corp.), CGEN-241 (Compugen LTD.), Metro-F-1 (Dompe S.p.A.), ABT-869 (Abbott Laboratories) and K252a are all c-Met inhibitors currently being produced. In addition, h224G11 (Abbott), ARQ197 (ArQule), AMG208 (Amgen), BMS907351 (Bristol-Myers Squibb Company), DP3590 (Deciphera Pharmaceuticals), DP4157 (Deciphera Pharmaceuticals, LLC), E7050 (Eisai Co.), SGX523 (Eli Lilly), XL880 (Exelixis), XL184 (Exelixis), RG3638 (MetMab), GSK1363089 (GlaxoSmithKline), INCB28060 (Incyte), MK2461 (Merck & Co), EMD1204831 (Merck KGaA), EMD1214063 (Merck Serono S.A.), MGCD265 (MethylGene), PF2341066 (Pfizer), MP470 (SuperGen), AMG102 (Amgen), ABT-869 (Abbott Laboratories), ANG-797 (Angion Biomedica Corp), CGEN-241 (Compugen LTD), PHA665752 (Pfizer), SU11274 (Sugen), SU11271 (Sugen), SU11606 (Sugen), HPK-56 (Supergen), K252a (Merck) are also c-Met inhibitors currently being produced.

Cancers or cancer tissues that can be used in the disclosed methods include, but are not limited to, lymphoma (Hodgkins and non-Hodgkins) B-cell lymphoma, T-cell lymphoma, leukemia such as myeloid leukemia and other types of leukemia, mycosis fungoide, carcinoma, adenocarcinoma, sarcoma, glioma, astrocytoma, blastoma, neuroblastoma, plasmacytoma, histiocytoma, melanoma, adenoma, hypoxic tumour, myeloma, AIDS-related lymphoma or AIDS-related sarcoma, metastatic cancer, bladder cancer, brain cancer, nervous system cancer, squamous cell carcinoma of the head and neck, neuroblastoma, glioblastoma, ovarian cancer, skin cancer, liver cancer, squamous cell carcinomas of the mouth, throat, larynx, and lung, colon cancer, cervical cancer, breast cancer, cervical carcinoma, epithelial cancer, renal cancer, genitourinary cancer, pulmonary cancer, esophageal carcinoma, lung cancer, head and neck carcinoma, hematopoietic cancer, testicular cancer, colo-rectal cancer, prostatic cancer, and pancreatic cancer. Specific lung cancers that can be used in the disclosed methods include, but are not limited to Non-Small Cell Lung Cancers (NSCLC) and/or Small Cell Carcinomas (SCC).

While some candidates appear to be successful in inhibiting wild-type c-Met in vitro, it is unknown how c-met inhibitors will affect a subject.

Disclosed herein are methods of identifying a subject that is susceptible to treatment with a c-Met inhibitor comprising determining whether a sample from the subject comprises a mutation in a nucleic acid sequence encoding human c-CBL, wherein the mutation results in an amino acid change at position S80N, H94Y, Q249E, V391I, 72515_72517delATG, W802*, R830K, A848T, L620F, P170L, S171S, L281F, L254S, or P782L. The presence of a mutation in a nucleic acid sequence encoding human c-CBL can then identify a subject that is susceptible to treatment with a c-Met inhibitor.

Also disclosed are methods of identifying a subject that is susceptible to treatment with a c-Met inhibitor comprising determining whether a sample from the subject comprises a mutation in a nucleic acid sequence encoding human c-CBL, wherein the mutation is located in the TKB domain, RING finger domain, proline-rich region, C-terminal region, or other domain linkage regions of c-CBL. For example, the absence of a mutation in a nucleic acid sequence encoding human c-CBL identifies a subject that is not susceptible to treatment with a c-Met inhibitor. In some aspects, the presence of a mutation in a nucleic acid sequence encoding human c-CBL identifies a subject that is susceptible to treatment with a c-Met inhibitor. The mutation located in the TKB domain, RING finger domain, proline-rich region, C-terminal region, or other domain linkage regions of c-CBL can be, but is not limited to a mutation results in an amino acid change at position S80N, H94Y, Q249E, V391I, 72515_72517delATG, W802*, R830K, A848T, L620F, P170L, S171S, L281F, L254S, or P782L.

Also disclosed are methods of identifying a cancer that is susceptible to treatment with a c-Met inhibitor, comprising determining whether a sample from the cancer comprises a mutation in a nucleic acid sequence encoding human c-CBL. For example, in some aspects, the absence of a mutation in a nucleic acid sequence encoding human c-CBL can identify a subject that is not susceptible to treatment with a c-Met inhibitor. In other aspects, the presence of a mutation in a nucleic acid sequence encoding human c-CBL can a subject that is susceptible to treatment with a c-Met inhibitor.

Also disclosed are methods of determining responsiveness of a cancer in a subject to treatment with a c-Met inhibitor, said method comprising determining whether a cancer sample from a subject who has been treated with the c-Met inhibitor comprises a mutation in a nucleic acid sequence encoding human c-CBL, wherein the mutation results in an amino acid change at position S80N, H94Y, Q249E, V391I, 72515_72517delATG, W802*, R830K, A848T, L620F, P170L, S171S, L281F, L254S, or P782L, wherein presence of the mutated nucleic acid sequence is indicative that the cancer is responsive to treatment with the c-Met inhibitor.

Also disclosed are methods of determining responsiveness of a cancer in a subject to treatment with a c-Met inhibitor, said method comprising determining whether a cancer sample comprises a mutation in a nucleic acid sequence encoding human c-CBL, wherein the mutation is located in the TKB domain, RING finger domain, proline-rich region, C-terminal region, or other domain linkage regions of c-CBL, wherein presence of the mutated nucleic acid sequence is indicative that the cancer is responsive to treatment with the c-Met inhibitor.

Also disclosed are methods of detecting cancer in a sample comprising determining whether the sample comprises a mutation in a nucleic acid sequence encoding human c-CBL, wherein the mutation results in an amino acid change at position S80N, H94Y, Q249E, V391I, 72515_72517delATG, W802*, R830K, A848T, L620F, P170L, S171S, L281F, L254S, or P782L.

Also disclosed are methods of detecting cancer in a sample comprising determining whether the sample comprises a mutation in a nucleic acid sequence encoding human c-CBL, wherein the mutation is located in the TKB domain, RING finger domain, proline-rich region, C-terminal region, or other domain linkage regions of the nucleic acid sequence encoding human c-CBL.

Susceptibility can either mean that the cancer sample comprising a mutation in a nucleic acid sequence encoding human c-CBL, wherein the mutation results in an amino acid change at position S80N, H94Y, Q249E, V391I, 72515_72517delATG, W802*, R830K, A848T, L620F, P170L, S171S, L281F, L254S, or P782L, is less responsive to a c-Met inhibitor or more responsive to a c-Met inhibitor.

Also disclosed are methods of identifying a subject that is susceptible to treatment with a c-Met inhibitor comprising determining the level of c-CBL expression in a sample from the subject. For example, disclosed are methods of identifying a subject that is susceptible to treatment with a c-Met inhibitor comprising determining the level of c-CBL expression in a sample from the subject, wherein low levels of c-CBL expression identify a subject that is susceptible to treatment with a c-Met inhibitor. "low levels" of c-CBL expression can mean levels that are below normal levels of c-CBL expression.

Also disclosed are methods of identifying a subject that is susceptible to treatment with a c-Met inhibitor comprising determining the level of c-CBL expression in a sample from the subject, wherein high levels of c-CBL expression identify a subject that is not susceptible to treatment with a c-Met inhibitor. "High levels" of c-CBL expression can mean levels that are equal or above normal levels of c-CBL expression.

Also disclosed are methods of determining responsiveness of a cancer in a subject to treatment with a c-Met inhibitor, said method comprising determining the expression level of c-CBL in a cancer sample from the subject, wherein equal or higher levels of c-CBL expression in the cancer sample relative to a normal sample are indicative that the cancer is not susceptible to treatment with the c-Met inhibitor.

Also disclosed are methods of determining responsiveness of a cancer in a subject to treatment with a c-Met inhibitor, said method comprising determining the expression level of c-CBL in a cancer sample from the subject, wherein lower levels of c-CBL expression in the cancer sample relative to a normal sample are indicative that the cancer is susceptible to treatment with the c-Met inhibitor.

In the methods described herein, the expression level of c-CBL can be determined by determining the amount of c-CBL RNA or c-CBL protein in the sample. Methods for determining the amount of RNA or protein present in a sample are well known in the art. Any known methods for such determinations can be used in the methods described herein. For example, protein levels can be determined by methods including, but not limited to, western blotting or immunohistochemistry. Also, RNA levels can be determined by methods including, but not limited to, RT-PCR, quantitive RT-PCR, expression array analysis, RNase protection assay or northern blotting.

In the methods described herein the expression level of c-CBL can also be determined by determining the presence of loss of heterozygocity (LOH) at the c-CBL gene locus, wherein LOH at the c-CBL locus is indicative of lower c-CBL expression.

The transgenic animals described above can also be used in any of the methods described herein. For example, the transgenic animals described herein can be used to identify a cancer that is or is not susceptible to treatment with a c-met inhibitor wherein the transgenic animal comprises a mutation in a nucleic acid sequence encoding human c-CBL, wherein the mutation results in an amino acid change at position S80N, H94Y, Q249E, V391I, 72515_72517delATG, W802*, R830K, A848T, L620F, P170L, S171S, L281F, L254S, or P782L.

The transgenic animals described herein can also be used to identify a cancer that is susceptible or not susceptible to treatment with a c-met inhibitor, wherein the transgenic animal comprises a mutation in a nucleic acid sequence encoding human c-met, wherein the sequence is mutated in a nucleic acid sequence encoding human c-CBL, wherein the mutation is located in the TKB domain, RING finger domain, proline-rich region, or the C-terminal region of c-CBL.

The transgenic animals described herein can also be used to determine the responsiveness of a cancer in a subject to treatment with a c-met inhibitor, wherein the transgenic animal comprises a mutation in a nucleic acid sequence encoding human c-CBL, wherein the mutation results in an amino acid change at position S80N, H94Y, Q249E, V391I, 72515_72517delATG, W802*, R830K, A848T, L620F, P170L, S171S, L281F, L254S, or P782L, wherein presence of the mutated nucleic acid sequence is indicative that the cancer is responsive to treatment with the c-met inhibitor.

The invention will be further described with reference to the following examples; however, it is to be understood that the invention is not limited to such examples. Rather, in view of the present disclosure that describes the current best mode for practicing the invention, many modifications and variations would present themselves to those of skill in the art without departing from the scope and spirit of this invention. All changes, modifications, and variations coming within the meaning and range of equivalency of the claims are to be considered within their scope.

EXAMPLES

Example 1

Tissue Samples

Paired tumor and normal lung tissues were obtained from 30 NSCLC patients who were recruited at the Taipei Veterans General Hospital after obtaining appropriate institutional review board permission and informed consent from the patients. Among them, 28 were men and 2 were women, with aged at diagnosis ranging from 47 to 90 years. For tumor types, 14 were adenocarcinoma, 10 were squamous cell carcinoma, 5 were large cell carcinoma, and 1 was adenosquamous carcinoma. For tumor stage, 13 were stage I, 4 were stage II, 9 were stage III, and 4 were stage IV.

Cell Culture

Human non-small cell lung carcinoma cell A549 was maintained in DMEM. Media was supplemented with 10% fetal bovine serum, 100 units/ml of penicillin, and 100 g/ml of streptomycin (Invitrogen, Eugene, Oreg.). The cell was maintained at 37° C. in a humidified incubator containing 5% CO2 in air.

A549 and H226 cells are generally accepted predictive cell models for carcinoma behavior, for example, NSCLC and head and neck carcinoma. (Pasqualetti et al., Lung Cancer, 2011; Shi et al., Oncogene, 2011)

Analysis of c-CBL Gene Mutation

Exons 2 to 16 of c-CBL gene were individually amplified by polymerase chain reaction (PCR). Primers are listed in Table 3. PCR conditions were one cycle of 95° C. 5 minutes, 35 cycles of 94° C. 30 seconds, 58° C. 30 seconds, 72° C. 2 minutes, and one cycle of 72° C. 10 minutes. PCR products were treated with ExoSAP-IT (USB Corp., Cleveland, Ohio, USA) and sequenced by Big Dye Terminator Chemistry (Applied Biosystems, Weiterstadt, Germany). Sequencing was performed on the forward coding strand with confirmation of c-CBL alterations performed by sequencing the reverse strand as well. Chromatograms were analyzed for mutations using Mutation Surveyor v2.61 (Softgenetics).

Plasmid Constructs and Site-directed Mutagenesis

The wild-type c-CBL cDNA insert was subcloned into the expression vector pCDNA3.1_N-mCherry, using BamHI and XhoI restriction enzyme sites. Using the parental plasmid pcDNA3.1-NmCherry containing the subcloned full-length wild-type c-CBL cDNA insert, TKB domain point mutation (Q249E) of c-CBL was created using the (SEQ ID NO:31) 5'-CTTTACCCGACTCTTTGAGCCCTGGTCCTCTTTGC-3' primer and its complementary primer with QuickChange Site-Directed Mutagenesis XL kit (Stratagene, La Jolla, Calif.) according to the manufacturer's instructions. The point mutation constructs were confirmed by standard DNA sequencing of both strands.

TABLE 3

| Exon | SEQ ID NO | Forward (5' to 3') | SEQ ID NO | Reverse (5' to 3') |
|---|---|---|---|---|
| 2 | SEQ ID NO: 3 | TAAAATGGTTGCCTGTGGGCAATG | SEQ ID NO: 15 | TGTGTTACCCATTCAGGCACTC |
| 3 | SEQ ID NO: 4 | CATCTTGTATGGTGAATTTGGTGC | SEQ ID NO: 16 | GACTCCGTCTCAAAAAGAAACCAC |
| 4 | SEQ ID NO: 5 | GCTTAATGTGGCTCTCCTTCC | SEQ ID NO: 17 | GTGAGGAGAAGAAAGCAGTTGG |
| 5 | SEQ ID NO: 6 | CTCTGAGTTGGTTGTACATCTGAC | SEQ ID NO: 18 | CAGAACCTTGGCTATTGCGAAAC |
| 6 | SEQ ID NO: 7 | GTCTGTATCTTGCCTTGCCTTC | SEQ ID NO: 19 | CCTAAGTTCCCAGACTCTAACAGATG |
| 7 & 8 | SEQ ID NO: 8 | GGACCCAGACTAGATGCTTTCTG | SEQ ID NO: 20 | CCTTGTATCAGTAAAGGCTATATAATACC |
| 9 | SEQ ID NO: 9 | CGGTATTATATAGCCTTTACTGATACAAGG | SEQ ID NO: 21 | CCAGTCTCCTAAACTGCCATCTTAC |
| 10 & 11 | SEQ ID NO: 10 | CCTAGGTCTGGCCCATTTGTAG | SEQ ID NO: 22 | CTGGCCCACACATATTTCTTAACAG |
| 12 | SEQ ID NO: 11 | CAGAGGCTCAGCTGTGGTAAG | SEQ ID NO: 23 | CAGAGCAATGAAACAGATGGCAG |
| 13 & 14 | SEQ ID NO: 12 | GCTCTGTTCAATTTGAGTTATGTCTG | SEQ ID NO: 24 | GCTTAGATCAAGCTATCTCAATTGCC |
| 15 | SEQ ID NO: 13 | GTTGGCCCACAGTAGACAATC | SEQ ID NO: 25 | CTTGGGACTTTCCTCCCATTTAGAC |
| 16 | SEQ ID NO: 14 | CTTGTGACTGAAGAGCACATGTAC | SEQ ID NO: 26 | CTAGGTGCCACTTGAGTAATAACTC |

Table 3 provides a listing of c-CBL amplification primers used in an experimental example described herein.

Transfection of c-CBL Constructs

A549 cell line was transfected using the ExGen500 (Fermentas, Glen Burnie, Md.) reagents according to the manufacturer's instructions. Two g of expression plasmid DNA, containing either no insert (empty vector), wild-type c-CBL, or Q249E c-CBL, was used for transfection for each 6 well culture plate.

Cell Viability Assay

Cells were transfected with pcDNA 3.1_N-mCherry empty vector, c-CBL wild type, and c-CBL mutant Q249E constructs. After 48 h transfection, cells stained with Trypan Blue solution (0.4%) (Sigma-Aldrich, St. Louis, Mo.) was used to measure the effect of c-CBL mutation on cell growth.

A Group of Taiwanese Lung Cancer Patients Carried Mutations in c-CBL Gene.

Recent reports have indicated several c-CBL mutations in AML. (Reindl C, et al. Clin Cancer Res 15:2238-2247 (2009); Caligiuri M A, et al., Blood 110:1022-1024 (2007)). A genomic DNA sequence screening of paired tumor and normal samples from 30 Taiwanese lung cancer patients was performed to investigate the role of c-CBL in lung cancer. Twelve (12) pairs of primers were prepared to sequence the coding region of c-CBL gene from exons 2 to 16 (Table 3). Two exonic mutations in c-CBL were identified. One is a known single nucleotide polymorphism (SNP) L620F in exon 11 of patients TW9 and TW18. Importantly, another is a non-synonymous mutation Q249E, which was confirmed by sequencing both strands of c-CBL gene in DNA from tumor tissue of patient TW30 (Tables 4, 5 and FIG. 1A). Moreover, there was no Q249E mutation shown in corresponding normal tissue, suggesting that Q249E is a somatic mutation. The novel somatic mutation Q249E is located in TKB domain and SNP L620F is in proline-rich region (FIG. 1B). In addition, seven mutations were found in intron including a known SNP 67960 het_delT in intron 4 and other novel SNPs (Table 4), which were also confirmed by sequencing both strands of c-CBL gene in DNA from tumor and corresponding normal tissue. The total mutation rate for tumor was 30% (9/30) and for normal was 27% (8/30). The different tumor types showed different mutation rates in the Taiwanese lung cancer population. There were 77.8% (7/9) in adenocarcinoma (AD), 100% (9/9) in squamous cell carcinoma (SQ), 33.3% (3/9) in adenosquamous carcinoma (AD/SQ), and 66.7% (6/9) in large cell carcinoma (LC) (FIG. 2). However, due to the small number analysis, The mutation rates between AD and SQ (P=0.133), between AD and AD/SQ (P=0.058), and between AD and LC (P=0.599) were not statistically significant.

TABLE 4

| Location | Mutation | Domain | Numbers of sample (Frequency) |
|---|---|---|---|
| exon 4 | 67885 C > CG (Q249E) | TKB | 1 (3.3%) |
| Intron 4 | 67960 het_delT* | | 30 (100%) |
| | 67968 del C | | 2 (13.3%) |
| Intron 5 | 68861_68862 het_insT | | 19 (63.3%) |
| | 68861_68862 insT | | 3 (10%) |
| Intron 8 | 72287 del T | | 29 (96.7%) |
| | 72315 G > GT | | 13 (43.3%) |
| Intron 9 | 78771 G > T | | 20 (66.7%) |
| exon 11 | 79346 C > CT (L620F)** | Pro_rich | 2 (13.3%) |

Known SNP: rs 3842642;
**Known SNP: rs2227988;
TKB: tyrosine kinase binding domain; Pro_rich: proline-rich region.

Table 4 summarizes the analysis of c-CBL mutations that occurred in tumor tissues of 30 Taiwanese lung cancer patients during the experiment described in Table 3.

Since c-CBL protein interacts with c-Met or EGFR, mutations in c-Met and EGFR of this cohort of 30 Taiwanese lung cancer patients were analyzed. The mutations in c-Met and EGFR were analyzed in both tumor and corresponding normal tissues and were previously identified. (Jagadeeswaran R, et al., Cancer Res 68:132-142 (2008)). The data indicated that patients with c-CBL Q249E somatic mutant showed no c-Met and EGFR mutations, but two patients with c-CBL L620F SNP had either N375S SNP in c-Met gene or L858R mutation in EGFR gene (Table 5).

TABLE 5

| No. | Sex | Tumor type | Stage | c-Cbl | c-Met | EGFR |
|---|---|---|---|---|---|---|
| TW 1 | M | AD | IIIA | NF | NF | Del:747-751 |
| TW 2 | M | AD | IIA | NF | NF | L858R |
| TW 3 | F | AD | IB | NF | NF | Del:746-750 Ins A |
| TW 4 | M | AD | IIIA | NF | NF | Del:748-752 |
| TW 5 | M | AD | IB | NF | NF | Del:747-753 Ins S |
| TW 6 | M | AD | IIIA | NF | N375S | Del: 746-750 |
| TW 7 | F | AD/SQ | IIB | NF | NF | Del:746-750 |
| TW 8 | M | AD | IV | NF | NF | Del:746-750 |
| TW 9 | M | AD | IB | L620F | NF | L858R |
| TW10 | M | AD | IV | NF | NF | L858R |
| TW11 | M | AD | IV | NF | NF | Del:746-750 |
| TW12 | M | AD | IB | NF | N375S | NF |
| TW13 | M | SQ | IB | NF | NF | Del:746-750 |
| TW14 | M | AD | IB | NF | L211W | NF |
| TW15 | M | SQ | IIB | NF | N375S | NF |
| TW16 | M | LC | IIIA | NF | NF | NF |
| TW17 | M | SQ | IIIA | NF | N375S* | NF |
| TW18 | M | SQ | IIIA | L620F | N375S | NF |
| TW19 | M | LC | IB | NF | NF | NF |
| TW20 | M | SQ | IIIA | NF | NF | L858R |
| TW21 | M | LC | IB | NF | N375S | NF |
| TW22 | M | AD | IB | NF | N375S | NF |
| TW23 | M | LC | IB | NF | NF | NF |
| TW24 | M | SQ | IV | NF | NF | NF |
| TW25 | M | SQ | IIIB | NF | N375S | NF |
| TW26 | M | SQ | IB | NF | N375S | NF |
| TW27 | M | AD | IIIA | NF | N375S | NF |
| TW28 | M | SQ | IB | NF | N375S | NF |
| TW29 | M | LC | IIB | NF | NF | NF |
| TW30 | M | SQ | IB | Q249E | NF | NF |

AD: adenocarcinoma;
SQ: squamous cell carcinoma;
LC: large cell carcinoma;
NF: not found;
*homozygous mutation.

Table 5 summarizes c-CBL, c-Met, and EGFR exon mutations that were found in Taiwanese lung cancer patients during the experiment described in Tables 3 and 4.

c-CBL Mutations Increase the Lung Cancer Cell Viability.

Figure 3:
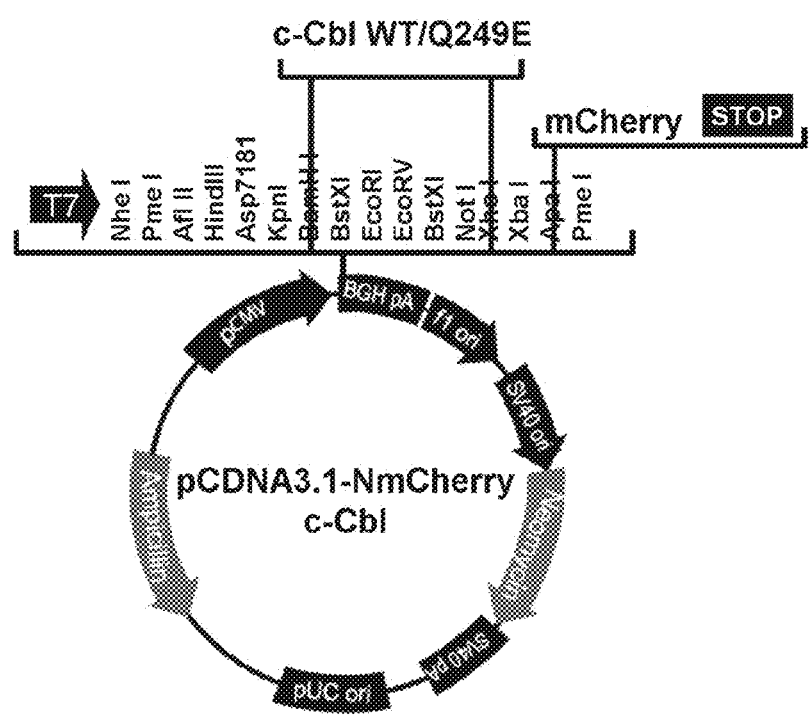
FIG. 3 shows c-CBL wild-type and mutant constructs that were made into a pcDNA3.1-NmCherry vector during the experimental example of FIGS. 1 and 2. The pcDNA3.1-NmCherry vector had ampicillin and neomycin for antibiotic selection. The multiple cloning site for pcDNA3.1(+) contained mCherry inserted into the ApaI site, and a cDNA sequence of c-CBL wild-type and Q249E mutant was inserted between BamHI and XhoI. The vector map was modified from http://www.invitrogen.com.
Figure 4:
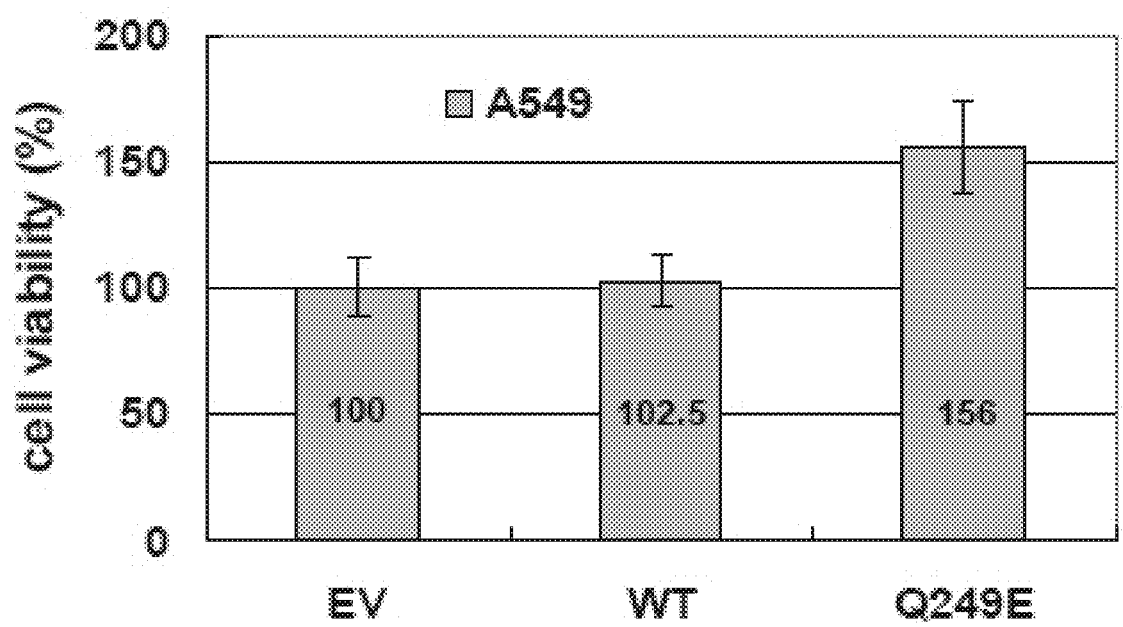
FIG. 4 shows the A549 cell viability of c-CBL wild-type and Q249E mutant constructs that were studied during the experimental example of FIGS. 1-3. Compared to the control empty vector (EV) transfectant, c-CBL wild-type (WT) and mutant Q249E transfectants showed 102.5% ($P=0.868$) and 156% ($P=0.049$) cell viability in A549 cells after 48 h transfection.

To investigate the effect of c-CBL mutation in cell biological functions, the c-CBL wild-type and Q249E mutant expression constructs were made into pcDNA3.1-NmCherry vector (FIG. 3), which carried cherry red fluorescent in C-terminal and was used to confirm the transfection efficiency. Secondly, A549 cell showing low c-CBL basal expression was used so that the effect of exogenous c-CBL on cell viability was observed unambiguously without the complication of endogenous c-CBL. Control empty vector, c-CBL wild-type, or c-CBL Q249E mutant was transfected to A549 cell line and the cell viability was evaluated at 48 h post-transfection. A549 transfected cells showed 102.5% (P=0.868) viability in c-CBL wild-type and 135% (P=0.049) viability in Q249E mutant compared to the empty control vector (FIG. 4).

The results demonstrated that c-CBL mutation occurs in lung cancer patients. In addition, the novel c-CBL somatic mutation, Q249E, showed an increasing viability compared to wild-type c-CBL in A549 cell model. A recent study showed that there is no somatic mutation and amplification in c-Met but protein overexpression in Taiwanese lung cancer. (Engelman J A, et al., Science 316:1039-1043 (2007)). In addition, mutations in EGFR are observed frequently in NSCLC patients in East Asian populations.

Polyubiquitination of RTKs requires a functional c-CBL TKB domain, which interacts with receptor targets. A novel c-CBL somatic mutation Q249E in TKB domain was discovered. It is contemplated that the novel c-CBL somatic mutation Q249E in TKB domain can lose the ability to interact and degrade its target RTKs. The cell viability results indicated that Q249E mutant increased cell proliferation, showing the importance of TKB domain. Hence, it is contemplated that the loss of negative control through c-CBL mutations that delete c-CBL binding site function can contribute to the deregulation of c-Met or other RTKs observed in cancers. The patient with c-CBL Q249E mutation did not show mutation in either c-Met or EGRF gene. Thus, it is contemplated that c-CBL mutation can lead to overexpression of c-Met and EGFR proteins without mutation in corresponding genes.

Example 2

Tissue Samples

Lung cancer tissue and paired adjacent normal lung tissues were obtained from 50 Caucasian, 29 African-Americans and 40 Taiwanese NSCLC patients who were recruited at the University of Chicago Hospital (Chicago, USA) (Caucasian and African-American patients) and Taipei Veterans General Hospital of Taiwan (Taiwanese patients). Out of 119 samples, 77 were men, 38 were women and 4 were unknown with age at diagnosis ranging from 47 to 90 years. In terms of tumor types, 53 were adenocarcinoma, 32 were squamous cell carcinoma and 34 were large cell carcinoma. 49 were stage I, 14 were stage II, 34 were stage III, and 13 were stage IV.

Cell Culture

Human non-small cell lung carcinoma cells A549 and H358 were maintained in DMEM and RPMI-1640, respectively. Human embryonic kidney 293T cells were cultured in DMEM. Media were supplemented with 10% fetal bovine serum, 100 units/ml of penicillin, and 100 mg/ml of streptomycin (Invitrogen, Carlsbad, Calif.). Cells were cultured at 37° C. in a humidified incubator containing 5% CO2.

c-CBL Gene Mutational Analysis

Exons 2 to 16 of c-CBL gene were individually amplified by polymerase chain reaction (PCR). PCR conditions were 1 cycle of 95 uC for 5 minutes; 35 cycles of 94° C. for 30 seconds, 58° C. for 30 seconds and 72° C. for 2 minutes; and one cycle of 72° C. for 10 minutes. PCR products were treated with ExoSAP-IT (USB Corporation, Cleveland, Ohio) and sequenced by Big-Dye Terminator Chemistry (Applied Biosystems, Foster City, Calif.). Sequencing was performed on the forward coding strand with confirmation of c-CBL alterations performed by sequencing the reverse strand as well. Chromatograms were analyzed for mutations using Mutation Surveyor v2.61 (Softgenetics, State College, Pa.).

Plasmid Constructs and Site-Directed Mutagenesis

The wild-type c-CBL cDNA insert was subcloned into the pAlterMax expression vector using XhoI and SalI restriction enzyme sites (Promega, Madison, Wis.). Using this parental plasmid pAlterMax-c-CBL, the TKB domain double mutation (S80N/H94Y), the point mutation (Q249E), and the C-terminal point mutation W802* of c-CBL were created using the following primers: SEQ ID NO:27 5'-GCTGGCGCTAAAGAATAACCCACCTTATATCTTA-GAC-3' and SEQ ID NO:28 5'-CTACCAGATACC-TACCAGTATCTCCGTACTATCTTGTC-3' for the double mutation S80N/H94Y; SEQ ID NO:29 5'-CTT-TACCCGACTCTTTGAGCCCTGGTCCTCTTTGC-3' for Q249E, and SEQ ID NO:30 5'-AGCTCCTCCTTTGGCT-GATTGTCTCTGGATGGTGATC-3' for W802* along with their complementary primers using the QuickChange Site-Directed Mutagenesis XL kit (Stratagene, La Jolla, Calif.) according to the manufacturer's instructions. The constructs were confirmed for the point mutations by standard DNA sequencing of both strands.

Loss of Heterozygosity (LOH) Analysis

Five microsatellites on chromosome 11 (3 on 11q at or within 200 kb up or downstream of the c-CBL gene and 2 control markers on 11p) were selected for analysis. Established microsatellite markers and respective primer sequences were selected from the GeneLoc database (http://genecards.weizmann.ac.il/geneloc/index.shtml, Weizmann Institute of Science, Rehovot, Israel). Primers were custom designed and each forward primer was fluorescently labeled at the 59 end with FAM, PET, NED, or VIC (Applied Biosystems). Primer annealing temperatures and duplex scores were evaluated with NIST Primer Tools (http://yellow.nist.gov:8444/dnaAnalysis/primerToolsPage.do; National Institute of Standards and Technology, Gaithersburg, Md.). Primers were verified by performing PCR with control DNA (isolated from TK6 cells) and resolving the products on agarose gels. Bands were visualized with an UV transilluminator. Genomic DNA was extracted from tumor samples and paired normal lung tissue. Primers were grouped into multiplex combinations. Marker D11S929 served as an internal control to check for consistency in PCRs and of peaks from capillary electrophoresis. Multiplex PCRs were carried out in a volume of 10 mL that contained 1 mL genomic DNA (20-50 ng), 0.5 mM of each primer (1.0 mM total for each primer pair), 400 mM dNTPs, 1×PCR buffer containing MgCl2, and 0.2 U Taq DNA polymerase. PCR was performed on the ABI GeneAmp 9700 PCR System under the following conditions: 5 min at 94° C.; 30 cycles of 30 sec at 94° C., 1 min at 60° C., 1 min at 72° C.; and 5 min at 72° C. The PCR products were separated by capillary electrophoresis on an ABI 3130XL DNA Analyzer. Chromatograms were analyzed with Peak Scanner 1.0 and GeneMapper 3.7 software (Applied Biosystems) for allelic alterations. The area of the peaks produced by the DNA PCR products was quantified for each allele. The ratio of the allelic areas was calculated for each tumor and paired normal DNA sample. When the qLOH (allelic ratio for the tumor peaks divided by the allelic ratio of paired normal sample) was ≤0.5 or ≥2.0 for c-CBL and at least one other 11q marker in at least two separate experiments, the sample was considered as having an allelic imbalance and interpreted as LOH. Samples were evaluated in at least two separate experiments and samples showing prospective LOH at c-CBL repeated a third time which included a new control marker at the BAX locus on chromosome 19 to verify integrity of sample DNA.

Transfections of c-CBL Constructs

The A549 cell line was transfected using the Fugene HD (Roche, Nutley, N.J.) reagent according to the manufacturer's instructions. Eight mg of plasmid DNA, containing either no insert (empty vector), wild-type c-CBL, S80N/H94Y c-CBL, Q249E c-CBL or W802* CBL was used for transfection in a 6-well culture plate. Cells were harvested 48 h after transfection and analyzed for expression.

c-CBL Knockdown c-CBL knockdown was performed using lentiviral transduction using MISSION lentiviral transduction particles (Sigma-Aldrich, St. Louis, Mo.) as per manufacturer's instructions. Briefly, 16105 H358 cells/well were seeded in 6-well plates and infected the following day with c-CBL lentiviral shRNA constructs. To generate stable c-CBL knockdown cell lines, cells were selected for 2 days with 1 mg/ml puromycin. c-CBL levels were determined using whole cell lysates by immunoblotting with anti-CBL antibody (Santa Cruz Biotechnologies, Santa Cruz, Calif.).

Cell Viability Assay

Cells were transfected as described above in the transfection assay. Forty-eight hours after transfection, viability of cells was assessed using Trypan Blue exclusion.

Wound Healing Assay

A549 cells were seeded in 6-well plates and cultured for 48 h until 100% confluent. The medium was then changed and the cells were transfected as described in the transfection assay. Twelve hours after transfection, a straight scratch was made across the cell layer using a 1 ml pipette tip. The cells were then gently washed with 16 PBS to remove cellular debris and the media was replaced. Photographs were taken of the wound region every 12 h until 48 h.

Western Blot Analysis

Forty eight hours after transfection, cells were collected and washed twice in 1×PBS, then lysed in ice-cold lysis buffer (0.5M Tris-HCl with pH 7.4, 1.5 M NaCl, 2.5% deoxycholic acid, 10 mM EDTA, 10% NP-40, 0.5 mM DTT, 1 mM phenylmethylsulfonyl fluoride, 5 mg/mL leupeptin, and 10 mg/mL aprotinin) for 5 minutes. The lysate was centrifuged at 13,000 rpm for 20 minutes at 4° C., and protein content of the supernatant was measured. Total cell lysates (50 mg/well) were separated by SDSPAGE electrophoresis and the gels transferred onto nitrocellulose membranes (Whatman, Piscataway, N.J.). Membranes were blocked with 5% non-fat dry milk in phosphate-buffered saline containing Tween-20 (PBST) (1×PBS, 0.1% Tween-20) for 1 h at room temperature and incubated with the appropriate primary antibody at 4° C. overnight. Membranes then were washed three times with PBST and probed with appropriate horseradish peroxidase (HRP)-conjugated secondary antibody for 1 h at room temperature. The membranes were again washed three times in PBST and bands were visualized using Western blot chemiluminescence reagent (BioRad, Valencia, Calif.) on a Chemidoc Gel documentation system (BioRad, Valencia, Calif.). Antibodies were obtained from Santa Cruz Biotechnologies and used at the following dilutions: c-CBL, 1:5000; c-MET, 1:5000; EGFR, 1:5000; ubiquitin, 1:1000; HA, 1:5000 and b-actin, 1:10,000.

Flow Cytometry

Cell cycle analysis was carried out by flow cytometry. Approximately 26106 cells were grown in media containing 10% FBS. Cells were harvested by trypsin/EDTA treatment, washed with 1×PBS three times and fixed with ice-cold 70% ethanol for 2 h. Cells were washed again with cold PBS and stained with a solution containing 25 mg/mL propidium iodide, 200 mg/mL RNase A, and 0.1% Triton X-100 for 30 minutes in the dark. Cell cycle analysis was performed using a Guava PCA-96 flow cytometer (Guava Technologies, Millipore, Billerica, Mass.).

Ubiquitin Ligase Activity 293T cells were maintained in culture in DMEM supplemented with 10% FBS and 1% penicillin (100 units/mL) and streptomycin (100 mg/mL) were transfected with 0.2 mg EGFR-pcDNA3 and 2 mg HA-tagged c-CBL constructs as indicated using calcium phosphate according to manufacturer's protocol (Profection, Promega, Madison, Wis.). Twenty-four hours post-transfection, cells were starved overnight in DMEM supplemented with 0.5% FBS, and then treated with or without EGF (100 ng/ml) for 15 min. The cells were collected and washed two times in ice-cold PBS containing 0.2 mM sodium orthovanadate then lysed in icecold lysis buffer (10 mM Tris HCl, pH 7.5, 150 mM NaCl, 5 mM EDTA, 1% Triton X100, 10% Glycerol, 2 mM sodium orthovanadate and protease inhibitors). Lysates were cleared of debris by centrifugation at 16,000 g for 10 min at 4° C. EGFR immunoprecipitations were performed on 200 mg of cleared lysate using 250 ng of rabbit-anti-EGFR and Protein A/G Plus Sepharose overnight at 4 uC. Precipitations were washed 5 times in lysis buffer before boiling in Laemmli buffer. Elutions were immunoblotted with anti-ubiquitin and EGFR. Twenty micrograms of cleared lysate were immunoblotted for each of the c-CBL constructs using anti-HA.

Statistical Analysis

Mutation rates between different groups were compared using Fisher's exact test. For continuous variables, group comparisons were performed using analysis of variance (ANOVA) followed by Sidak's adjustment for multiple comparisons. Experiments involving repeated measurements over time were analyzed using repeated measures ANOVA with the Greenhouse-Geisser adjustment to the degrees of freedom. Analyses were conducted using STATA (v10.1) software (Stata Corporation, College Station, Tex.).

c-CBL Gene Mutations in Lung Cancer

To investigate the role of c-CBL in lung cancer, its genomic DNA in tumor and paired normal samples drawn from multiple ethnicities was analyzed. The lung tumor samples represented Caucasians (n=50), African-Americans (n=29), and Taiwanese (n=40) lung cancer patients. Twelve pairs of primers were designed to sequence the coding region of c-CBL gene that spans exons 2 to 16. Eight unique somatic mutations in c-CBL exons were identified among 8 different patients. A variation L620F, a known SNP (rs2227988) in exon 11 was also detected. Importantly, the eight novel nonsynonymous mutations were confirmed by sequencing both strands of c-CBL genomic DNA obtained from lung tumor samples (Table 1). Moreover, none of the 8 mutations were detected in the corresponding normal tissue, indicating that these were somatic mutations. Four synonymous single nucleotide variations (SNVs) were also identified.

TABLE 1 c-CBL mutation analysis in 119 lung cancer patient tumor tissues.

| | | | Numbers of Sample [Frequency] | | |
|---|---|---|---|---|---|
| Location | Mutation | Domain | Caucasian (50)* | African-American (29)* | Taiwanese (40)* |
| Exon 2 | 26354 G > AG (S80N)# | TKB | 1 (2%) | 0 | 0 |
| | 26395 C > CT (H94Y)# | TKB | 1 (2%) | 0 | 0 |
| Exon 4 | 67885 C > CG (Q249E) | TKB | 0 | 0 | 1 (2.5%) |
| Exon 8 | 72104 G > AG (V391I) | RING | 1 (2%) | 1 (3.5%) | 0 |
| Exon 9 | 72515_72517 del ATG | Pro-rich | 1 (2%) | 0 | 0 |
| Exon 11 | 79346 C > CT (L620F)^ | Pro-rich | 0 | 0 | 2 (5%) |
| Exon 15 | 92375 G > AG (W802*) | C-terminal | 0 | 1 (3.5%) | 0 |
| Exon 16 | 93412 G > AG (R830K) | C-terminal | 0 | 1 (3.5%) | 0 |
| | 93465 G > AG (A848T) | C-terminal | 0 | 1 (3.5%) | 0 |

*( ) indicates number of samples.
S80N and H94Y mutations were found in the same patient.
^Known SNP.

Figure 5A:
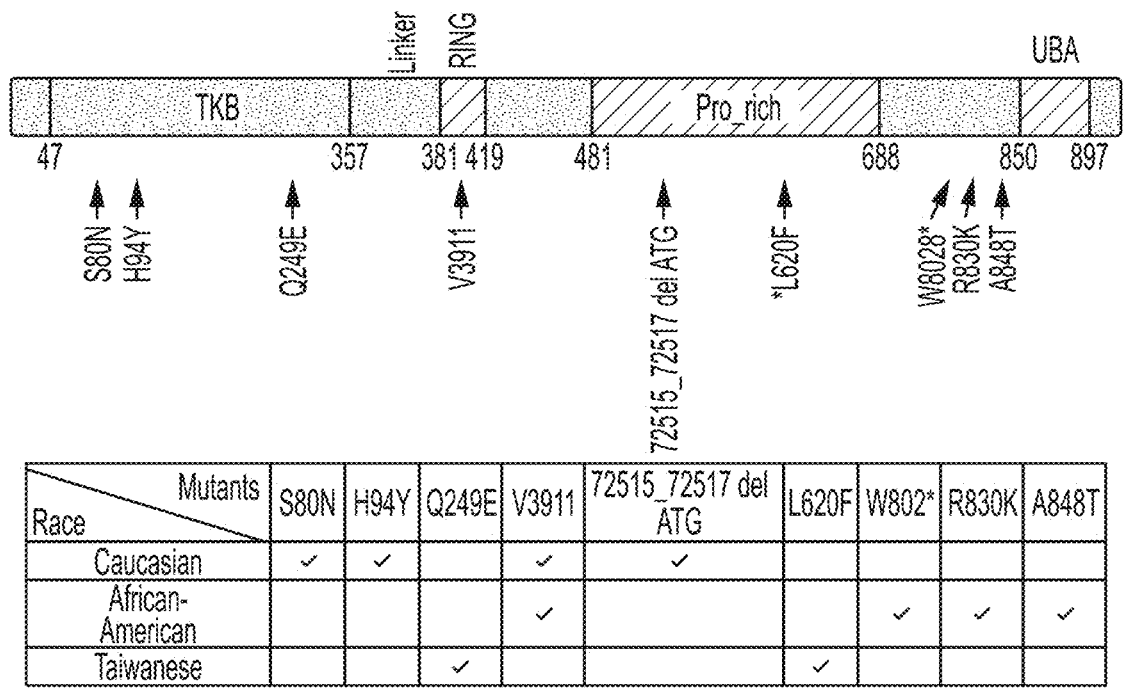
FIGS. 5A, 5B, 5C, and 5D show c-CBL mutants.
Figure 5B:
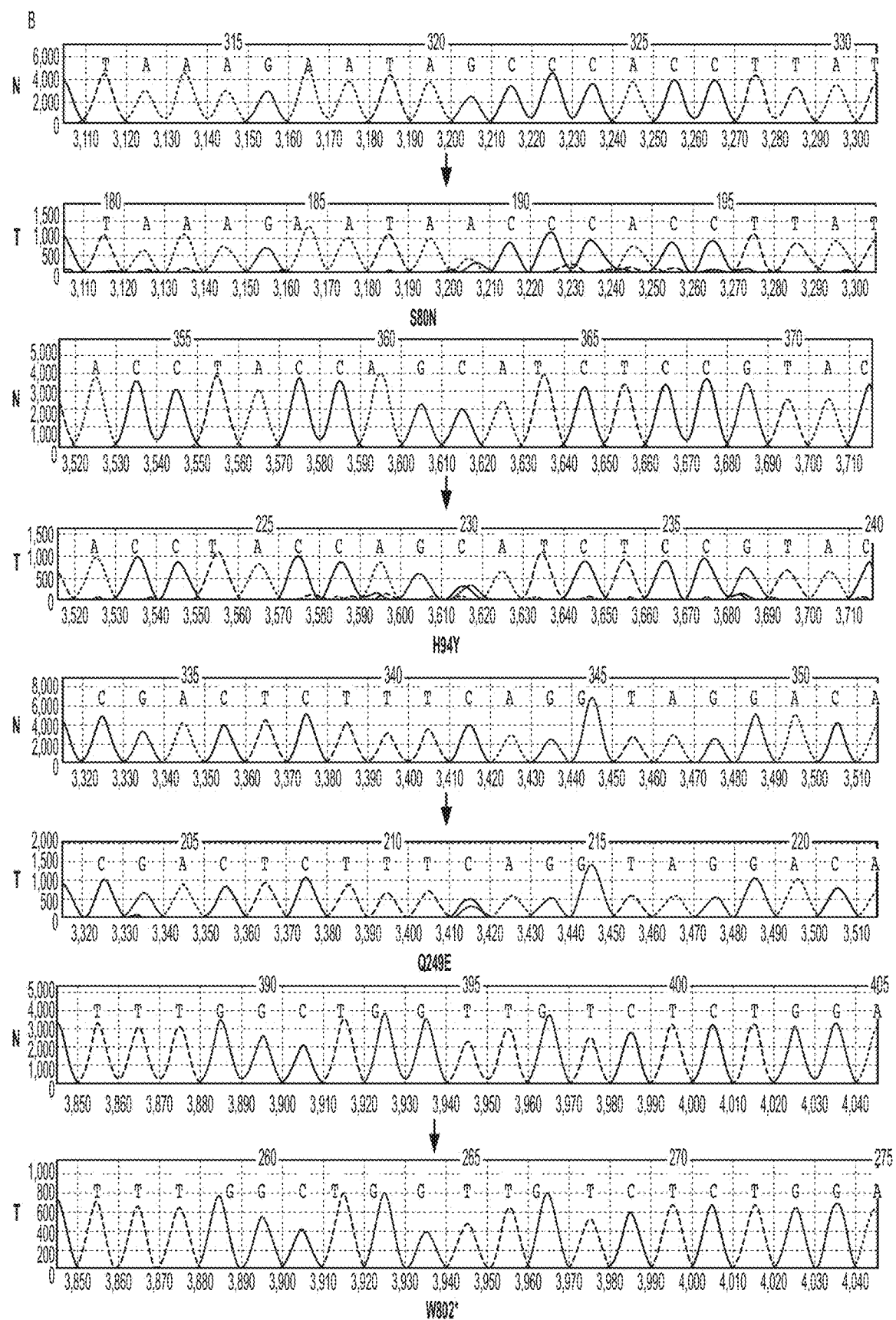

Three of the 8 non-synonymous mutations were located in the TKB (tyrosine kinase binding) domain (S80N, H94Y, and Q249E), one in the RING finger domain (V391I), one in the proline-rich region (72515_72517 del ATG), and three in the Cterminal region (W802*, R830K, and A848T) of the c-CBL protein (FIG. 5A). In FIG. 5B, we show model chromatograms of representative samples.

11q LOH of c-CBL Gene

Figure 5C:
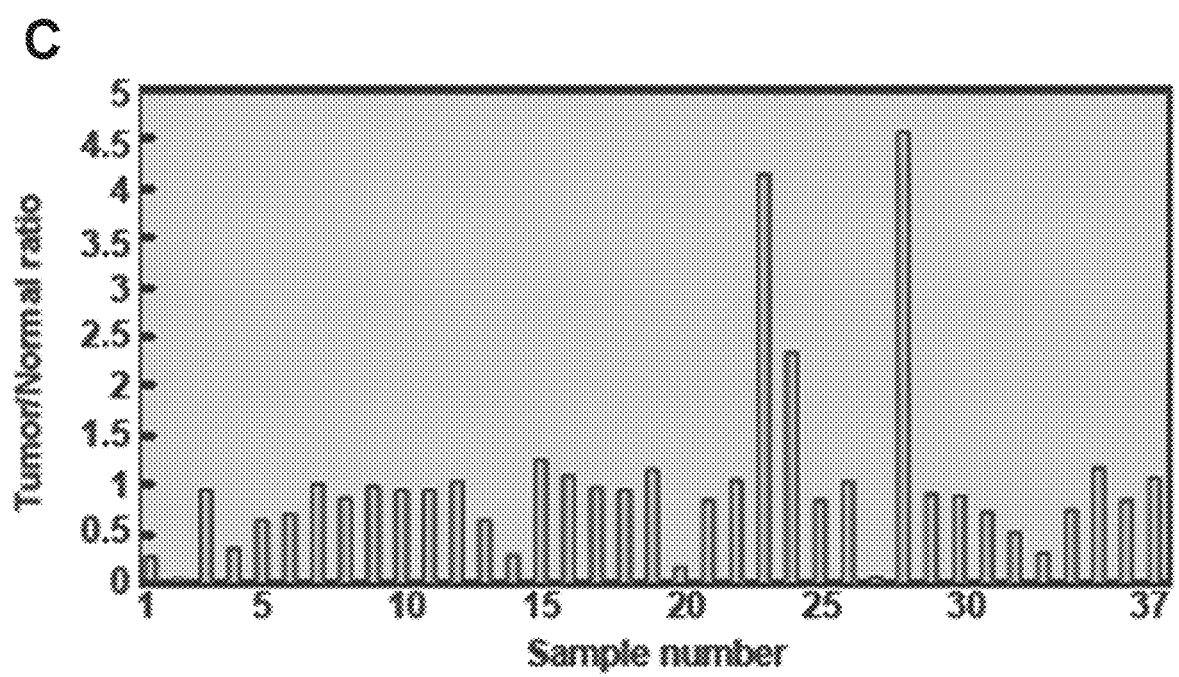

Paired lung tumor and normal lung tissue samples from Taiwanese patients (n=37) were investigated for LOH. Eight (21.6%) showed LOH at the c-CBL locus on chromosome 11 while 29 samples (78.4%) revealed normal allelic contribution at the microsatellite markers (FIGS. 5C and D).

c-CBL Mutations in Different Ethnic Groups

The c-CBL double mutant S80N/H94Y was found in the same patient, and the overall mutation rate for c-CBL in lung tumors was 6.7% (8/119). The frequency of c-CBL mutation was highest in large cell carcinoma (14.7%; 5 of 34 patients), followed by squamous carcinoma (6.3%; 2 of 32 patients), and the least was observed in adenocarcinoma (AD) (1.8%; 1 of 53 patients), although these rates were not statistically significant (p=0.292). Mutation rates were 6.0% among Caucasians (0 of 20 in AD; 0 of 10 in SQ; and 3 of 20 in LC), 13.8% in African-Americans (1 of 10 in AD; 1 of 10 in SQ; and 2 of 9 in LC), and 2.5% (0 of 23 in AD; 1 of 12 in SQ; and 0 of 5 in LC) in the Taiwanese population. Additionally, two Taiwanese patients with lung cancer (one squamous and one adenocarcinoma) had the known SNP L620F.

Mutations in MET and EGFR can be Co-Associated with c-CBL Alterations

Figure 6:
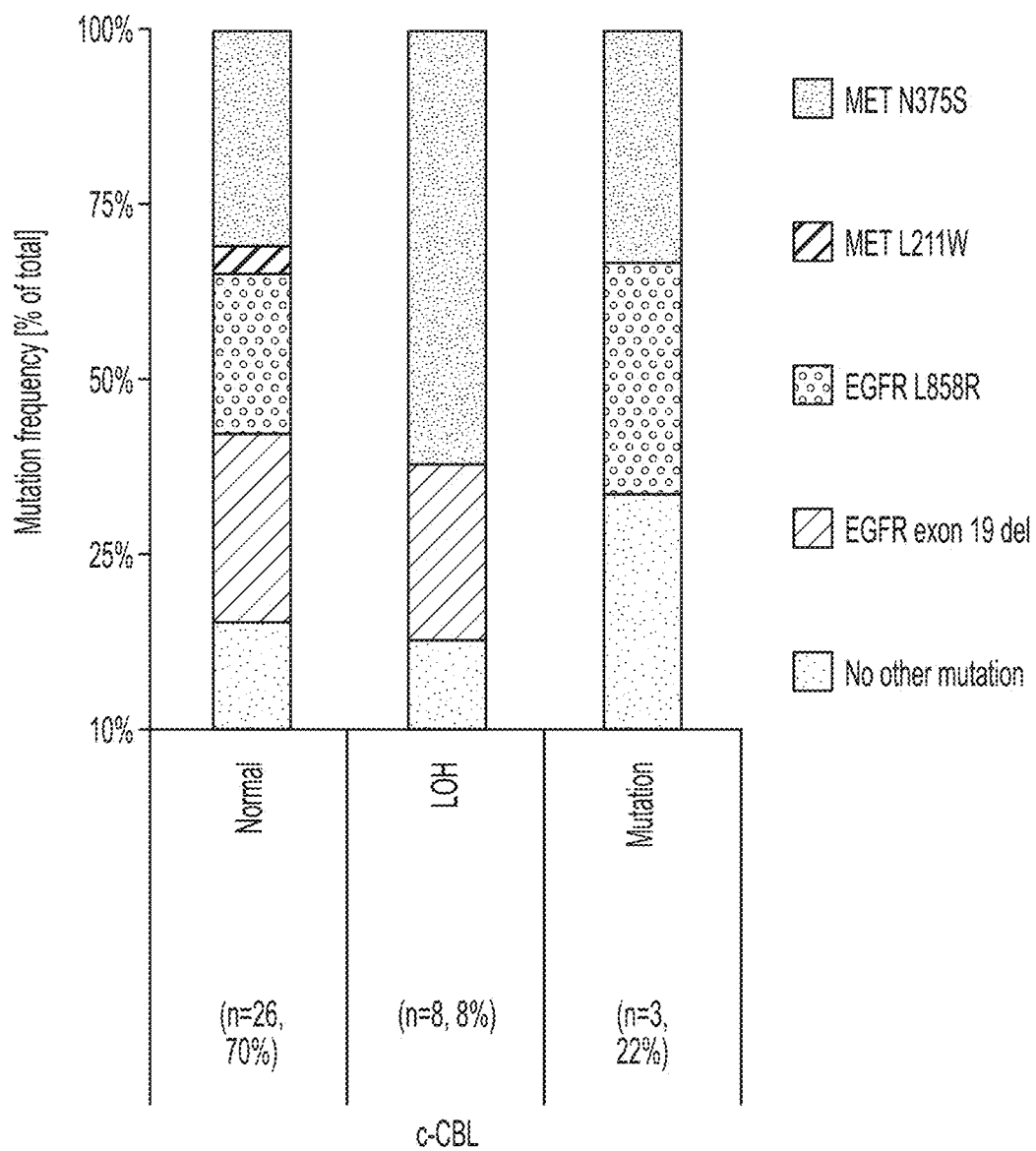
FIG. 6 shows the relationship between c-CBL mutations and MET and EGFR mutations in lung cancer, as analyzed as described in Example 2. 37 Taiwanese samples were analyzed for mutations in c-CBL, MET and EGFR and for LOH analysis in the c-CBL locus. Data shows 21.6% (8/37) had LOH, whereas 8% (3/37) had a c-CBL mutation (including the known SNP L620F), these samples were mutually exclusive. Additionally, 5 of 8 LOH samples also had MET N375S mutation and 2 had an EGFR exon 19 deletion. In the samples having c-CBL mutation, 1 also had a MET N375S mutation while another had an EGFR L858R mutation. In samples that did not harbor any c-CBL mutation (70%, 26/37), 22 had either a MET or an EGFR mutation and only 4 did not have a mutation in any of these 3 genes.

Since East Asians with lung cancer have a higher frequency of EGFR and MET mutations in lung tumors, mutations in EGFR and MET in the same Taiwanese cohort samples were also determined. These results were compared with the observed c-CBL alterations (LOH and/or mutations). In the 37 samples tested, no overlap between c-CBL mutations and c-CBL LOH was found (FIG. 6). Of the three c-CBL mutants (including the known L620F SNP, rs2227988), one of the samples had a MET mutation (N375S), and the other had an EGFR mutation (L858R). Among the 8 samples that had a LOH at the c-CBL locus, 5 had an additional mutation in MET (N375S), and 2 had an EGFR exon 19 deletion. Twenty-six samples had neither c-CBL mutation nor c-CBL LOH (3 patients had a c-CBL mutation but no c-CBL LOH). Among these 26 samples 9 had a MET mutation (8 N375S, 1 L211W), 13 had an EGFR mutation (7 exon 9 deletion, 6 L858R), and 4 had no other MET or EGFR mutation. Thus, the rate of MET or EGFR mutations among patients with LOH at the c-CBL locus (7 of 8) was similar to that seen in patients without c-CBL mutation or LOH (22 of 26 patients) (p=0.99). These 4 patients with no identifiable mutation in c-CBL, MET or EGFR represented 10.8% of the 37 patients analyzed in the Taiwanese patient cohort. Conversely, 89.2% Taiwanese lung cancer patients have an identifiable mutation in either c-CBL, MET or EGFR or a combination of the three genes (FIG. 6). Additionally, p53 and KRAS mutations were determined in these Taiwanese cohorts. Two p53 and 1 KRAS mutation were detected. The single KRAS mutation overlapped with one p53 mutation. This patient also had the EGFR exon 19 deletion but had no c-CBL mutation. The other p53 mutation sample had a c-CBL LOH with concurrent MET N375S mutation. Thus, in the Taiwanese samples analyzed, p53/KRAS mutations and c-CBL mutations were mutually exclusive.

Cellular Functions of c-CBL Alterations in the Context of Lung Tumorigenesis

E3 activity is intact in the mutant c-CBL proteins. To investigate whether the different c-CBL mutations affect the E3 activity, EGFR was chosen as a model substrate for c-CBL E3 function. All of the c-CBL mutants tested enhanced ubiquitination of the activated EGFR similar to the wild-type c-CBL protein. The catalytic activity of the c-CBL mutants was not impaired when EGFR was the substrate.

Effect on Lung Cancer Cell Viability.

Figure 7A:
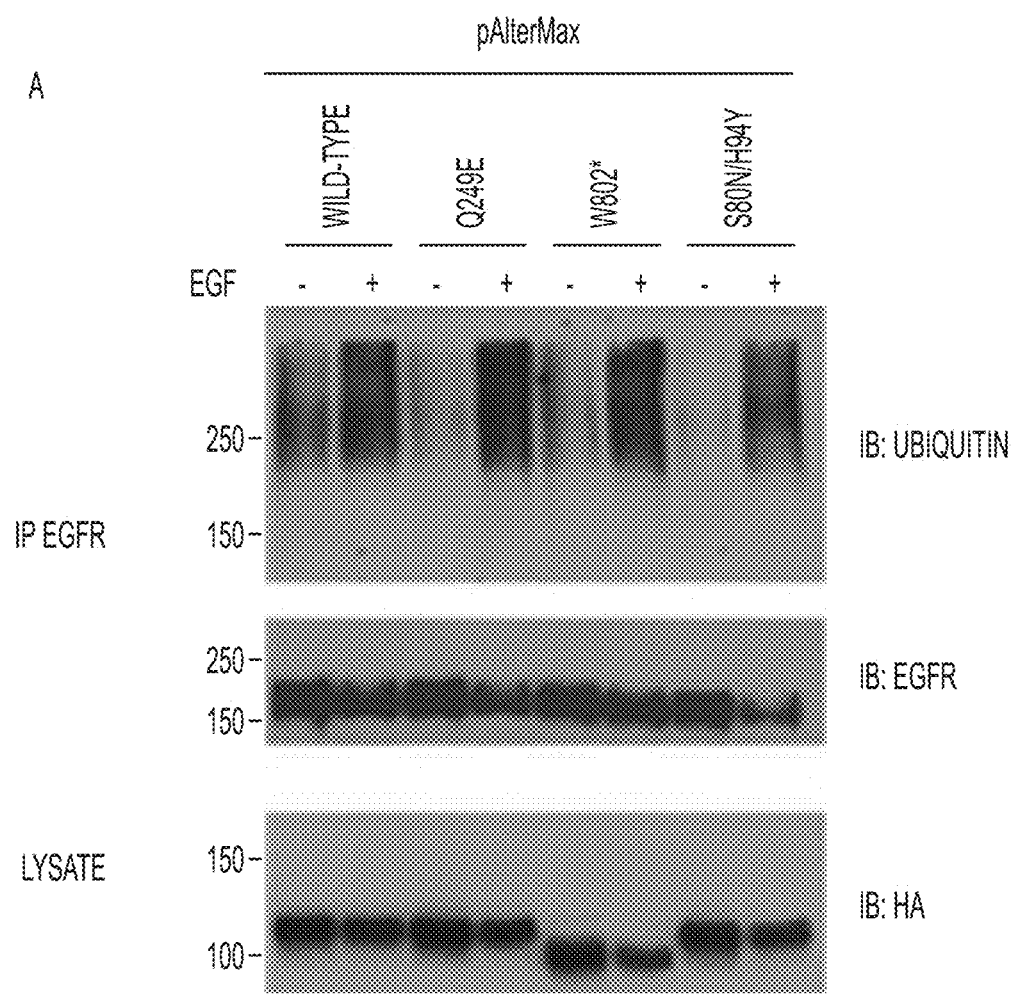
FIGS. 7A, 7B, 7C, and 7D show cellular data on four c-CBL mutants.
Figure 7B:
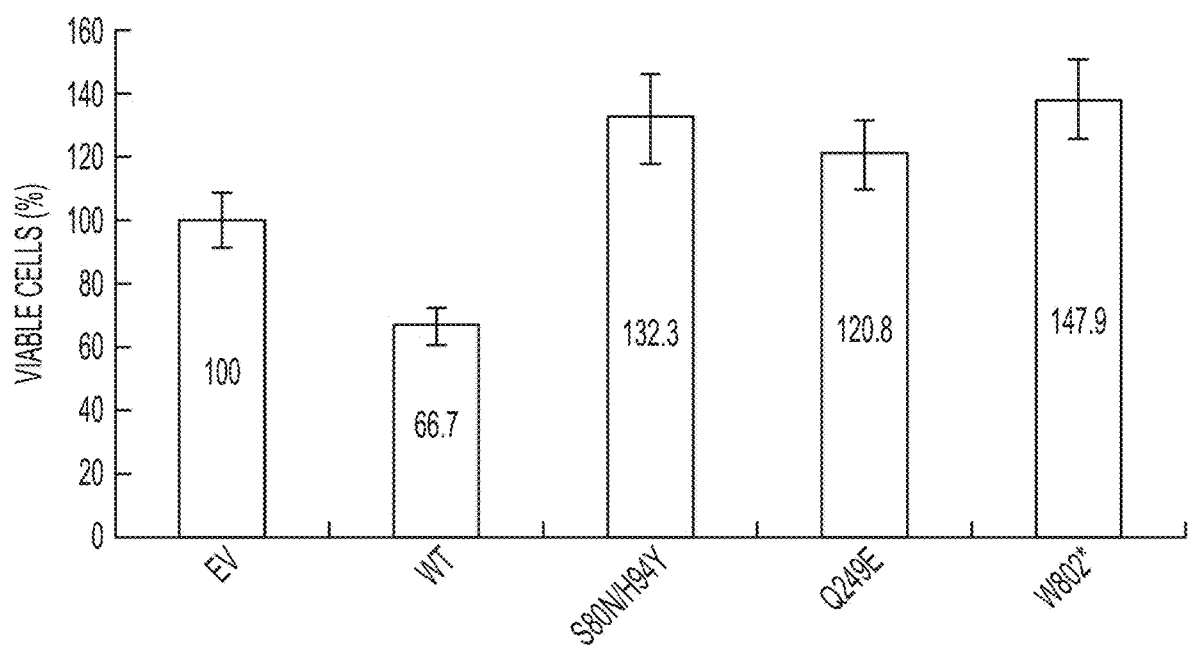
Figure 7C:
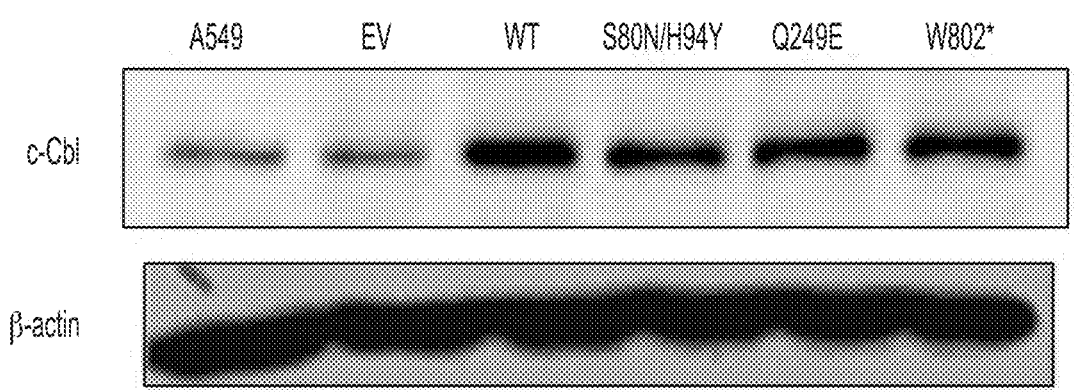

The effect of a representative c-CBL mutant from each of the three ethnic backgrounds on lung cancer cell viability in cell lines was determined. S80N/H94Y double mutation, Q249E, and W802* were identified in lung tumor samples obtained from a Caucasian, a Taiwanese and an African-American, respectively. As described above, the c-CBL wild-type (WT) and the above three mutants were expressed after cloning them into pAlterMax vector in A549 cells. These cells express relatively low basal levels of endogenous c-CBL. Transfection efficiency was comparable between different groups, and the number of cells transfected with c-CBL wild-type construct was about 70% compared to control cells that were transfected with the empty vector. Cells transfected with S80N/H94Y, Q249E and W802* c-CBL mutant constructs resulted in increased number of viable cells that was 132.3%, 120.8% and 147.9% higher respectively, relative to the empty vector control-transfected cells and significantly different from the wild-type construct (p=0.022, p=0.049, and p=0.008, respectively) (FIG. 7B). Relative levels of c-CBL protein in whole cell lysates prepared from samples obtained from a parallel experiment were determined. The c-CBL protein levels in samples representing untransfected and empty vector transfected cells were comparable, and those representing the c-CBL WT and the three c-CBL mutants were comparable (FIG. 7C).

Effect on Cell Cycle.

Figure 7D:
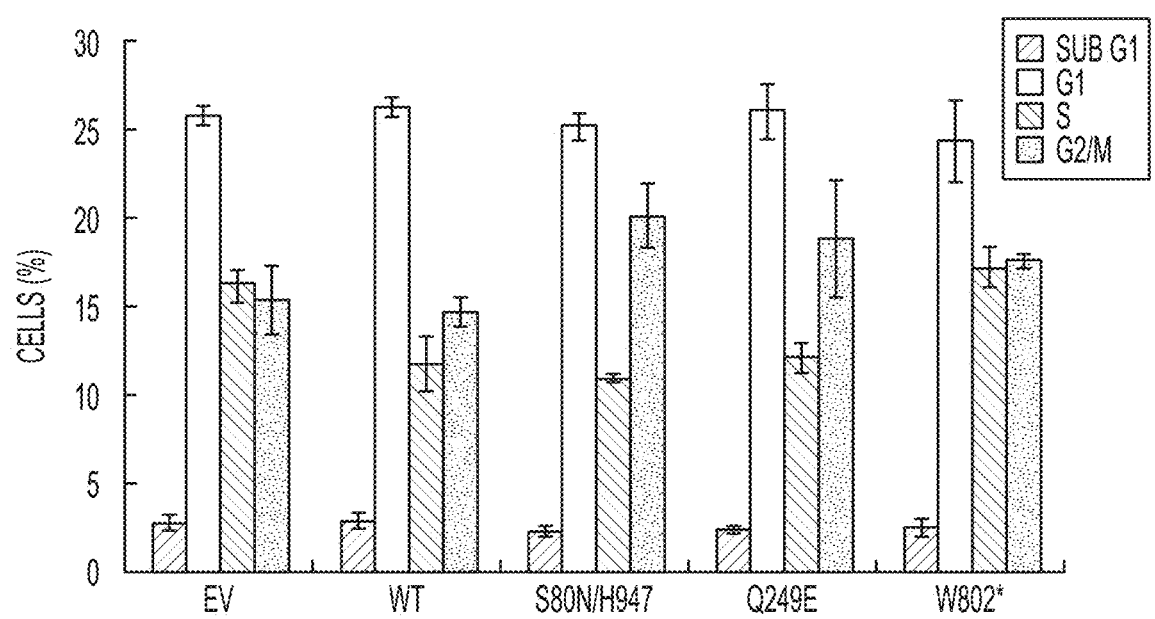

To investigate if the increases in cell viability in different c-CBL mutants are due to increased cellular proliferation, a cell cycle analysis was performed. A549 cells were transfected with the c-CBL WT or the three different mutants: S80N/H94Y, Q249E and W802*. The empty vector transfectant was used as a control. Forty-eight hours after transfection, cell cycle analysis was performed as described herein. There was no significant change in the subG1, G1 or the S phase of the cell cycle among the different mutants compared to the WT construct (p=0.64, p=0.40, and p=0.28, respectively). The G2/M phase of the cell cycle showed an increase in cell numbers for the three mutants, S80N/H94Y, Q249E and W802*, when compared to the WT but again the difference was not statistically significant (p=0.25) (FIG. 7D).

Effect on Cell Motility.

Figure 8B:
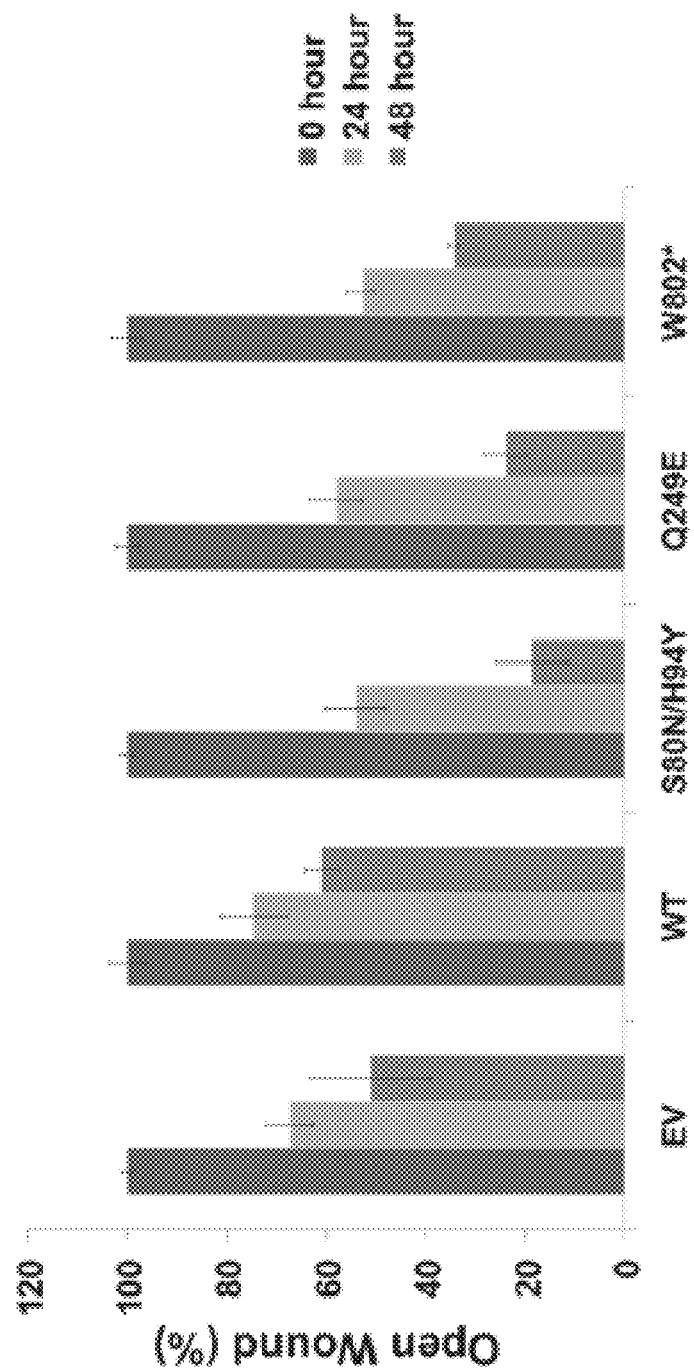

To investigate the effect of the expression of the above three c-CBL mutants on cell migration, a wound healing assay was carried out as described herein. The closing of the scratch or the wound was monitored at 0, 12, 24, 36, and 48 h. (FIG. 8A). In all the samples that represented cells transfected with mutants, the wound gap was much smaller than that seen in the sample that represented cells transfected with c-CBL WT (p<0.001). The rate of wound closure was also determined for all the five groups. At 48 h, wild-type c-CBL transfectants showed 61.1% open wound, while the S80N/H94Y, Q249E and W802* mutants showed 18.7%, 23.9% and 34.3% open wound, respectively (p<0.001) (FIG. 8B).

c-CBL Knockdown Increases Cell Viability.

Figure 9A:
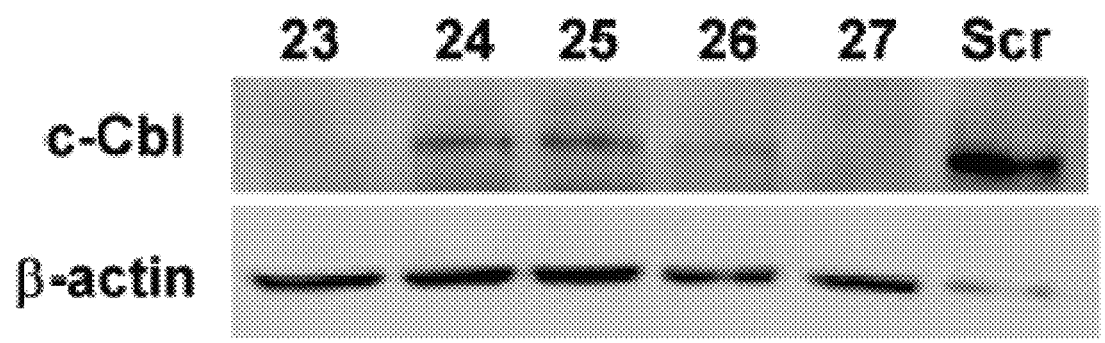
FIGS. 9A and 9B show data using H358 cell line clones.
Figure 9B:
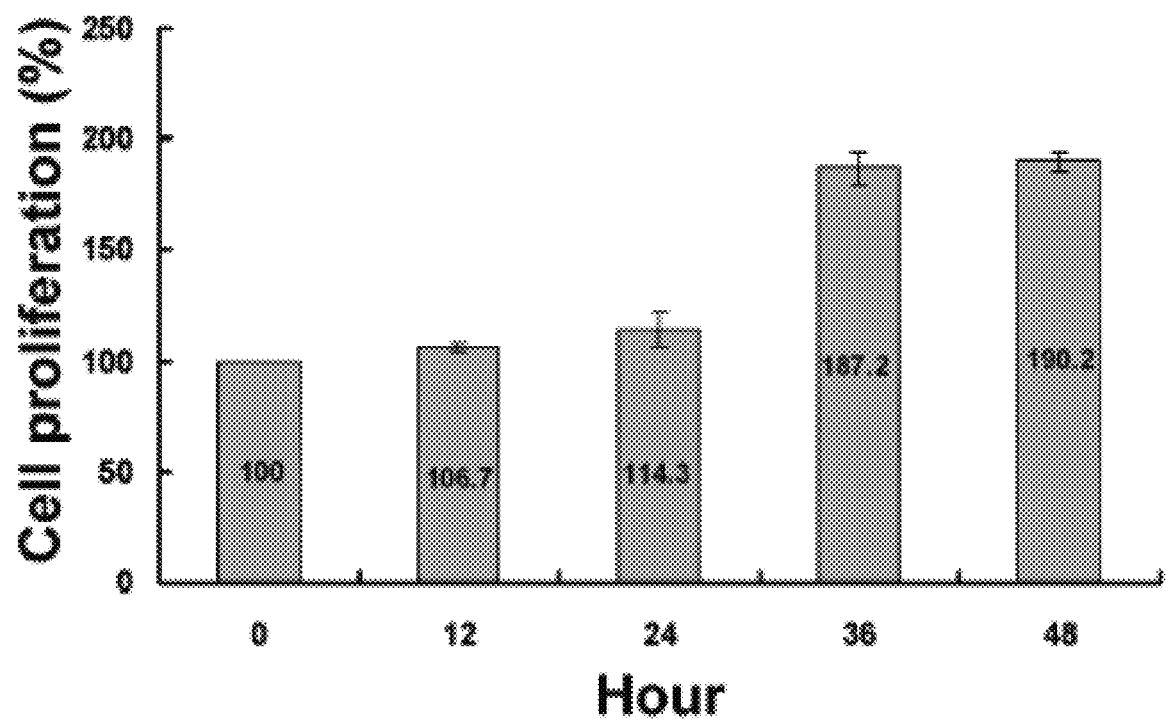

The effect of c-CBL knockdown in lung cancer cells was tested. Compared to A549, H358 lung cancer cells express relatively high levels of endogenous c-CBL. c-CBL expression was knocked down using lentiviral construct that expressed c-CBL specific shRNA, and this expression was compared to the expression in cells that were transduced with scrambled shRNA. Several clones that revealed varying degrees of c-CBL knockdown showing different levels of c-CBL lentiviral shRNA knockdown efficiency were identified (FIG. 9A). Of all the clones tested, Clone 27 was chosen for further experiments. Equal amounts of cells were seeded in a 6-well plate, and the cell proliferation was measured at various times and the results are depicted in FIG. 9B. The number of cells increased in a time dependent fashion from 100 to 190% relative to scrambled shRNA as control in a span of 48 h (p=0.0002) (FIG. 9B). The cell cycle phases in H358 cells that were knocked down with c-CBL shRNA were analyzed and compared with the scrambled shRNA. There were no discernable differences between these two constructs in the different phases of the cell cycle.

The results demonstrated that c-CBL was somatically mutated (or had LOH) in lung cancer cells. Accordingly, it is contemplated that c-CBL can significantly contribute to enhanced cell viability and motility. The results also demonstrated that there was also a high prevalence of LOH with respect to c-CBL in lung tumors that harbored MET or EGFR mutations.

The results demonstrated the occurrence of c-CBL mutations in lung cancer patients, especially with different ancestral variations. Mutations in c-CBL have been recently reported in juvenile myelomonocytic leukemia and myeloid malignancies. In the AML study, the mutation R420Q located in the junction of the RING finger and the linker region inhibited FMS-like tyrosine kinase 3 (FLT3) internalization and ubiquitination (Sargin et al., 2007), thus contributing to the gain-in-function for the RTK. In addition, mutations such as H398Y, C384R, and L380P have been mapped to the RING finger domain and the linker region of c-CBL that is required for its E3 activity. (Caligiuri M A, et al., Blood 110: 1022-1024 (2007); Grand F H, et al. Blood 113:6182-6192 (2009); Dunbar A J, et al., Cancer Res 68: 10349-10357 (2008); Sanada M, et al. (2009) Nature 460: 904-908; and Reindl C, et al. (2009) Clin Cancer Res 15: 2238-2247). Additionally, homozygous mutations in the RING finger domain of the c-CBL gene were described as a result of acquired Uniparental Disomy (UPD). The results indicated LOH at 11q23 locus, and these are mutually exclusive from missense mutations of c-CBL. The somatic mutations were all heterozygous. The mutations in AML led to abrogation of the E3 activity, leading to prolonged RTK activation. In addition mutants located on the linker region surrounding the RING finger domain exhibited enhanced AKT signaling in response to cytokine stimulation. In addition, in NH3T3 cells, it has been shown that neither mutations in the RING finger nor the linker region cause transformation; however, while certain mutations perturb the ubiquitination, others affect receptor recycling and prolong kinase activity. (Thien C B and Langdon W Y (2001) Nat Rev Mol Cell Biol 2: 294-307).

The results demonstrated that some c-CBL mutations were mapped not only to the RING finger domain, but also to the TKB domain, proline-rich domain and the C-terminal region, but none mapped to the linker region as reported in the AML studies described above (Caligiuri et al., 2007; Grand et al., 2009; Dunbar et al., 2008; Sanada et al., 2009; Reindl C, et al. (2009) Clin Cancer Res 15: 2238-2247). In addition, eight mutants that we detected were found in different ethnic backgrounds. For example, S80N/H94Y, Q249E, and W802* were detected in Caucasians, Taiwanese and African-Americans, respectively. The results demonstrate not only the difference between lung cancer and other cancers, but also genetic polymorphism among different races in the same cancer. There is a large disparity between African-American and other ethnic populations with lung cancer. It has previously been shown that there is a low frequency of EGFR and MET mutation in African-Americans as compared with Taiwanese and Caucasians. In the results described herein, three mutations that are unique to the African-American ethnicity were found.

c-CBL plays an important role in down regulating RTK mediated signaling through K63 poly-ubiquitination and subsequent downregulation of RTKs followed by lysosomal degradation. Mono-ubiquitination or ubiquitinated with K63-linked chains of substrates by c-CBL may lead to enhancement of biological and biochemical functions. Ubiquitin and ubiquitin-like proteins in protein regulation. The analyzed mutations indicated that the E3 activity of c-CBL on EGFR remained intact and that the EGFR levels in the various mutants remained the same. It is contemplated that multiple kinases, both RTKs and non-RTKs, could be acted upon by c-CBL, including ERBs, PDGFR, FMS, MET, c-Kit, VEGFR, FLT-1, RON, FGFR, IR, as well as SYK, FYN, LCK, FGR, LYN and c-ABL.

It has been previously shown that activating c-CBL mutation downregulates EGFR signaling and decreases cellular proliferation and migration in breast cancer cell lines. Although the role of c-CBL in the negative regulation of RTKs (and as a potential tumor suppressor) is well substantiated, studies in cancer cells have revealed both tumor suppressor and tumor promoting activities, depending on the type of c-CBL mutation and the number of alleles at the c-CBL locus. Consistent with these previous studies, the results related to the three c-CBL mutants described herein demonstrate that the mutants have both tumor growth and metastasis promoting properties. Although these mutants are outside of the RING finger or the linker region of c-CBL, it is contemplated that their downstream effects can be significant so as to cause increased proliferation and migration. The results also indicated that LOH for c-CBL was found in a significant number of samples that harbored MET or EGFR mutations. It is contemplated that about 7% of lung tumor samples can be likely to have c-CBL mutations and an additional 22% can be likely to harbor c-CBL-related LOH, making c-CBL a highly mutated molecule in lung cancer.

Previous studies have shown that East Asians with lung cancers have relatively high frequencies of gain-of-function of mutations in RTKs such as EGFR and MET. In a cohort of Japanese patients, an activating MET mutation was identified in the splice region that deletes the juxtamembrane domain that is involved E3 activity of c-CBL. The same study also found that activation of MET is mutually exclusive of EGFR, KRAS and HER2 gene mutations. During the experiments described herein, significant numbers of such mutations in lung tumor samples obtained from African-Americans (n=29) and Caucasian (n=50) patients were not detected. In the experiments described herein, one MET mutation was identified in each of the groups whereas 1 and 3 EGFR mutations were identified in the African-American and Caucasian cohorts, respectively. EGFR mutations have previously been identified as one of the key mutations affecting lung adenocarcinoma patients in a comprehensive study of 188 patients. The experiments described herein encompassed different histologies of NSCLC. However, the published series did not find any mutations in c-CBL or MET; in contrast, the experiments described herein encompassed different subtypes of NSCLC. It has recently been shown that MET mutations in lung cancer are in majority germline. To better understand the ethnic differences in the lung oncogenome, PAX transcription factors such as PAX5 and PAX8 that are highly expressed in lung cancers were examined; however, the results indicated that there was no preferential expression or mutations of the above genes in lung tumor samples of African-Americans. The results did demonstrate a relatively high frequency of c-CBL mutations in lung cancers, especially in the large cell type among Caucasians and particularly among African-Americans.

Example 3

Figure 10A:
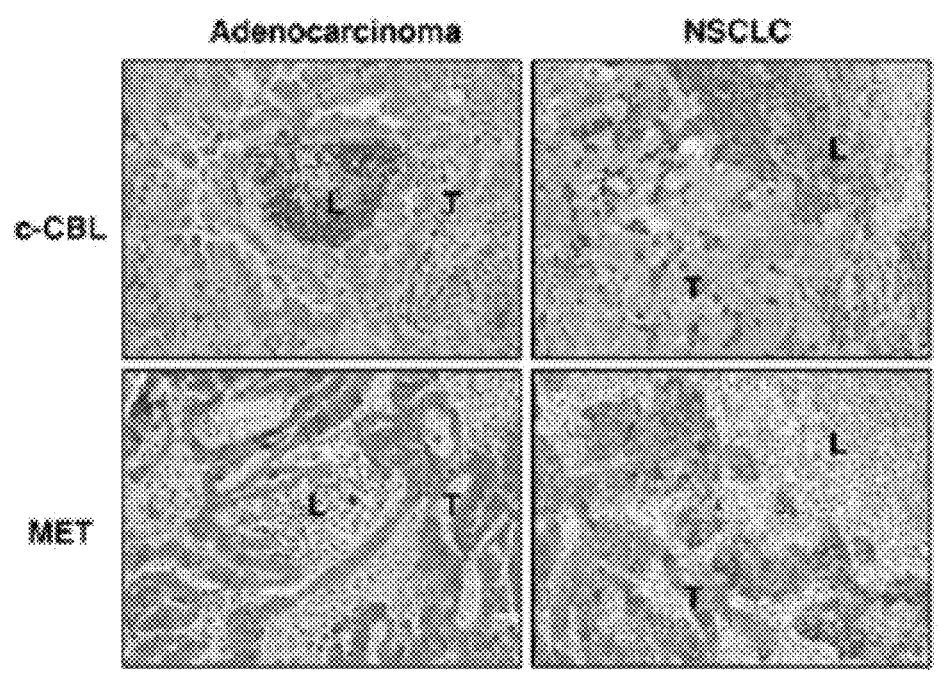
FIGS. 10A and 10B show MET and c-CBL staining.
Figure 10B:
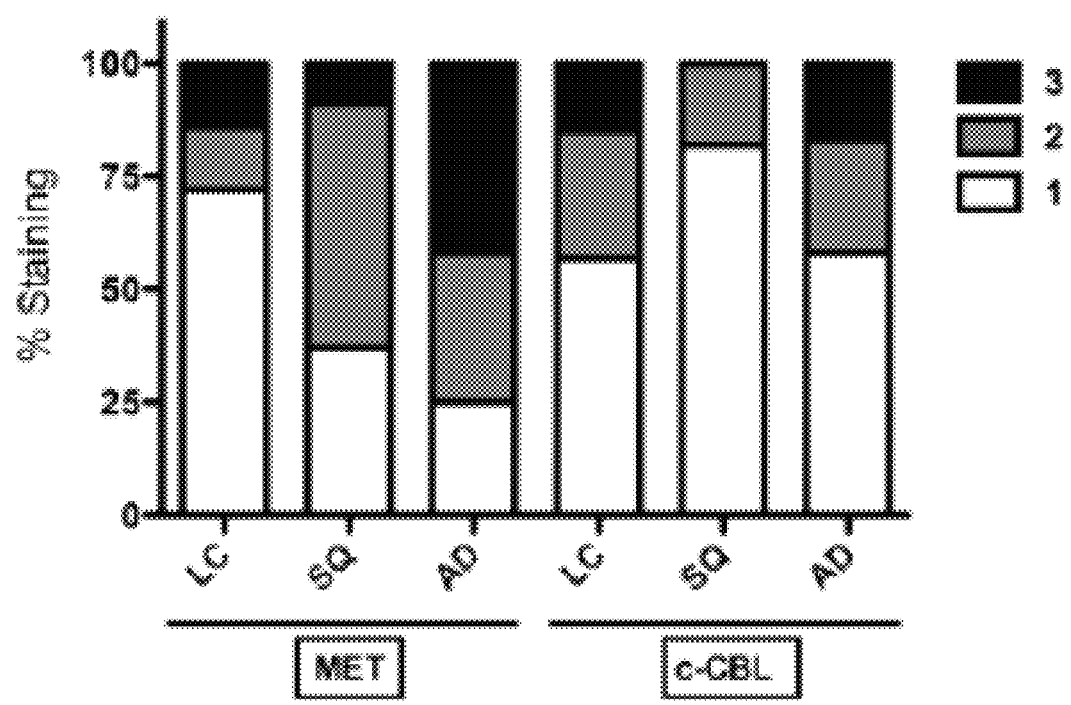

Adenocarcinoma and undifferentiated NSCLC were stained with c-CBL and MET antibodies on whole tissue sections. The results demonstrated stronger MET expression throughout the tissue sections with weaker c-CBL staining in localized areas of the section (n=29, with 11 adenocarcinomas, 11 squamous cell carcinomas, and 7 large cell carcinomas). c-CBL staining was intense in the lymphocytes (L) and weak in the tumor (T) whereas the staining pattern was the reverse for MET. FIG. 10A shows representative c-CBL and MET staining in two different patient samples, one adenocarcinoma sample and one NSCLC sample. The staining intensity was analyzed in these 29 samples among three different histologies, and the results show relatively intense MET staining with relatively low to moderate c-CBL staining. The results are summarized in FIG. 10B. The relative intensity of expression of c-CBL was higher in large cell carcinoma as compared to other histologies. Also, c-CBL mutations were greater in large cell carcinomas.

Figure 11:
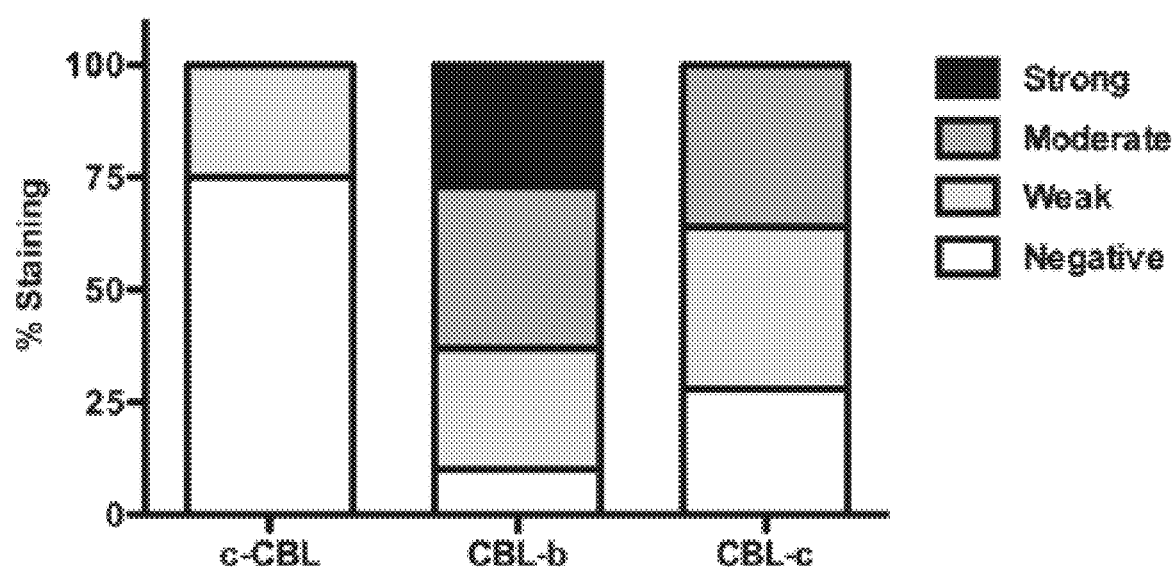
FIG. 11 shows CBL isoform staining in the lung cancer cells that were analyzed as described in Example 3, below. The bar graph shows the intensity of c-CBL (n=12) staining compared to CBL-b (n=12) and CBL-c (n=12) staining in lung cancers (Adapted from www.proteinatlas.org). As depicted, most lung cancer tissues had no or low c-CBL staining but high CBL-b and CBL-c staining.

The results from the archival database at www.proteinatlas.org were supportive of the results described herein, which found negative or low staining for c-CBL in NSCLC. The staining of c-CBL was relatively low compared to CBL-b and CBL-c staining (FIG. 11). Specifically, MET staining was more intense in squamous cell carcinoma (SQ, n=1) and adenocarcinoma (AD, n=1) compared to c-CBL, which was low to moderate in most samples except large cell (LC, n=7).

Example 4

Figure 12:
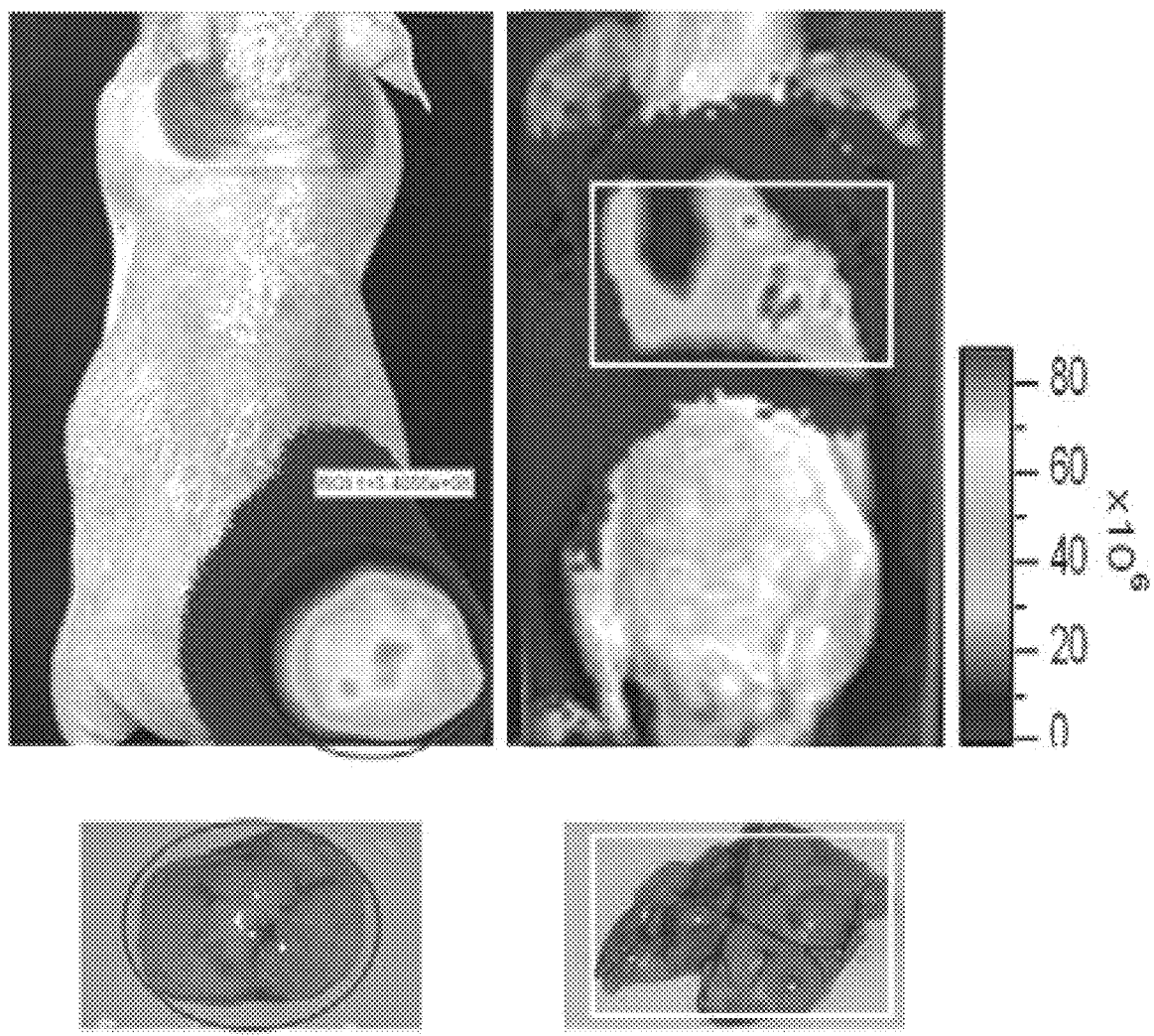
FIG. 12 shows images of a tumor growth and xenograft model that was analyzed in Example 4. Tumor growth of luc gene stably transfected into NSCLC (A549 luc) xenograft in ectopic (left) and metastatic (right) athymic nude mice models. Tumor and metastatic A549 luc tumor nodules were visible on the lung surfaces (shown in the lower panel).

Nude mice were injected intravenously (tail vein) with 10 million A549 NSCLC cells stably transfected with luciferase (luc) construct. The homing of these cancer cells to lungs, lymph nodes and the spleen were imaged at regular intervals (once weekly) by whole body imaging using iBOX imaging system. The mice were also injected subcutaneously to measure tumor growth rates in different cell lines as well as lines having different RTK mutations. Animals were examined daily for six weeks for weight loss and other signs of morbidity and were terminated if found to be distressed. All animals were terminated at 6 weeks in a humane way. At weekly intervals, the tumors were scanned by whole body imagers using the iBOX imaging system. After subtracting background fluorescence, signals in the images were calculated using Igor Pro software, and the tumor size was determined. A representative example image is shown in FIG. 12.

Example 5

Figure 13:
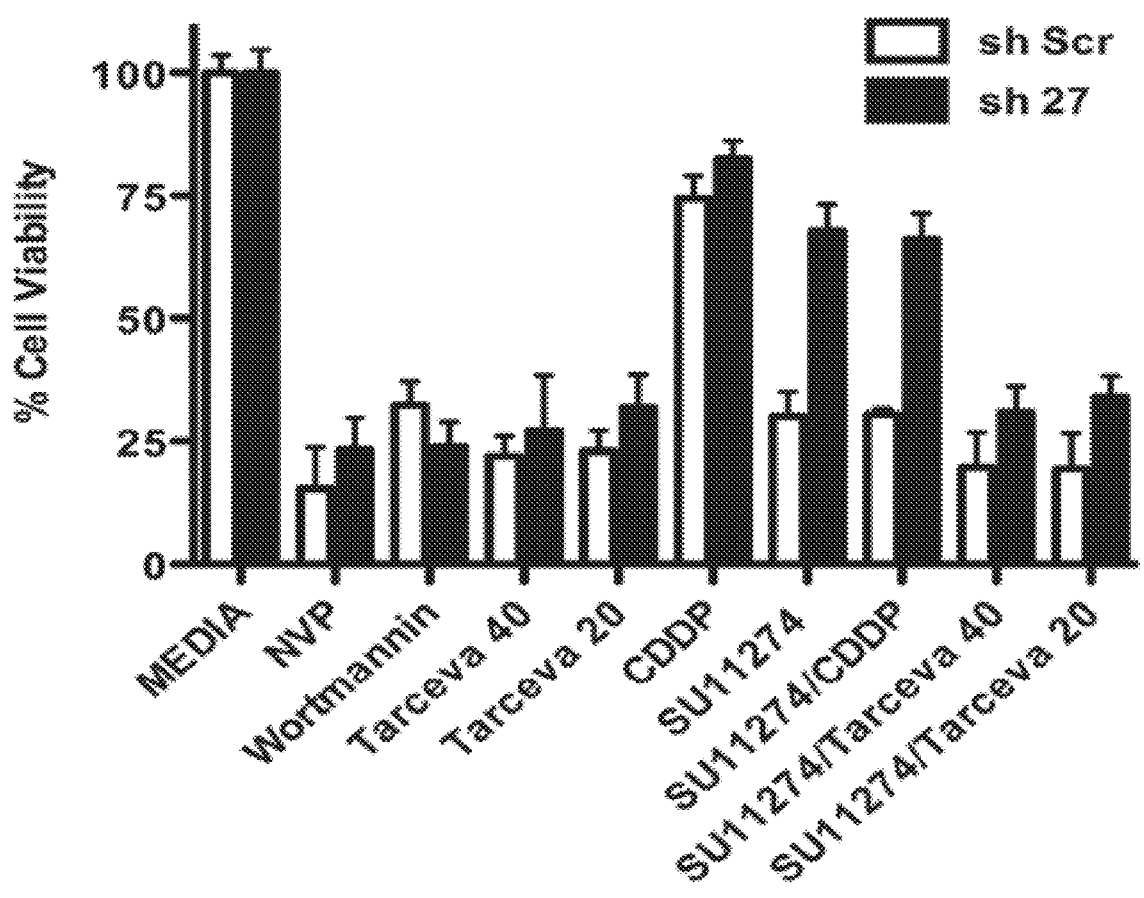
FIG. 13 shows that knockdown of c-CBL in H358 cells reduced the cells' susceptibility to killing by a c-MET inhibitor, as described in Example 5, herein. H358 clone 27 cells expressing high levels of c-CBL were knocked down using a lentiviral construct (sh 27). Cells were treated with the indicated RTK inhibitors, PI-3K inhibitors or cisplatin (CDDP). Live cells were assessed 72 h after drug treatment using a MTT assay.
Figure 14:
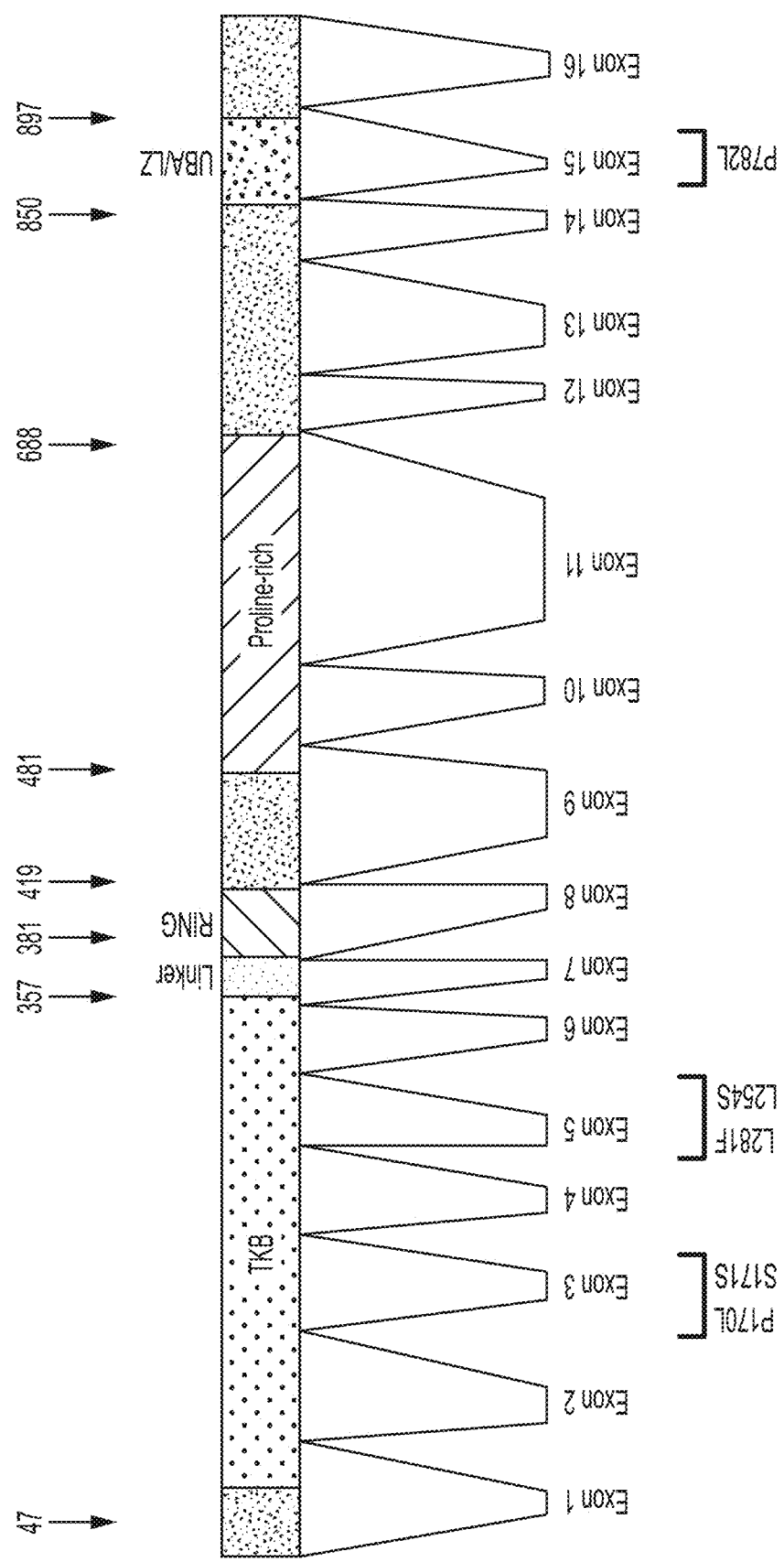
FIG. 14 shows the positions of five c-CBL mutations found in head and neck cancer, four in the TKB region (P170L, S171S, L281F, L254S) and one in the C-terminal region (P782L). The mutations were identified in patient samples. All mutations were in different patients.
Figure 15A:
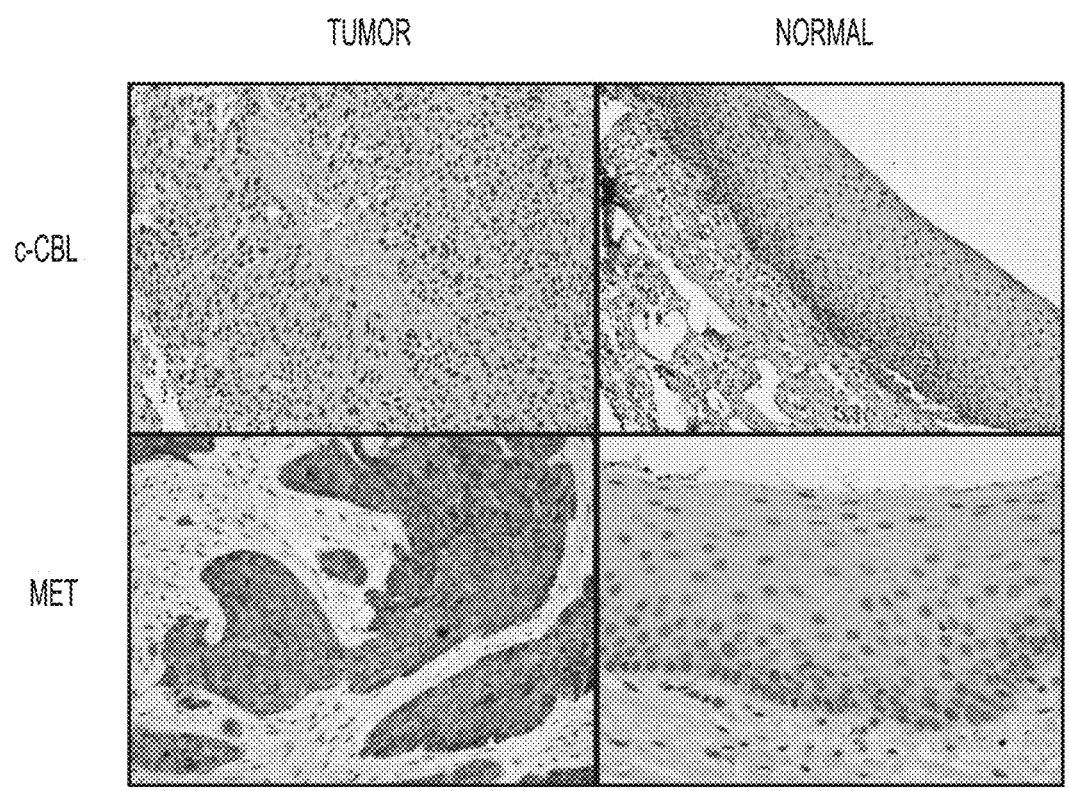
FIGS. 15A, 15B, and 15C show information related to the expression of c-CBL and MET in head and neck squamous cell carcinomas (HNSCC) tumor specimens.
Figure 15B:
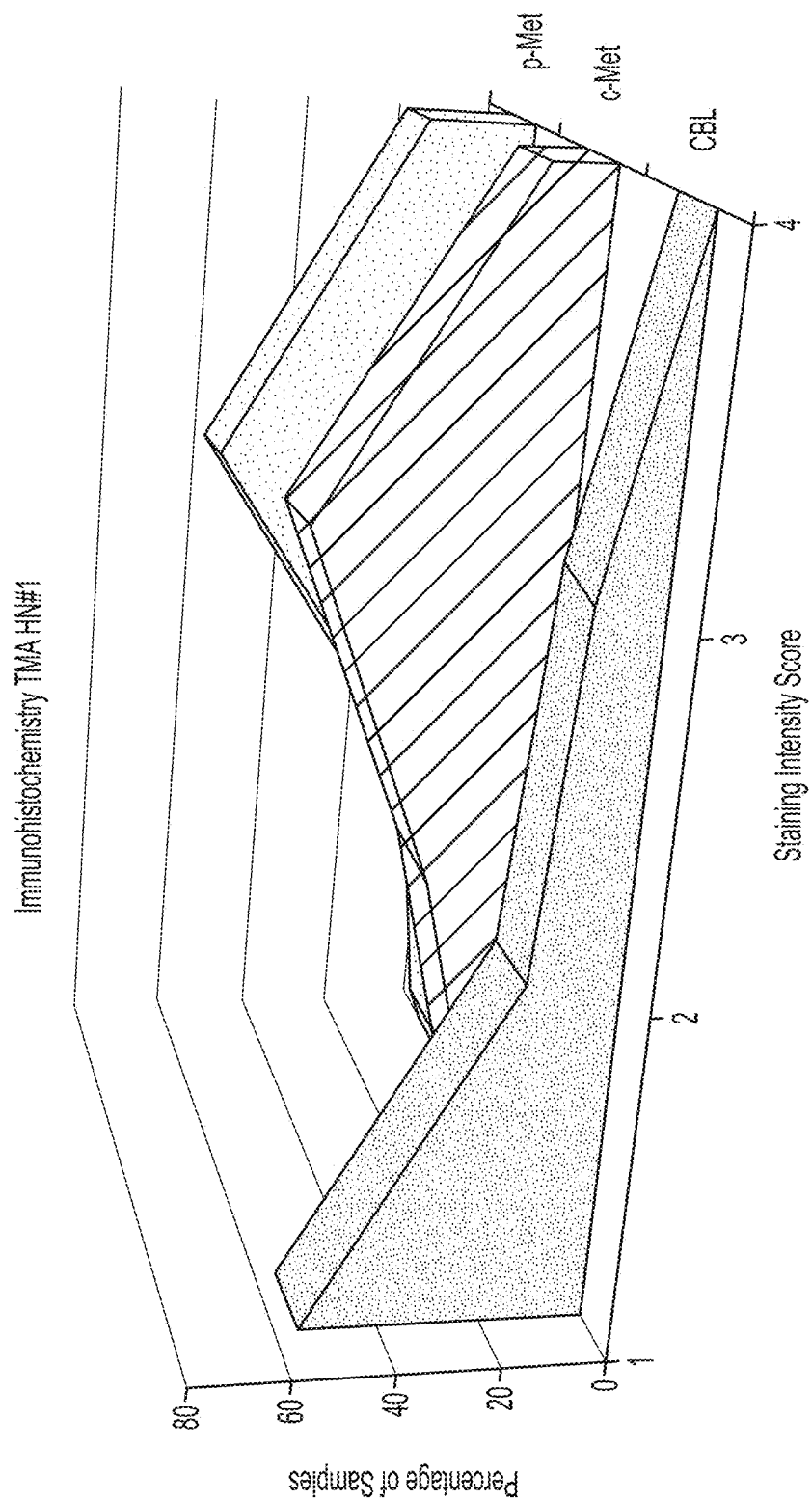
Figure 15C:
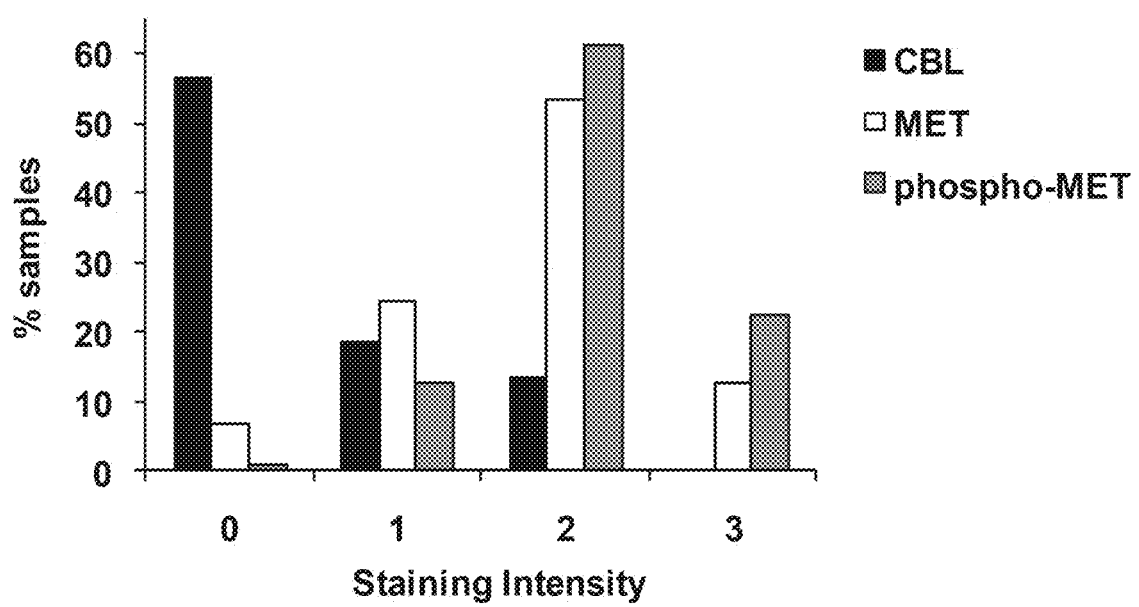
Figure 16:
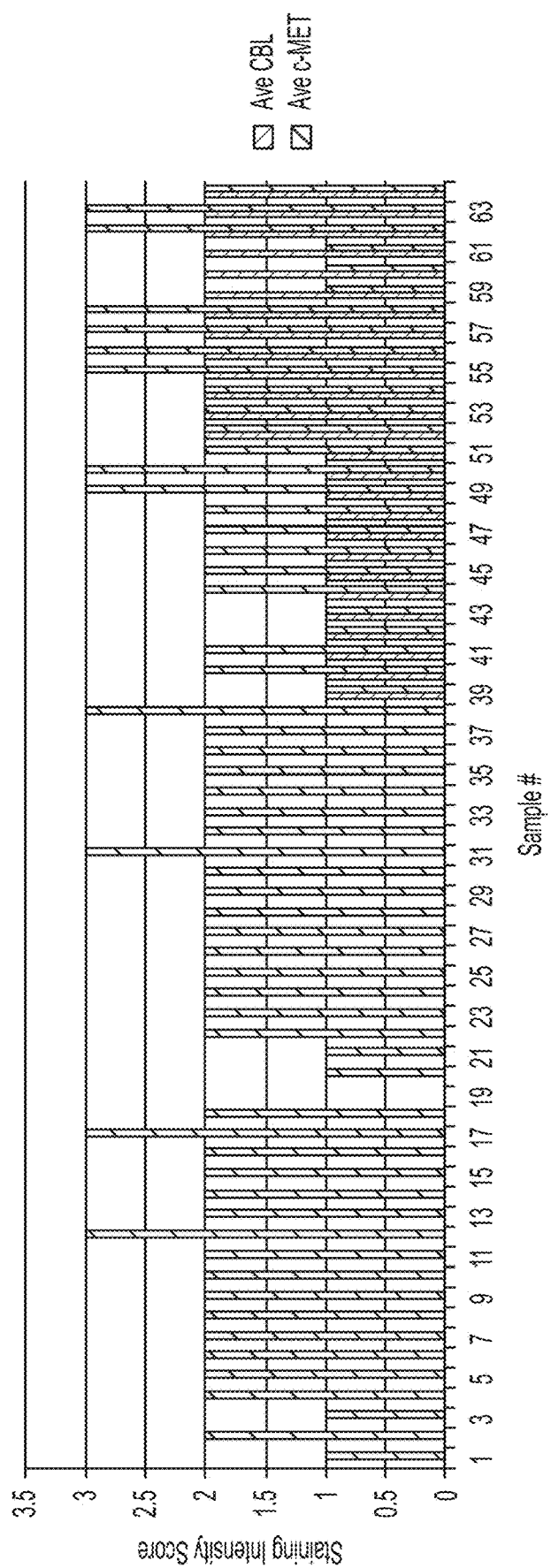
FIG. 16 shows CBL versus MET expression in each sample. The average Met and CBL TMA staining intensity scores in the same patient sample for several samples.
Figure 17:
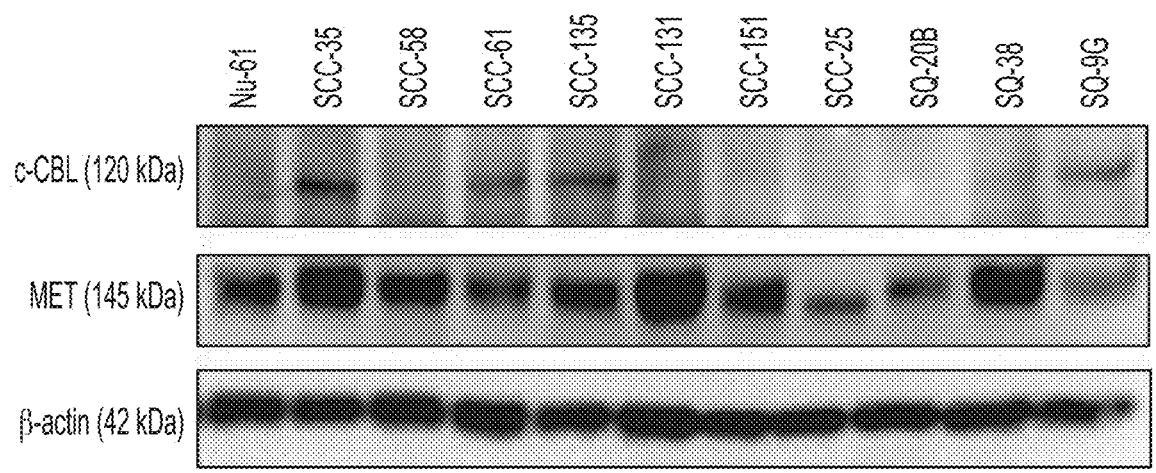
FIG. 17 shows information related to c-CBL and MET expression in HNSCC cell lines. Whole cell lysates from 11 HNSCC cell lines were subjected to SDS-PAGE, then immunoblotted using the indicated antibodies. j3-actin served as the loading control.
Figure 18A:
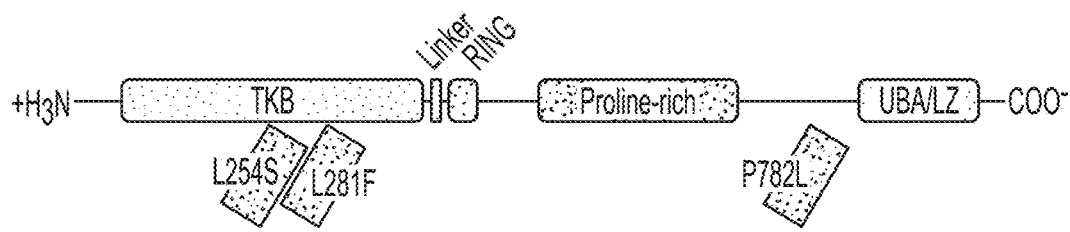
FIGS. 18A and 18B show c-CBL mutations in HNSCC.
Figure 18B:
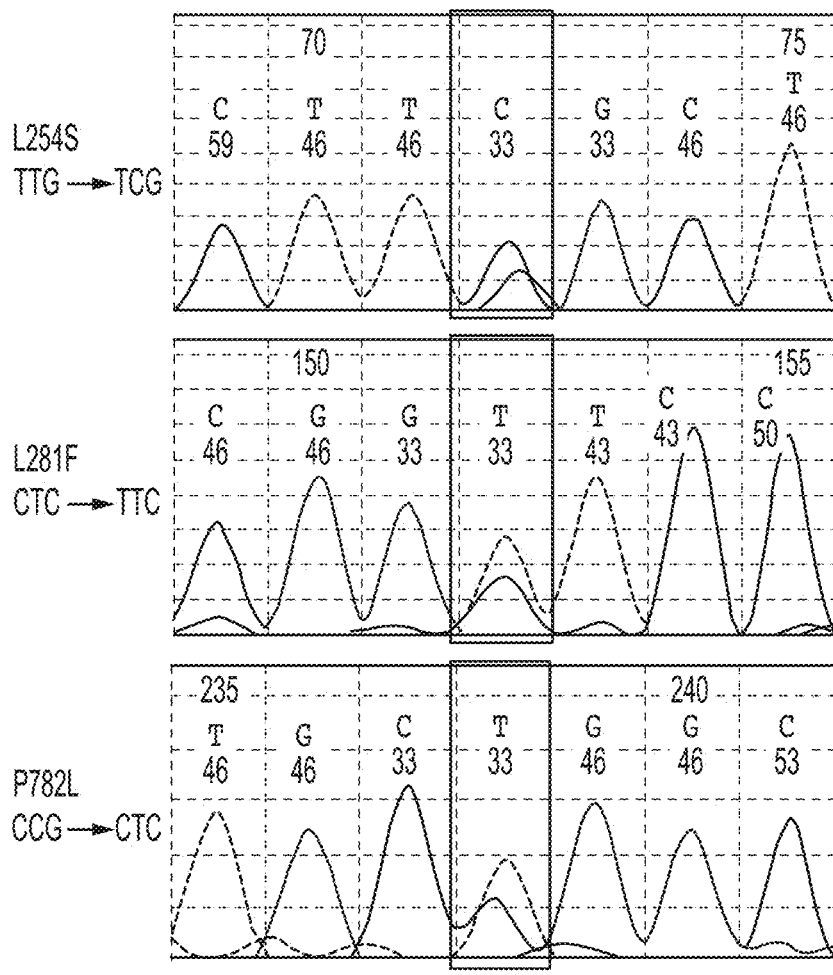
Figure 19A:
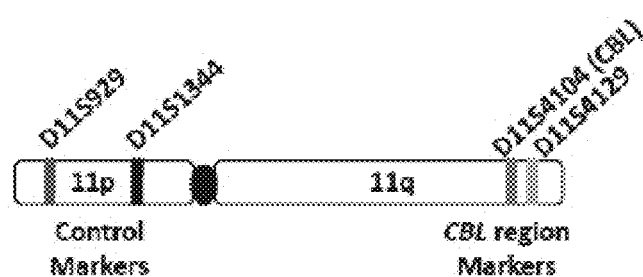
FIGS. 19A and 19B show information related to LOH at the c-CBL locus in HNSCC. LOH analysis of 23 tumor and paired normal patient samples. After PCR amplification using chromosome 11 specific microsatellite primers, the PCR product was separated by capillary electrophoresis and bands were quantified according to intensity.
Figure 19B:
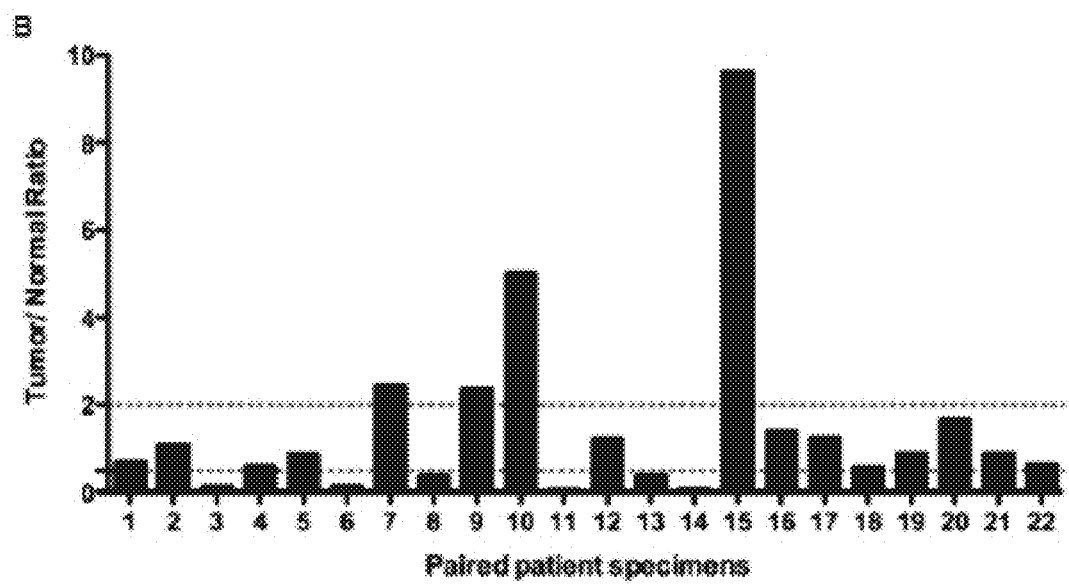
Figure 20:
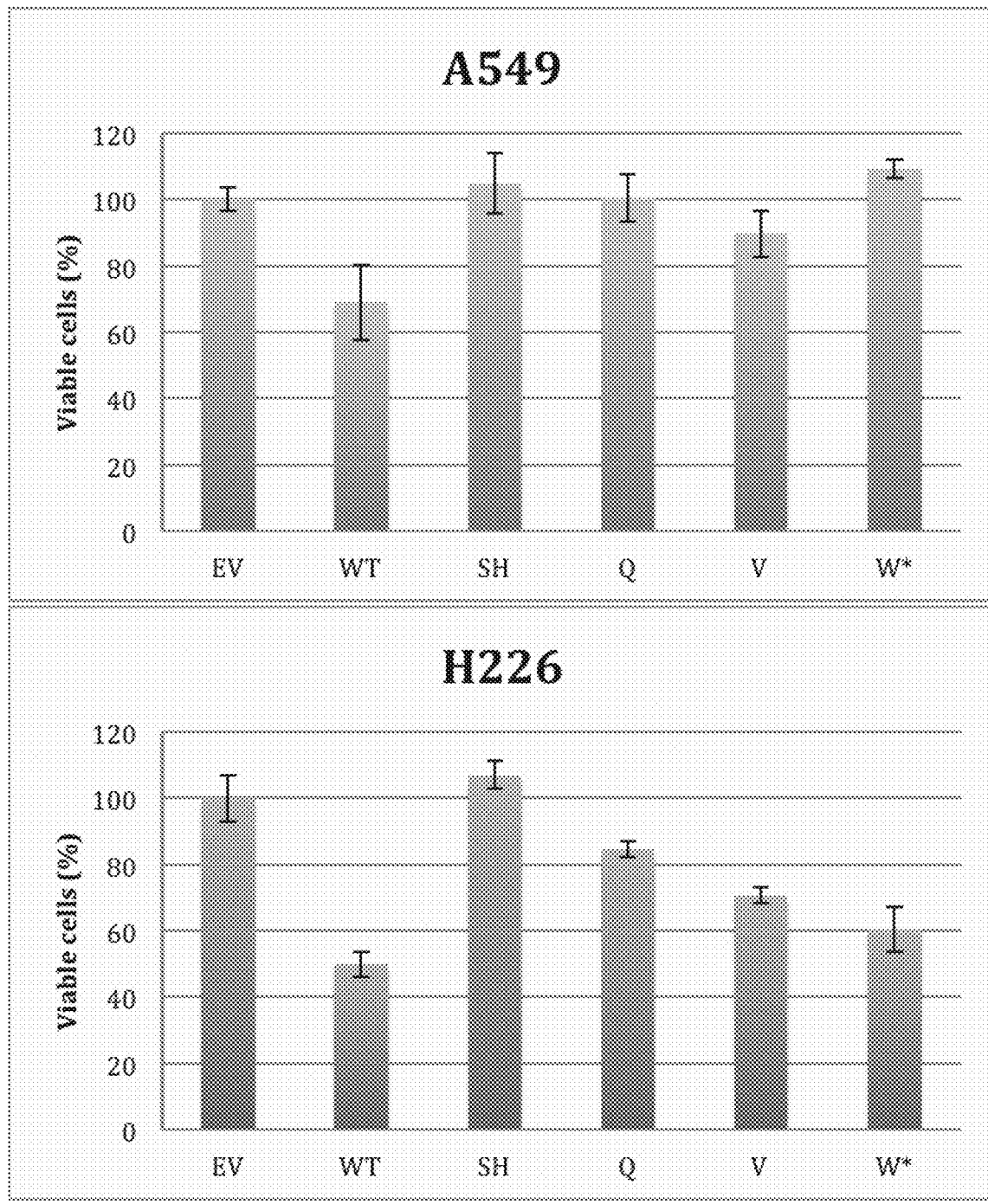
FIG. 20 shows the effect of representative c-CBL mutants, S80N/H94Y (SH) double mutation, Q249E (Q), V391I (V) and W802* (W*), on lung cancer cell viability in A549 and H226 nonsmall cell lung cancer cell lines.

The effects of silencing wt c-CBL in combination with a variety of drugs that inhibit EGFR (erlotinib [Tarceva]), PI-3K (NVP, Wortmanin), MET (SU11274) on the growth of H358 NSCLC cells that endogenously express c-CBL-Wt were investigated. The H358 cells, which expressed high levels of c-CBL, were knocked down using a lentiviral construct (sh 27, directed against c-CBL-Wt in H358 clone 27 cells (black), or the sh SCR scrambled RNA control (white)). Cells were treated with RTK and P1-3K inhibitors, cisplatin (CDDP). Live cells were assessed 72 hours after drug treatment using an MTT assay. The results are summarized in FIG. 13. As shown in FIG. 13, silencing c-CBL-Wt did not have a discernible effect on the percentage of live cells (media control); however, silencing c-CBL-Wt significantly reduced the ability of SU11274 (also referred to as SU) to kill NSCLC cells. A comparison of the c-CBL-Wt expressing cells (white) and the c-CBL-Wt knockdown cells (black) treated with SU11274 either alone or in combination with other treatments, showed that c-CBL-Wt knockdown cells were less susceptible to treatment with a c-MET inhibitor.

Example 6

Tissue Samples

Tumor and paired adjacent normal tissues were obtained from patients that received treatment.

Tissue Microarray and Immunohistochemistry

Tissue blocks of patients with HNSCC that were treated at the University of Chicago Medical Center (diagnosed between 1992 and 2005) were selected for the study. Tumor microarray (TMA) was built using the ATA-27 Arrayer from Beecher Instruments as previously described (Ma et al., Genes Chromosomes Cancer 2008). In brief, tissue cores (1.5-mm punch) from biopsied tumor and adjacent normal tissues were precisely organized into a grid and embedded in paraffin. Each specimen was included in duplicate within the array. All slides were reviewed and scored by two independent pathologists. Differences in immunohistochemical scores were resolved by consensus. Each sample was scored using a 0 to 3+ scale, with 0 denoting no staining/no protein expression and 3+ denoting strong positive staining/high protein expression.

Immunoblotting

Cells were harvested and washed in 1×PBS, then lysed in ice-cold M-PER lysis buffer plus HALT protease and HALT phosphatase inhibitors (Pierce) for 10 minutes on ice. The lysates were centrifuged at 13,000 rpm for 10 minutes at 4° C., and protein content of the supernatant was determined. Total cell lysates (50 µg/well) were separated by SDS-PAGE electrophoresis and the gels transferred onto immobilon-P membranes (Whatman, Piscataway, N.J.). Membranes were blocked with 5% BSA in Tris-buffered saline containing Tween-20 (TBST) (1×TBS, 0.1% Tween-20) for 1 h at room temperature and incubated with the appropriate primary antibody at 4° C. overnight. Membranes were then washed three times with TBST and probed with the appropriate horseradish peroxidase (HRP)-conjugated secondary antibody (1:10,000) for 1 h at room temperature. The membranes were again washed three times in TBST and bands were visualized using Western blot chemiluminescence reagent (BioRad, Valencia, Calif.) on a Chemidoc Gel documentation system (BioRad). The following antibodies were used: c-CBL (Abcam), 1:500; MET (Invitrogen), 1:500; and 3-actin (Sigma), 1:10,000.

c-CBL Gene Mutational Analysis

Genomic DNA was isolated from formalin-fixed, paraffin embedded (FFPE) patient tissues using the QIAamp DNA Minikit (Qiagen) according to the manufacturer's instructions. Exons 2 to 16 of c-CBL were amplified and sequenced as previously reported (Tan et al., PLoS One 2010). The PCR conditions were as follows: 1 cycle—95° C. for 5 min; 30 cycles—95° C. for 30 s, 58° C. for 30 s, 72° C. for 1 min; 1 cycle—72° C. for 5 min. Sequencing was performed on the forward coding strand with confirmation of c-CBL alterations performed by sequencing the reverse strand. Mutational analysis was performed using Mutation Surveyor v2.61 (Softgenetics, State College, Pa.).

Figure 5D:
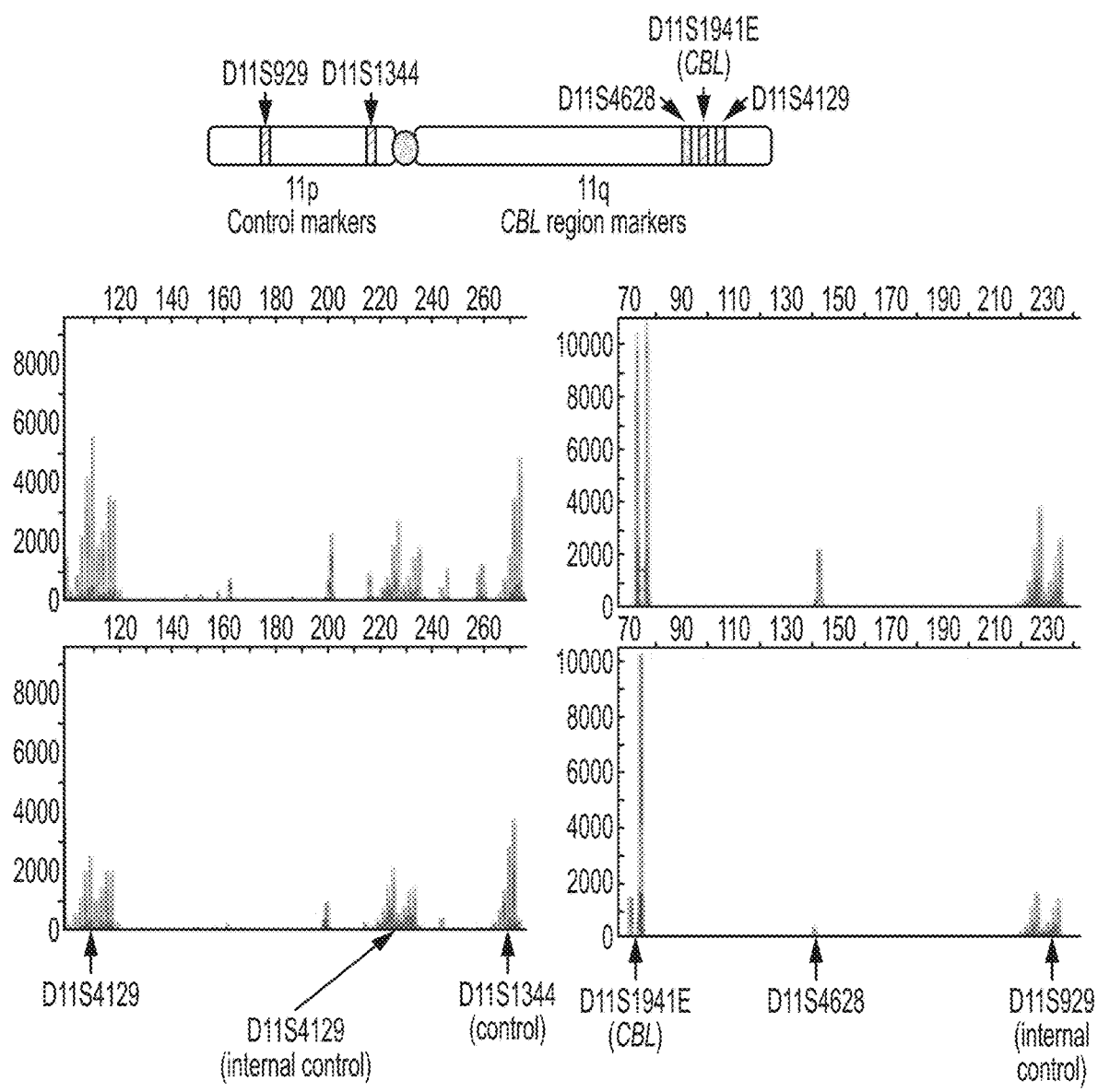

Loss of Heterozygosity (LOH) Analysis c-CBL LOH analysis was conducted as previously described (Tan et al., PLoS One 2010). Briefly, five microsatellites on chromosome 11 (3 within the c-CBL gene on 11q and 2 control markers on 11p) were selected for analysis (FIG. 5D). Genomic DNA was extracted from FFPE tumor samples and paired normal tissue. Marker D11S929 served as an internal control to check for consistency in PCRs and of peaks from capillary electrophoresis. PCRs were carried out in a volume of 10 µL that contained 1 µL genomic DNA (20-50 ng), 0.5 µM of each primer (1.0 µM total for each primer pair), 400 µM dNTPs, 1×PCR buffer containing MgCl2, and 0.2 U Taq DNA polymerase. The PCR conditions were: 5 min at 95° C.; 30 cycles of 30 sec at 95° C., 1 min at 60° C., 1 min at 72° C.; and 5 min at 72° C. Peak Scanner 1.0 (Applied Biosystems) was used to analyze the chromatograms. The ratio of the allelic areas was calculated for each tumor and paired normal DNA sample. When the qLOH (allelic ratio for the tumor peaks divided by the allelic ratio of paired normal sample) was ≤0.5 or ≥2.0 for c-CBL and at least one other 11q marker in at least two separate experiments, the sample was considered as having an allelic imbalance and interpreted as LOH.

Example 7

Cell Viability of Various c-CBL Mutants

The effect of representative c-CBL mutants (c-CBLMts), S80N/H94Y (SH) double mutation, Q249E (Q), V391I (V) and W802* (W*), on lung cancer cell viability in A549 and H226 nonsmall cell lung cancer cell lines was determined. Cell viability was measured by trypan blue exclusion and compared to empty vector (EV) control. c-CBL wild type (WT) and mutants S80N/H94Y (SH), Q249E (Q), V391I (V), and W802* (W*) showed 69%, 104.8%, 100.6%, 89.7%, and 109.1% cell viability respectively in A549 and 50%, 106.9%, 84.5%, 70.7%, and 60.3% respectively in H226 cells after 48 h transiently transfection.

c-CBLMts Exhibit Decreased c-Met Ubiquitination in NSCLC

A549 cells were transiently transfected with empty vector (EV) or c-CBL wild type (WT) and mutants' constructs (SH: S80N/H94Y, Q: Q249E, V: V391I, W*: W802*). At 48 h, whole cell lysates were immunoprecipitated (IP) with anti-c-Met Ab and immunoblotted (IB) with anti-ubiquitin Ab. IB with anti-HA Ab for transfection efficiency and j3-actin for loading control of the IP. The results showed the ubiquitination of c-Met were decreased in A549 cells that transiently expressed c-CBL mutants relative to wild type c-CBL cells.

Cell Survival of c-CBLMts after Treatment with c-Met and EGFR Inhibitors

Figure 21:
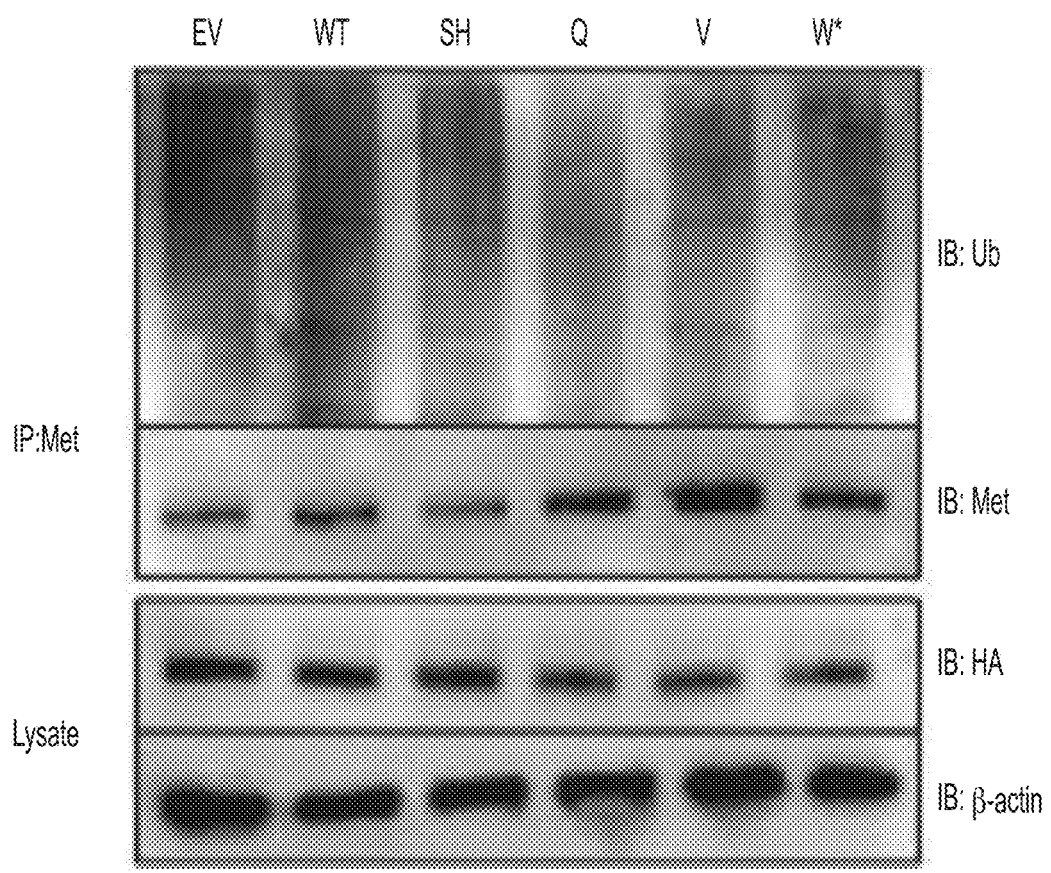
FIG. 21 shows immunoprecipitations (IP) with anti-c-Met Ab and immunoblots (IB) with anti-ubiquitin Ab of A549 cells transiently transfected with empty vector (EV) or c-CBL wild type (WT) and mutants' constructs (SH: S80N/H94Y, Q: Q249E, V: V391I, W*: W802*). The results showed the ubiquitination of c-Met were decreased in A549 cells.
Figure 22:
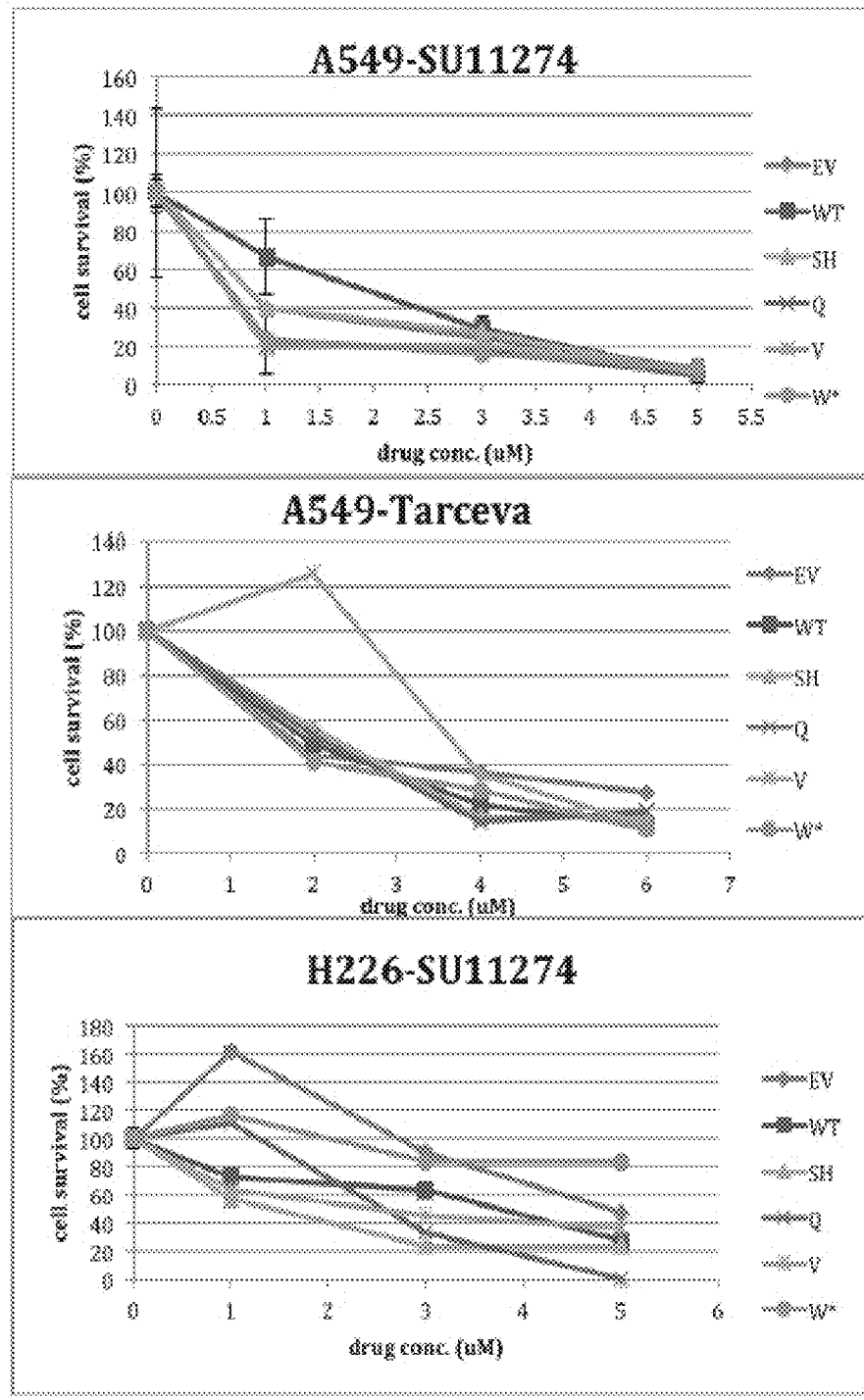
FIG. 22 shows the sensitivity of cancer cells to specific cancer therapeutics. The results in A549 cells showed c-CBL mutants had more sensitivity to c-Met inhibitor SU11274 than wild type c-CBL. The EGFR inhibitor, Tarceva, showed no differential effects on the A549 wild type and mutant c-CBL-transfected cells.
Figure 23:
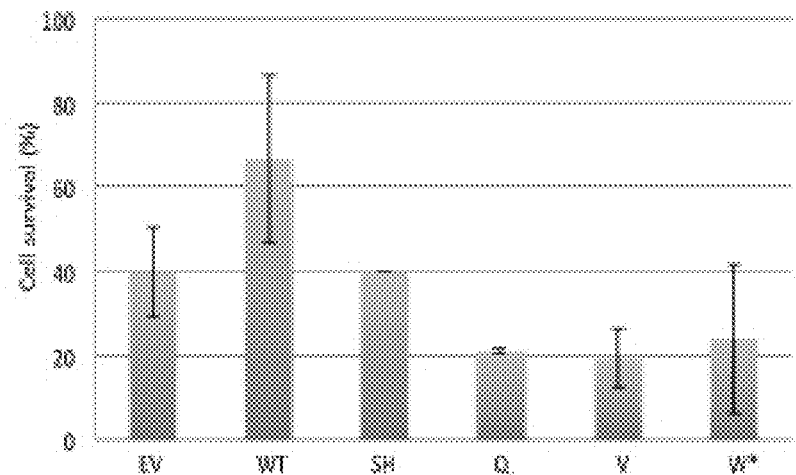
FIG. 23 shows the sensitivity of A549 cells containing of representative c-CBL mutants, S80N/H94Y (SH) double mutation, Q249E (Q), V391I (V) and W802* (W*) to 1 μM SU11274. c-CBL mutants are more sensitive than wild type c-CBL.
Figure 23:
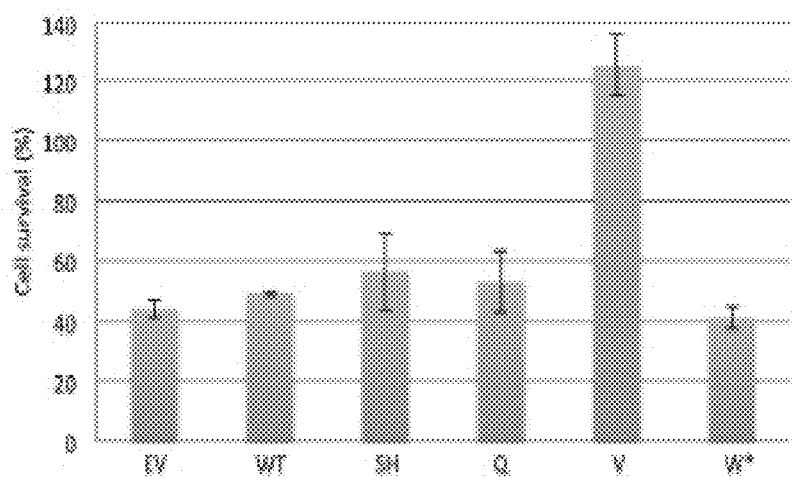
Figure 23:
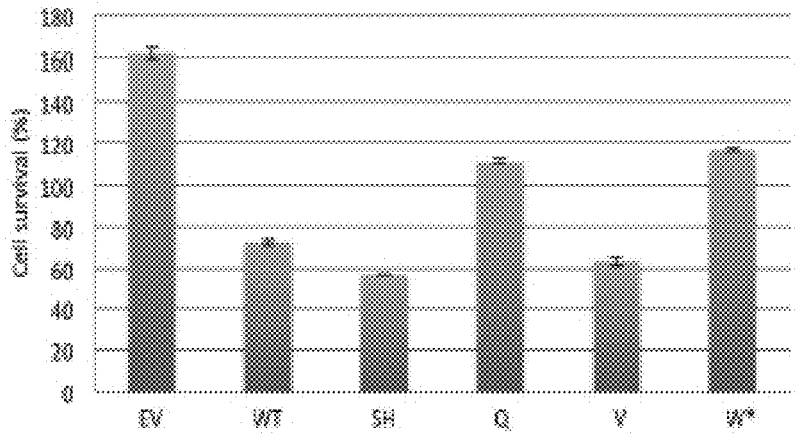

A549 and H226 cells were transiently transfected with empty vector (EV) or c-CBL wild type (WT) and mutants' constructs (SH: S80N/H94Y, Q: Q249E, V: V391I, W*: W802*). At 24 h, cells were recollected and seeded 5×104 cells/well in 24 well culture plate. Another 24 h, cells were treated with c-Met inhibitor SU11274 and EGFR inhibitor Tarceva in different concentrations. Cell survival was detected by cell counting after 48 h treatment. The results in A549 cells showed c-CBL mutants SH, Q, V, W* had more sensitivity to the c-Met inhibitor SU11274 than did A549 and H226 cells transfected with the wild type c-CBL. However, there is no difference with EGFR inhibitor Tarceva treatment. Transiently expressed c-CBL mutants showed a decrease in the ubiquitination of c-Met relative to wild type c-CBL cells (FIG. 21) A549 and H226 cells are generally accepted predictive cell models for carcinoma behavior, for example, NSCLC and head and neck carcinoma. The susceptibility of c-CBL mutant A549 and H226 cells to treatment with a c-MET inhibitor, for example, SU11274, is predictive of the susceptibility of a subject, such as a patient, diagnosed with cancer or having cancer to treatment with a c-MET inhibitor, for example, SU11274.

EQUIVALENTS

Those skilled in the art will recognize, or be able to ascertain, using no more than routine experimentation, numerous equivalents to the specific embodiments described specifically herein. Such equivalents are intended to be encompassed in the scope of the following claims.

What is claimed is:

1. A method of treating a human having lung cancer, the method comprising administrating to the human an effective amount of a c-Met inhibitor, wherein the lung cancer comprises cells determined to have a mutation in a gene designated Casitas B-lineage lymphoma (c-CBL), wherein the determined mutation is an amino acid change at positions S80N/H94Y, and wherein the c-Met inhibitor is a small-molecule c-Met inhibitor.

2. The method of claim 1, wherein the c-Met inhibitor is selected from the group consisting of SU11271 (Sugen), SU11606 (Sugen), HPK-56 (Supergen) or K252a (Merck).

3. The method of claim 1, wherein the lung cancer is Non-Small Cell Lung Cancer (NSCLC).

4. A method of treating a human having Non-Small-Cell Lung Cancer (NSCLC), the method comprising the steps of:
   i. selecting a human who has been diagnosed with NSCLC, wherein the NSCLC comprises cells determined to have a mutation in a gene designated Casitas B-lineage lymphoma (c-CBL), wherein the determined mutation is an amino acid change at positions S80N/H94Y; and,
   ii. administering to the human having the NSCLC an effective amount of a c-Met inhibitor, wherein the c-Met inhibitor is a small-molecule c-Met inhibitor.

5. The method of claim 4, wherein the c-Met inhibitor is selected from the group consisting of SU11271 (Sugen), SU11606 (Sugen), HPK-56 (Supergen) or K252a (Merck).

* * * * *